US007666392B2

(12) United States Patent
Kolb et al.

(10) Patent No.: US 7,666,392 B2
(45) Date of Patent: Feb. 23, 2010

(54) CLICK CHEMISTRY-DERIVED CYCLOPEPTIDE DERIVATIVES AS IMAGING AGENTS FOR INTEGRINS

(75) Inventors: Hartmuth C. Kolb, Playa Del Rey, CA (US); Kai Chen, Los Angeles, CA (US); Joseph C. Walsh, Pacific Palisades, CA (US); Qianwa Liang, Hacienda Heights, CA (US); Henry Clifton Padgett, Hermosa Beach, CA (US); Farhad Karimi, Canton, MA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 302 days.

(21) Appl. No.: 11/901,730

(22) Filed: Sep. 17, 2007

(65) Prior Publication Data

US 2008/0170992 A1    Jul. 17, 2008

Related U.S. Application Data

(60) Provisional application No. 60/844,837, filed on Sep. 15, 2006, provisional application No. 60/963,272, filed on Aug. 3, 2007.

(51) Int. Cl.
*A61K 49/00* (2006.01)
(52) U.S. Cl. ............ 424/9.1; 424/1.11; 424/1.65; 424/1.69; 424/9.4
(58) Field of Classification Search ............ 424/1.11, 424/1.65, 1.69, 1.81, 1.85, 1.89, 9.1, 9.2, 424/9.3, 9.36, 9.361, 9.363, 9.364, 5, 9.37, 424/9.4, 9.5, 9.6, 9.7, 9.8; 514/2, 5, 6, 9, 514/10, 11; 530/316, 317, 321, 322, 323, 530/328, 329, 330, 331, 332, 333, 338; 534/7, 534/10–16
See application file for complete search history.

(56) References Cited

FOREIGN PATENT DOCUMENTS

EP            1 733 742 A1    12/2006
WO    WO 2006/030291 A2    3/2006

OTHER PUBLICATIONS

Haubner et al., "Noninvasive imaging of alpha(v)beta3 integrin expression using 18F-labeled RGD-containing glycopeptides and positron emission tomography", Cancer Research Mar. 1, 2001, vol. 61, No. 5, pp. 1781-1785.
Chen et al., "MicroPET imaging of brain tumor angiogenesis with 18F-labeled PEGylated RGD peptide", European Journal of Nuclear Medicine and Molecular Imaging, Aug. 2004, vol. 31. No. 8, pp. 1081-1089.
Cai et al., "A thiol-reactive 18F-labelingn agent, N-[2-(4-18F-fluorobenzamido)ethyl peptide-based tracer for PET imaging of alpha v beta 3 integrin expression", Journal of Nuclear Medicine: Official Publication, Society of Nuclear Medicine, Jul. 2006, vol. 47, No. 7, pp. 1172-1180.

Zhang et al., "Quantitative PET imaging of tumor integrin alphavbeta3 expression with 18F-FRGD2", Journal of Nuclear Medicine: Official Publication, Society of Nuclear Medicine, Jan. 2006, vol. 47, No. 1, pp. 113-121.
Poethko et al., "Two-step methodology for high-yield routine radiohalogenation of peptides: 18F-labeled RGD and Octreotide Analogs", Journal of Nuclear Medicine, Society of Nuclear Medicine, Reston, VA, vol. 45, No. 5, May 2004, pp. 892-902.
Wu et al., "microPET imaging of glioma integrine {alpha}v{beta}3 expressioin using (64)Cu-labeled tetrameric RGD peptide", Journal of Nuclear Medicine: Official Publication, Society of Nuclear Medicine, Oct. 2005, vol. 46, No. 10, pp. 1707-1718.
Poethko et al., "Chemoselective pre-conjugate radiohalogenation of unprotected mono- and multimeric peptides via oxime formation", Radiochim ACTA, vol. 92, 2004, pp. 317-327.
Marik et al, "Click for PET: rapid preparation of [18F] fluoropeptides using CuI catalyzed 1,3-dipolar cycloaddition", Tetrahedron Letters, Elsevier, Amsterdam, NL, vol. 47, Jul. 31, 2006, pp. 6681-6684.
Kolb et al., "Application of Click Chemistry to the development of COX-2 and CA-II inhibitors", Abstracts of Papers American Chemical Society, vol. 231, Mar. 2006, pp. 403-MEDI.
Rijkers et al., "Efficient microwave-assisted synthesis of multivalent dendrimeric peptides using cycloaddition reaction (click) chemistry", Chemical Communications—Chemcom, Royal Society of Chemistry, GB, Aug. 19, 2005, pp. 4581-4583.
Chen et al., "MicroPET and autoradiographic imaging of breast cancer alphav-integrin expression using 18F- and 64CU-labeled RGD peptide", Bioconjugate Chemistry, ACS, Washington, DC, vol. 15, No. 1, 2004, pp. 41-49.
Dijkgraaf et al., "Synthesis of DOTA-conjugated multivalent cyclic-RGD peptide dendrimers via 1,3-dipolar cycloaddition and their biological evaluation: implications for tumor targeting and tumor imaging purposes", Organic & Biomolecular Chemistry Mar. 21, 2007, vol. 5, No. 6, pp. 935-944.
Sirion et al., "An efficient F-18 labeling method for PET study: Huisgen 1,3-dipolar cycloaddition of bioactive substances and F-18-labeled compounds", Tetrahedron Letters, Elsevier, Amsterdam, NL, vol. 48, No. 23, Jun. 4, 2007, pp. 3953-3957.
Kuijpers et al, "Preparation and evaluation of glycosylated arginine-glycine-aspartate (RGD) derivatives for integrine targeting", Bioconjugate Chemistry Nov.-Dec. 2007, vol. 18, No. 6, pp. 1847-1854.
Li et al., "Click chemistry for (18)F-labeling of RGD peptides and microPET imaging of tumor integrin alphavbeta3 expression", Bioconjugate Chemistry Nov.-Dec. 2007, vol. 18, No. 6, pp. 1987-1994.

(Continued)

*Primary Examiner*—D L Jones
(74) *Attorney, Agent, or Firm*—Peter L. Kendall

(57) ABSTRACT

The present application is directed to radiolabeled cyclic polypeptides, pharmaceutical compositions comprising radiolabeled cyclic polypeptides, and methods of using the radiolabeled cyclic polypeptides. Such polypeptides can be used in imaging studies, such as Positron Emitting Tomography (PET) or Single Photon Emission Computed Tomography (SPECT).

29 Claims, 17 Drawing Sheets

OTHER PUBLICATIONS

Christian W. Tornøe and Morten Meldal, "Regiospecific Copper(I)-Catalyzed 1,3-Dipolar Cycloadditions on Solid-Phase" poster presentation, Jun. 11, 2001, Second International and Seventeenth American Peptide Symposium held by the American Peptide Society, San Diego, California.

Michal Lebl and Richard A. Houghten, "Peptides the Wave of the Future Proceedings of the Second International and the Seventeenth American Peptide Symposium", Dec., 2001, pp. 263-264, American Peptide Society, San Diego, California.

Katumitu Hayakawa, Shoko Minami, and Sumio Nakamura, "Kinetics of the Oxidation of Ascorbic Acid by the Copper(II) Ion in an Acetate Buffer Solution", Bulletin of the Chemical Society of Japan, vol. 46, pp. 2788-2791 (1973).

us 7,666,392 B2

CLICK CHEMISTRY-DERIVED CYCLOPEPTIDE DERIVATIVES AS IMAGING AGENTS FOR INTEGRINS

RELATED APPLICATION

This application claims priority to U.S. Provisional Application No. 60/844,837, filed Sep. 15, 2006 and to U.S. Provisional Application No. 60/963,272, filed Aug. 3, 2007, the contents of each of which are hereby incorporated in their entirety by reference.

FIELD OF THE INVENTION

The present application is directed to radiolabeled cyclic polypeptides (cyclopeptides), pharmaceutical compositions comprising radiolabeled cyclic polypeptides, and methods of using the radiolabeled cyclic polypeptides. The present application is further directed to methods of preparing the radiolabeled cyclic polypeptides. Such polypeptides can be used in imaging studies, such as Positron Emitting Tomography (PET) or Single Photon Emission Computed Tomography (SPECT).

In particular this application discloses the preparation and use of radiolabeled cyclopeptide analogs for imaging integrins (e.g., integrin $\alpha_v\beta_3$) in vivo. Click chemistry is utilized to attach a radiolabel to cyclopeptides that contain an Arg-Gly-Asp (RGD) fragment and that further carry hydrophilic linkages, such as oligo- or poly-ethyleneglycol ("PEG") moieties, polar amino acid moieties, sugars, or sugar mimetics, such as cyclohexane diols or polyols. One advantage disclosed in the present application is a click chemistry labeling step that is easy to perform, that is fast and provides high yields of radiolabeled products that are easy to purify. The binding affinities of the radiolabeled cyclopeptide analogs for different integrins have been determined using biochemical in vitro assays, such as cell-binding assays or surface plasmon resonance assays. The click chemistry-derived integrin ligands of the present application display surprisingly high binding affinities to the biological target, and demonstrate very favorable pharmacokinetic behavior in mice (e.g. high tumor uptake and fast clearance through predominantly renal routes).

BACKGROUND OF THE INVENTION

A number of medical diagnostic procedures, including PET and SPECT utilize radiolabeled compounds. PET and SPECT are very sensitive techniques and require small quantities of radiolabeled compounds, called tracers. The labeled compounds are transported, accumulated and converted in vivo in exactly the same way as the corresponding non-radioactively compound. Tracers, or probes, can be radiolabeled with a radionuclide useful for PET imaging, such as $^{11}$C, $^{13}$N, $^{15}$O, $^{18}$F, $^{61}$Cu, $^{62}$Cu, $^{64}$Cu, $^{67}$Cu, $^{68}$Ga, $^{124}$I, $^{125}$I and $^{131}$I, or with a radionuclide useful for SPECT imaging, such as $^{99m}$Tc, $^{75}$Br, $^{61}$Cu, $^{153}$Gd, $^{125}$I, $^{131}$I and $^{32}$P.

PET creates images based on the distribution of molecular imaging tracers carrying positron-emitting isotopes in the tissue of the patient. The PET method has the potential to detect malfunction on a cellular level in the investigated tissues or organs. PET has been used in clinical oncology, such as for the imaging of tumors and metastases, and has been used for diagnosis of certain brain diseases, as well as mapping brain and heart function. Similarly, SPECT can be used to complement any gamma imaging study, where a true 3D representation can be helpful, for example, imaging tumor, infection (leukocyte), thyroid, or bones.

Angiogenesis plays a vital role in tumor growth and metastatic spread. Tumor angiogenesis is a multi-step process characterized by chemotactic and mitogenic response of endothelial cells to angiogenic growth factors, proteolytic degradation of extracellular matrix, and modulation of endothelial cell interaction with extracellular matrix mediated by integrin receptors. Each of these steps may represent a potential target for the development of tumor angiogenic and metastatic diagnostics.

Integrins are a family of membrane-spanning adhesion receptors composed of noncovalently linked α and β subunits, which combine to form a variety of heterodimers with different ligand recognition properties. Several integrins have been shown to interact with polypeptide domains containing the Arg-Gly-Asp ("RGD") amino acid sequence present in various extracellular matrix-associated adhesive glycoproteins. Besides cell adhesion to extracellular matrix, integrins also mediate intracellular events that control cell migration, proliferation, and survival.

One member of the integrin family, $\alpha_v\beta_3$ integrin, plays a key role in angiogenesis. It interacts with several extracellular matrix proteins, such as vitronectin, fibrinogen, fibronectin, thrombin, and thrombospondin, and cooperates with molecules such as metalloproteases, growth factors, and their receptors. Due to its numerous functions and relatively limited cellular distribution, $\alpha_v\beta_3$ integrin represents an attractive target for diagnostic and therapeutic intervention. In addition, findings that several extracellular matrix proteins, such as vitronectin, fibrinogen, and thrombospondin interact with integrins via the RGD sequence has lead to the development of synthetic linear and cyclic peptides containing RGD sequence for integrin targeting. See e.g. DE 197 25 368, U.S. Pat. No. 5,849,692, U.S. Pat. No. 6,169,072, U.S. Pat. No. 6,566,491, U.S. Pat. No. 6,610,826, and WO 2005/111064.

It has also been demonstrated in a number of murine tumor models that radiolabeled peptides containing the RGD motif can be used for non-invasive investigation of $\alpha_v\beta_3$ integrin expression. The development of noninvasive methods to visualize and quantify integrin $\alpha_v\beta_3$ expression in vivo appears to be closely related to the success of antiangiogenic therapy based on integrin antagonism. Precise documentation of integrin receptor levels allows appropriate selection of patients who will most likely benefit from an anti-integrin treatment regimen. Imaging can also be used to provide an optimal dosage and time course for treatment based on receptor occupancy studies. In addition, imaging integrin expression is used to evaluate anti-integrin treatment efficacy and to develop new therapeutic drugs with favorable tumor targeting and in vivo kinetics.

Kessler and co-workers [1] developed the pentapeptide cyclo(-Arg-Gly-Asp-D-Phe-Val-) ("c(RGDfV)") which showed high affinity and selectivity for integrin $\alpha_v\beta_3$. To date, most integrin $\alpha_v\beta_3$ targeted PET studies have been focused on radiolabeling of c(RGDfV)-based antagonists due to its high binding affinity (nanomolar to subnanomolar range for monomeric and multimeric c(RGDfV) respectively). In the late 1990's, the monomeric peptide c(RGDyV) was labeled by Haubner et al. [2] with $^{125}$I. This tracer revealed receptor-specific tumor uptake in vivo. However, the labeled peptide had rapid tumor washout and unfavorable hepatobiliary excretion resulting from its high lipophilicity, which limited its further application. Glycosylation on the lysine side chain of a similar RGD peptide, c(RGDyK), decreased lipophilicity and hepatic uptake [3]. A glycopeptide based on c(RGDfK), [$^{18}$F]galacto-RGD, was then synthesized:

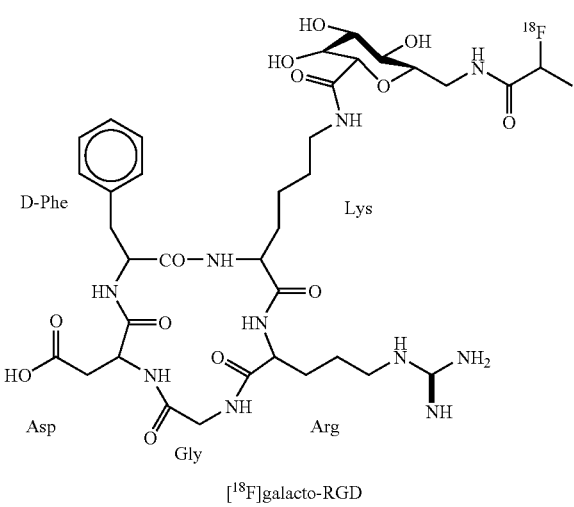

[¹⁸F]galacto-RGD

It was demonstrated that [¹⁸F]galacto-RGD exhibited integrin $\alpha_v\beta_3$-specific tumor uptake in integrin-positive M21 melanoma xenograft model [4-6, see also 19]. Moreover, [¹⁸F]galacto-RGD was sensitive enough for visualization of integrin $\alpha_v\beta_3$ expression resulting exclusively from the tumor vasculature using an A431 human squamous cell carcinoma model, in which the tumor cells are integrin negative. Initial clinical trials in healthy volunteers and a limited number of cancer patients revealed that this tracer could be safely administered to patients and was able to delineate certain lesions that were integrin-positive with reasonable contrast.

[¹⁸F]Galacto-RGD currently represents one promising integrin marker for PET imaging of angiogenesis. As a monomeric RGD peptide tracer, it has relatively low tumor targeting efficacy; clinical use of this tracer is severely limited because of its relatively low integrin binding affinity, modest tumor standard uptake values, and unfavorable pharmacokinetic behavior. Therefore, tumors with low integrin expression level may not be detectable. In addition, prominent activity accumulation in the liver, kidneys, spleen, and intestines was observed in both preclinical models and human studies. As a result, it was difficult to visualize lesions in the abdomen. This tracer is also very difficult to synthesize, thereby limiting its availability.

Conjugation of PEG (poly(ethyleneglycol)) ("PEGylation") has been shown to improve many properties of peptides and proteins, including plasma stability, immunogenicity, and pharmacokinetics. Chen et al. [7-9] conjugated RGD-containing peptides with PEG moieties of different sizes and synthesized radioiodinated, ¹⁸F- and ⁶⁴Cu-labeled derivatives. PEGylation demonstrated an effect on the pharmacokinetics, tumor uptake and retention of the RGD peptides, which seem to depend strongly on the nature of lead structure and on the size of the PEG moiety. Additional strategies for improving pharmacokinetic behavior as well as tumor uptake and retention pattern of peptides with an RGD motif include introduction of hydrophilic amino acids and multimerisation of RGD.

SUMMARY OF THE INVENTION

Applicants observed that despite a few good examples of RGD-containing tracers, several key challenges remain to be resolved. Firstly, the pharmacokinetic behavior of the tracer needs to be improved. Although glycosylation improved the pharmacokinetic behavior of a number of tracers to a certain degree, prominent activity accumulation in the liver, kidneys, spleen, and intestines is still observed in both preclinical models and human studies, which makes it difficult to visualize lesions in the abdomen. Secondly, a major drawback of the strategies examined by others is that the radiolabeling process is very difficult to perform, which limits the exploration of improved derivatives and the use of these imaging agents as standard clinical biomarkers.

The present application discloses effective imaging agents developed for detecting blood vessel growth in tumors (angiogenesis) in vivo. In the labeled cyclopeptides of the present application, RGD-containing cyclic peptides carry polar residues on a pendant amino acid side chain; those polar residues are coupled with a moiety comprising a radionuclide via a 'click chemistry' linkage (i.e. a 1,4- or 1,5-disubstituted 1,2,3-triazole). These click chemistry-derived compounds are easy to both synthesize and radiolabel. The compounds demonstrate surprisingly high binding affinity to integrin $\alpha_v\beta_3$, and improved pharmacokinetic properties compared to cyclic polypeptides belonging to the same class. The imaging agents disclosed in the present application are used as a marker for imaging integrins in vivo. More specifically, this application discloses a means for detecting blood vessel growth in certain cancers in vivo, as well as a means for monitoring the efficacy of cancer therapy. Since the imaging agent allows in vivo imaging of blood vessel growth in solid tumors, it enables personalized anti-angiogenesis cancer therapies.

To solve the problem of low signal to noise ratios, a library of potential integrin markers using the RGD sequence as a binding motif have been prepared. The library, assembled using click chemistry, was screened for binding to integrins. Those compounds that displayed high binding affinities were selected for radiolabeling with positron-emitting isotopes or conjugation with appropriate linker moieties and radioactive isotopes such as [¹⁸F]-fluorine for in vivo PET imaging. Applicants' approach of using click chemistry enabled rapid synthesis and testing of many different potential integrin ligands as candidate PET tracers.

DETAILED DESCRIPTION

The embodiments of the invention and the various features and advantageous details thereof are explained more fully with reference to the non-limiting embodiments and examples that are described and/or illustrated in the accompanying drawings and detailed in the following description. It should be noted that the features of one embodiment may be employed with other embodiments as the skilled artisan would recognize, even if not explicitly stated herein. The examples used herein are intended merely to facilitate an understanding of ways in which the invention may be practiced and to further enable those of skill in the art to practice the embodiments of the present application. Accordingly, the examples and embodiments herein should not be construed as limiting the scope of the application, which is defined solely by the appended claims.

DEFINITIONS

Figure 1:
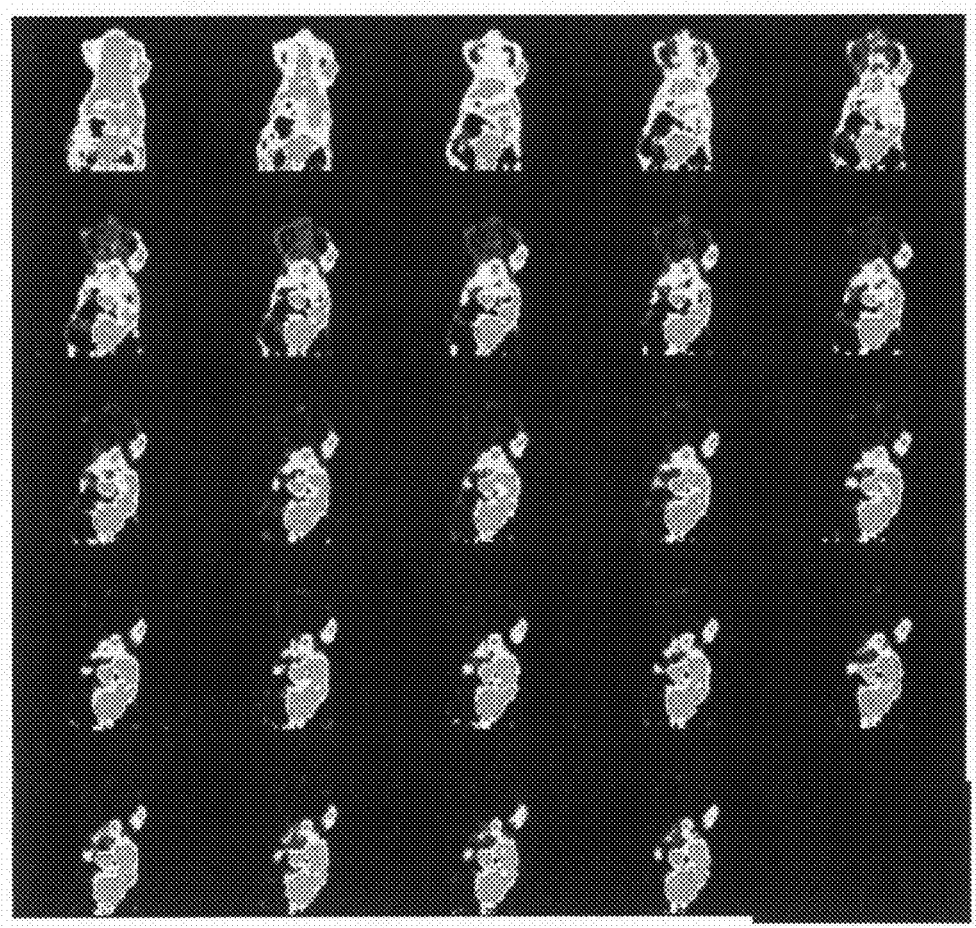
FIG. 1 is a time course imaging using micro-PET imaging in a U87MG Xenograft Mouse Model of Compound 7.
Figure 2A:
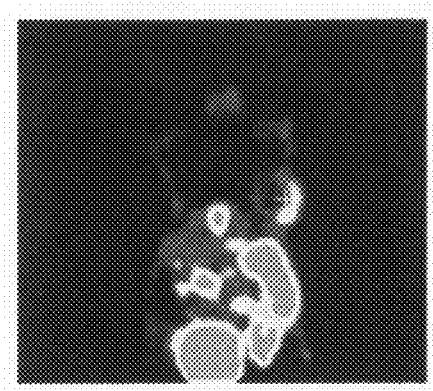
FIG. 2A is the uptake of [¹⁸F]galacto-RGD in a U87MG Xenograft Mouse Model.
Figure 2B:
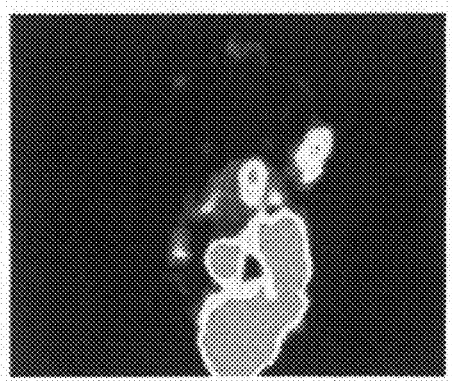
FIG. 2B is the uptake of Compound 7 in a U87MG Xenograft Mouse Model.
Figure 3:
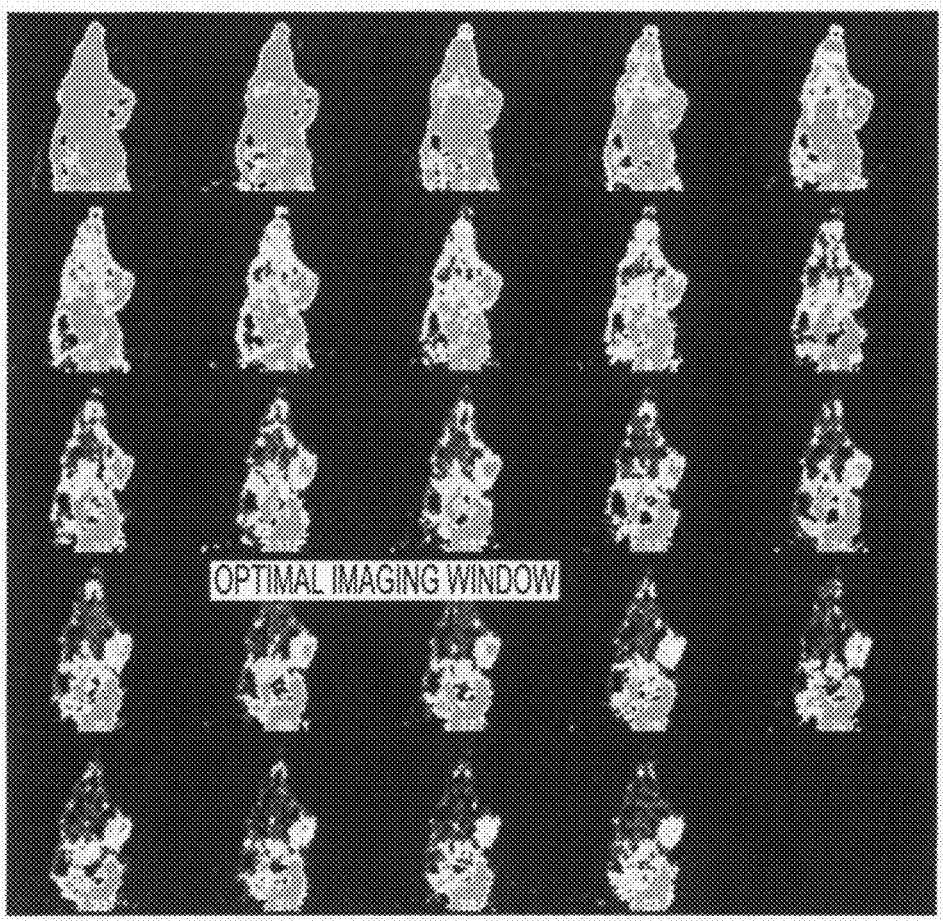
FIG. 3 is a time course imaging using micro-PET imaging in a A427 Xenograft Mouse Model of Compound 7.
Figure 4A:
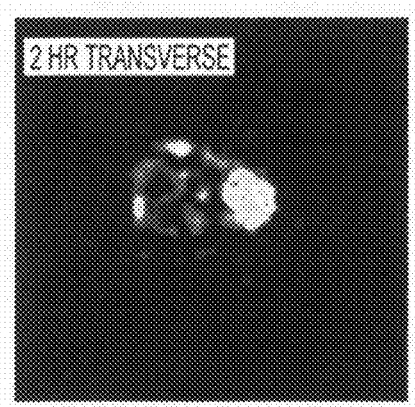
FIG. 4A is a transverse image collected two hours after intravenous administration of Compound 7 in an A427 Xenograft Mouse Model.
Figure 4B:
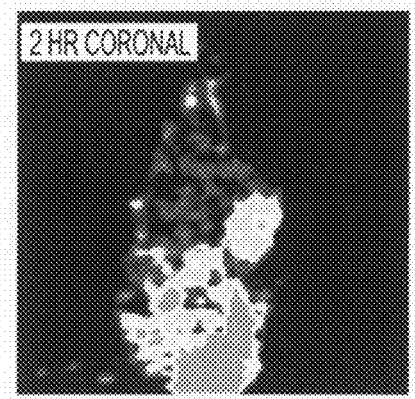
FIG. 4B is a coronal image collected two hours after intravenous administration of Compound 7 in an A427 Xenograft Mouse Model.
Figure 5:
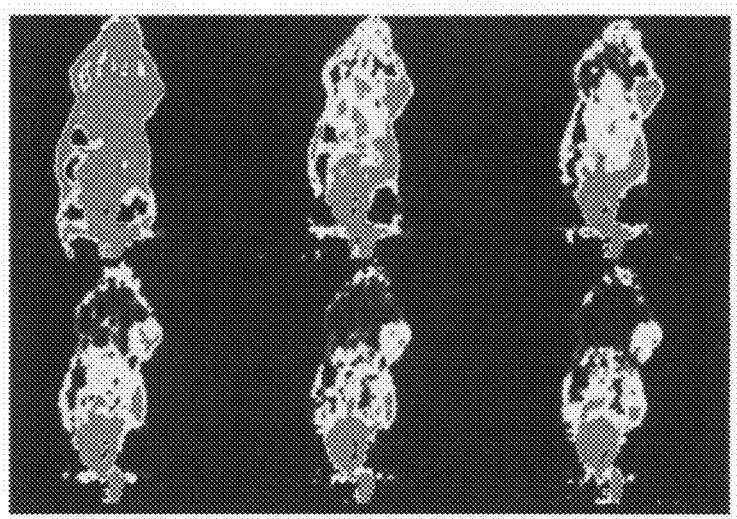
FIG. 5 is a time course imaging using micro-PET imaging in a U87MG Xenograft Mouse Model of Compound 10.
Figure 6A:
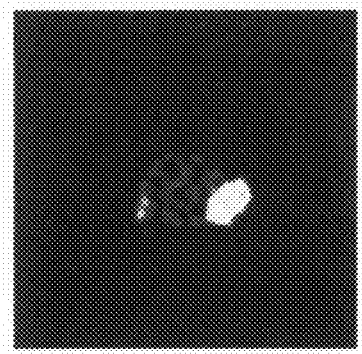
FIG. 6A is a transverse image collected two hours after intravenous administration of Compound 10 in an U87MG Xenograft Mouse Model.
Figure 6B:
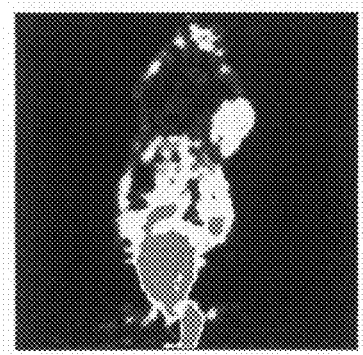
FIG. 6B is a coronal image collected two hours after intravenous administration of Compound 10 in an U87MG Xenograft Mouse Model.
Figure 7:
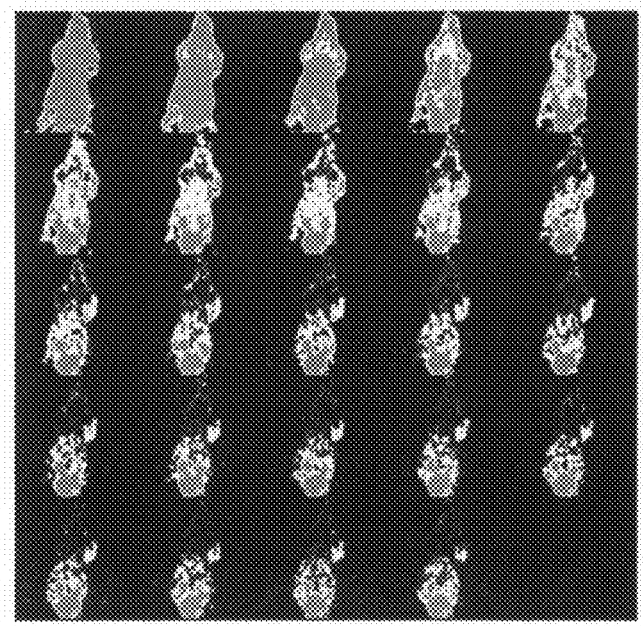
FIG. 7 is a time course imaging using micro-PET imaging in a A427 Xenograft Mouse Model of Compound 10.
Figure 8A:
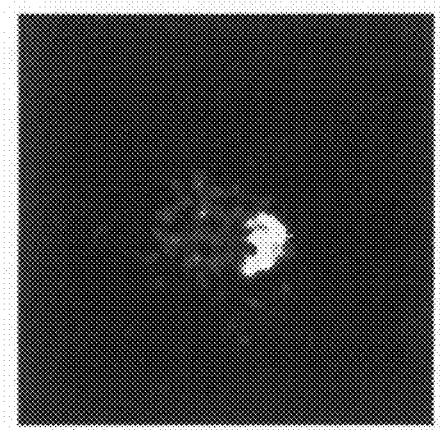
FIG. 8A is a transverse image collected two hours after intravenous administration of Compound 10 in an A427 Xenograft Mouse Model.
Figure 8B:
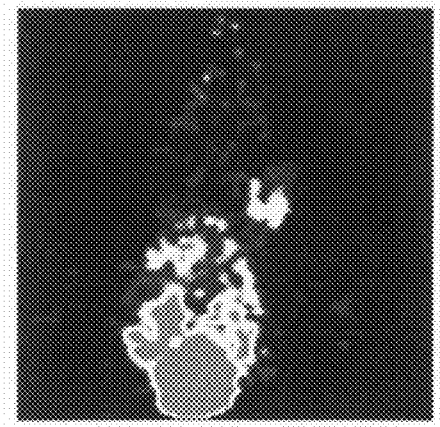
FIG. 8B is a coronal image collected two hours after intravenous administration of Compound 10 in an A427 Xenograft Mouse Model.

Unless specifically noted otherwise herein, the definitions of the terms used are standard definitions used in the art of organic and peptide synthesis and pharmaceutical sciences.

An "alkyl" group is a straight, branched, saturated or unsaturated, aliphatic group having a chain of carbon atoms, optionally with oxygen, nitrogen or sulfur atoms inserted between the carbon atoms in the chain or as indicated. Alkyl groups may be optionally substituted. A $(C_1-C_6)$alkyl, for example, includes alkyl groups that have a chain of between 1 and 6 carbon atoms, and include, for example, the groups methyl, ethyl, propyl, isopropyl, vinyl, allyl, 1-propenyl, isopropenyl, ethynyl, 1-propynyl, 2-propynyl, 1,3-butadienyl, penta-1,3-dienyl, and the like. An alkyl group, such as a "$C_1-C_6$ alkyl," that forms a part of a group or linker is a divalent alkyl group, and also may be referred to as an "alkylene" group. Similarly, an alkenyl group, alkynyl group, aryl group, etc in a structure that is shown as a divalent group may be referred to as an alkenylenyl, alkynylenyl, arylenyl group respectively.

An alkyl as noted with another group such as an aryl group, represented as "arylalkyl" for example, is intended to be a straight, branched, saturated or unsaturated aliphatic divalent group with the number of atoms indicated in the alkyl group (as in $(C_1-C_6)$alkyl, for example) and/or aryl group or when no atoms are indicated means a bond between the aryl and the alkyl group. Nonexclusive examples of such group include benzyl, phenylethyl and the like.

An "alkylene" group or "alkylenyl group" is a straight, branched, saturated or unsaturated aliphatic divalent group with the number of atoms indicated in the alkyl group; for example, a —$(C_1-C_3)$alkylene- or —$(C_1-C_3)$alkylenyl-.

The term "alkenyl" refers to unsaturated groups which contain at least one carbon-carbon double bond and includes straight-chain, branched-chain and cyclic groups. Alkene groups may be optionally substituted. Exemplary groups include 1-butenyl, 2-butenyl, 3-butenyl, isobutenyl, 1-propenyl, 2-propenyl, and ethenyl.

The term "alkynyl" refers to unsaturated groups which contain at least one carbon-carbon triple bond and includes straight-chain, branched-chain and cyclic groups. Alkyne groups may be optionally substituted. Exemplary groups include 1-butynyl, 2-butynyl, 3-butynyl, 1-propynyl, 2-propynyl and ethynyl.

The term "carbocycle" (or carbocyclyl) as used herein refers to a $C_3$ to $C_8$ monocyclic, saturated, partially saturated or aromatic ring. Bonds in a carbocycle depicted as "———" indicate bonds that can be either single or double bonds. Carbocycles may be optionally substituted. Non-exclusive examples of carbocycle include cyclopropane, cyclobutane, cyclopentane, cyclohexane, cycloheptane, cyclopentene, cyclohexene, cycloheptene, cyclooctene, benzyl, naphthene, anthracene, phenanthracene, biphenyl and pyrene.

A "heterocycle" is a carbocycle group wherein one or more of the atoms forming the ring is a heteroatom that is a N, O, or S. The heterocycle may be saturated, partially saturated or aromatic. Bonds in a heterocycle depicted as "———" indicate bonds that can be either single or double bonds. Heterocycles may be optionally substituted. Non-exclusive examples of heterocyclyl (or heterocycle) include piperidyl, 4-morpholyl, 4-piperazinyl, pyrrolidinyl, 1,4-diazaperhydroepinyl, acetonidyl-4-one, 1,3-dioxanyl, thiophenyl, furanyl, pyrrolyl, pyrazolyl, pyridinyl, pyrimidinyl, pyridazinyl, pyranyl and the like.

The term "alkoxy" or "alkyloxy" includes linear or branched alkyl groups that are attached to divalent oxygen. The alkyl group is as defined above. Examples of such substituents include methoxy, ethoxy, t-butoxy, and the like. The term "alkoxyalkyl" refers to an alkyl group that is substituted with one or more alkoxy groups. Alkoxy groups may be optionally substituted. The term "aryloxy" refers to an aryl group that is attached to an oxygen, such as phenyl-O—, etc.

The term "optionally substituted" or "substituted" refers to the specific group wherein one to four hydrogen atoms in the group may be replaced by one to four substituents, independently selected from alkyl, aryl, alkylene-aryl, hydroxy, alkoxy, aryloxy, perhaloalkoxy, heterocycle, azido, amino, guanidino, amidino, halo, alkylthio, oxo, acylalkyl, carboxy esters, carboxyl, carboxamido, nitro, acyloxy, aminoalkyl, alkylaminoaryl, alkylaminoalkyl, alkoxyaryl, arylamino, phosphono, sulfonyl, carboxamidoaryl, hydroxyalkyl, haloalkyl, cyano, alkoxyalkyl, and perhaloalkyl. In addition, the term "optionally substituted" or "substituted" in reference to $R_2$ or $R_3$ includes groups substituted by one to four substituents, as identified above, that further comprise a positron or gamma emitter. Such positron emitters include, but are not limited to, $^{11}$C, $^{13}$N, $^{15}$O, $^{18}$F, $^{61}$Cu, $^{62}$Cu, $^{64}$Cu, $^{67}$Cu, $^{68}$Ga, $^{124}$I, $^{125}$I, $^{131}$I, $^{99}$Tc, $^{75}$Br, $^{153}$Gd and $^{32}$P.

As used herein, the term "side chain" of a natural or unnatural amino acid refers to "Q" group in the amino acid formula, as exemplify with $NH_2CH(Q)CO_2H$.

As used herein, the term "polar amino acid moiety" refers to the side chain, Q, of a polar natural or unnatural amino acid. Polar natural amino acids include but are not limited to arginine, asparagine, aspartic acid, cysteine, glutamic acid, glutamine, histidine and lysine.

As used herein, "natural amino acid" refers to the naturally occurring amino acids: glycine, alanine, valine, leucine, isoleucine, serine, methionine, threonine, phenylalanine, tyrosine, tryptophan, cysteine, proline, histidine, aspartic acid, asparagine, glutamic acid, glutamine, arginine and lysine.

The term "unnatural amino acid" refers to any derivative of a natural amino acid including for example D and L forms, and α- and β-amino acid derivatives. It is noted that certain amino acids, e.g., hydroxyproline, that are classified as a non-natural amino acid herein, may be found in nature within a certain organism or a particular protein. The following non-exclusive examples of non-natural amino acids and amino acid derivatives may be used according to the application (common abbreviations in parentheses): β-alanine (β-ALA), γ-aminobutyric acid (GABA), ornithine, 2-aminobutyric acid (2-Abu), α,β-dehydro-2-aminobutyric acid (8-AU), 1-aminocyclopropane-1-carboxylic acid (ACPC), aminoisobutyric acid (Aib), γ-carboxyglutamic acid, 2-amino-thiazoline-4-carboxylic acid, 5-aminovaleric acid (5-Ava), 6-aminohexanoic acid (6-Ahx), 8-aminooctanoic acid (8-Aoc), 11-aminoundecanoic acid (11-Aun), 12-aminododecanoic acid (12-Ado), 2-aminobenzoic acid (2-Abz), 3-aminobenzoic acid (3-Abz), 4-aminobenzoic acid (4-Abz), 4-amino-3-hydroxy-6-methylheptanoic acid (Statine, Sta), aminooxyacetic acid (Aoa), 2-aminotetraline-2-carboxylic acid (ATC), 4-amino-5-cyclohexyl-3-hydroxypentanoic acid (ACHPA), para-aminophenylalanine (4-$NH_2$-Phe), biphenylalanine (Bip), para-bromophenylalanine (4-Br-Phe), orthochlorophenylalanine] (2-Cl-Phe), meta-chlorophenylalanine (3-Cl-Phe), para-chlorophenylalanine (4-Cl-Phe), meta-chlorotyrosine (3-Cl-Tyr), para-benzoylphenylalanine (Bpa), tert-butylglycine (TLG), cyclohexylalanine (Cha), cyclohexylglycine (Chg), 2,3-diaminopropionic acid (Dpr), 2,4-diaminobutyric acid (Dbu), 3,4-dichlorophenylalanine (3,4-$Cl_2$-Phe), 3,4-difluororphenylalanine (3,4-$F_2$-Phe), 3,5-diiodotyrosine (3,5-$I_2$-Tyr), ortho-fluorophenylalanine (2-F-Phe), meta-fluorophenylalanine (3-F-Phe), para-fluorophenylalanine (4-F-Phe), meta-fluorotyrosine (3-F-Tyr), homoserine (Hse), homophenylalanine (Hfe), homotyrosine (Htyr), 5-hydroxytryptophan (5-OH-Trp), hydroxyproline (Hyp), para-iodophenylalanine (4-I-Phe), 3-iodotyrosine (3-I-Tyr), indoline-2-carboxylic acid (Idc), isonipecotic acid (Inp), meta-methyltyrosine (3-Me-Tyr), 1-naphthylalanine (1-Nal), 2-naphthylalanine (2-Nal), para-nitrophenylalanine (4-$NO_2$-Phe), 3-nitrotyrosine (3-$NO_2$-Tyr), norleucine (Nle), norvaline (Nva), ornithine (Orn), ortho-phosphotyrosine ($H_2PO_3$-Tyr), octahydroindole-2-carboxylic acid (Oic), penicillamine (Pen), pentafluorophenylalanine ($F_5$-Phe), phenylglycine (Phg), pipecolic acid (Pip), propargylglycine (Pra), pyroglutamic acid (PGLU), sarcosine (Sar), tetrahydroisoquinoline-3-carboxylic acid (Tic), thienylalanine, and thiazolidine-4-carboxylic acid (thioproline, Th). Additionally, N-alkylated amino acids may be used, as well as amino acids having amine-containing side chains (such as Lys and Orn) in which the amine has been acylated or alkylated.

As used herein, "sugar moiety" refers to an oxidized, reduced or substituted saccharide monoradical or diradical covalently attached via any atom(s) of the sugar moiety. Representative sugars include, by way of illustration, hexoses such as D-glucose, D-mannose, D-xylose, D-galactose, vancosamine, 3-desmethyl-vancosamine, 3-epi-vancosamine, 4-epi-vancosamine, acosamine, actinosamine, daunosamine, 3-epi-daunosamine, ristosamine, D-glucamine, N-methyl-D-glucamine, D-glucuronic acid, N-acetyl-D-glucosamine, N-acetyl-D-galactosamine, sialyic acid, iduronic acid, L-fucose, and the like; pentoses such as D-ribose or D-arabinose; ketoses such as D-ribulose or D-fructose; disaccharides such as 2-O-(α-L-vancosaminyl)-β-D-glucopyranose, 2-O-(3-desmethyl-α-L-vancosaminyl)-β-D-glucopyranose, sucrose, lactose, or maltose; derivatives such as acetals, amines, acylated, sulfated and phosphorylated sugars; and oligosaccharides having from 2 to 10 sugar units.

As used herein, a hexose structure that is represented below, for example:

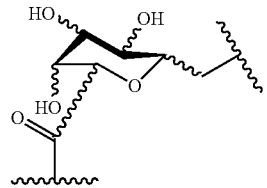

showing the curved lines ($\sim\!\!\sim$) is intended to represent a structure having the stereochemistry of any one of the natural sugars, including allose, altrose, galactose, glucose, gulose, idose, mannose, talose, etc. . . . , as well as their unnatural and synthetic hexose analogs and derivatives, and also includes certain sugar moieties.

As used herein, "sugar mimetic" refers to carbocycles or heterocycles substituted with at least one hydroxyl group. Such carbocycle groups include, but are not limited to cyclohexane, cyclohexene, cyclopentane and cyclobutane; such heterocycles include, but are not limited to, pyrrolidine and piperidine.

As used herein, "PEG moiety" refers to a fragment of poly (ethylene glycol), a polymer of ethylene oxide. PEG has the formula:

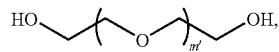

where m' is an integer between 1 and 200, alternatively between 1 and 110 or between 10 and 90; m' can also be an integer between 50 and 75. Alternately m' can be an integer between 1 and 50 or even between 1 and 15.

"Linker" as used herein refers to a chain comprising 1 to 200 atoms and may comprise atoms or groups, such as C, —NR—, O, S, —S(O)—, —S(O)$_2$—, CO, —C(NR)—, a PEG moiety, and the like, and wherein R is H or is selected from the group consisting of ($C_{1-10}$)alkyl, ($C_{3-8}$)cycloalkyl, aryl($C_{1-5}$)alkyl, heteroaryl($C_{1-5}$)alkyl, amino, aryl, heteroaryl, hydroxy, ($C_{1-10}$)alkoxy, aryloxy, heteroaryloxy, each substituted or unsubstituted. The linker chain may also comprise part of a saturated, unsaturated or aromatic ring, including monocyclic (e.g. a 1,5-cyclohexylenyl group, sugar mimetic, and sugar moiety), polycyclic and heteroaromatic rings (e.g. a 2,4-pyridinyl group etc. . . . ). The representation of "($C_{1-3}$)alkyl", for example, is used interchangeably with "$C_1$-$C_3$alkyl" to mean the same. As used herein, the term "linker" may be used to link interconnecting moieties such as —X—YR$_2$R$_3$, including linking a cyclic polypeptide moiety and a triazole moiety.

As used herein, where a divalent group, such as a linker, is represented by a structure -A-B—, as shown below, it is intended to also represent a group that may be attached in both possible permutations, as noted in the two structures below.

$\xi\text{-B-A-}\xi$ may also be $\xi\text{-B-A-}\xi$

As used herein, the phrase "pharmaceutically acceptable carrier" refers to an excipient that may optionally be included in the compositions of the present application and that causes no significant adverse toxicological effects when administered in vivo.

As used herein, the term "patient" refers to any warm-blooded animal, such as a mouse, dog or human.

The compounds of the present application may be in the form of free bases or pharmaceutically acceptable acid addition salts thereof. The term "pharmaceutically-acceptable salts" are salts commonly used to form alkali metal salts and to form addition salts of free acids or free bases. The nature of the salt may vary, provided that it is pharmaceutically acceptable. Suitable pharmaceutically acceptable acid addition salts of compounds for use in the present methods may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfon/c, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically-acceptable base addition salts of compounds of use in the present methods include metallic salts made from aluminum, calcium, lithium, magnesium, potassium, sodium and zinc or organic salts made from N, NT-dibenzylethylenediamine, chloroprocaine, choline, diethanolamine, ethylenediamine, meglumine-(N-methylglucamine) and procaine.

EMBODIMENTS, ASPECTS AND VARIATIONS OF THE INVENTION

The present application provides the following embodiments, aspects and variations:

One aspect of the present application is a cyclopeptide of formula I:

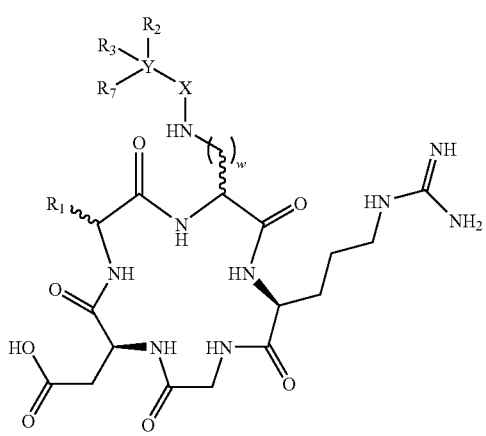

wherein:

$R_1$ is selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted;

$R_7$ is absent or is selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted; wherein $R_2$, $R_3$ and $R_7$ are not all H;

X is a 5 or 6-membered heterocycle or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

Y is a 5 or 6-membered heterocycle, or a linker comprising a hydrophilic moiety selected from the group consisting of hydroxyl, carbonyl, sulfonamide, sulfonate, phosphate, polar amino acid moiety, PEG moiety, sugar mimetic, and sugar moiety; where at least one of X and Y, but not both X and Y is a 5 or 6-membered heterocycle; and w is 1, 2, 3, 4, or 5;

wherein any one of X, Y, $R_2$, $R_3$, and $R_7$ comprises a radionuclide selected from the group consisting of positron or gamma emitters.

In certain variations of each of the embodiments and aspects of the present application, the 5-membered heterocycle is a substituted 1,2,3-triazolyl group as disclosed herein.

In one embodiment of any of the aspects disclosed herein, Y is a 5 or 6-membered heterocycle; and X is a linker either comprising a sugar mimetic selected from the group consisting of a 4 to 6-membered carbocycle substituted with at least one hydroxyl group and a 5- to 6-membered heterocycle substituted with at least one hydroxyl group or comprising a sugar moiety selected from the group consisting of glucose and galactose. In another embodiment, X is a linker comprising a sugar mimetic selected from the group consisting of a hydroxylated cyclohexanyl group, a hydroxylated cyclopentanyl group, a hydroxylated pyrrolidinyl group, and a hydroxylated piperidinyl group. In yet another embodiment, Y is a 5 or 6-membered heterocycle; X is selected from the group consisting of:

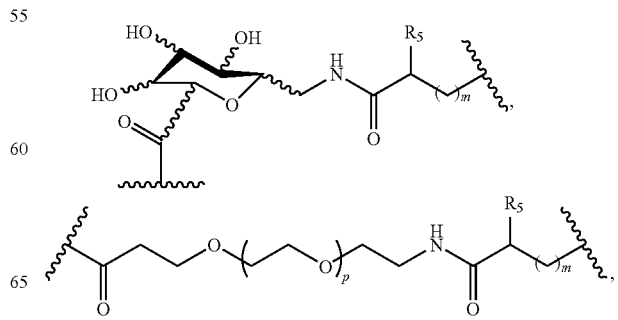

-continued

A is selected from the group consisting of:

where Z is selected from the group consisting of:

and

W is selected from the group consisting of:

and each $R_1$ is independently selected from the group consisting of a side chain of a natural amino acid and a side chain of an unnatural amino acid, wherein the natural amino acid and the unnatural amino acid is either in the D or L form;

each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted;

each $R_6$ is independently selected from the group consisting of —H, —OH, $C_1$-$C_6$ alkyl, $C_2$-$C_6$ alkenyl, $C_2$-$C_6$ alkynyl, $C_1$-$C_6$ alkyloxy, aryl-($C_1$-$C_6$ alkylene)-, hydroxy-$C_1$-$C_6$-alkyl, and $C_1$-$C_6$-alkoxy-$C_1$-$C_6$-alkyl, wherein the alkyl alkenyl, alkynyl, alkyloxy, and aryl-alkylene groups are each optionally substituted;

each v is 0, 1, 2, 3, or 4; m is 0, 1, 2, 3 or 4; p is an integer between 1 and 110; q is 1, 2, 3 or 4; r is 1, 2 or 3; r' is 0 or 1; s is 1, 2, 3 or 4; and the radionuclide is selected from the group consisting of $^{11}$C, $^{13}$N, $^{15}$O, $^{18}$F, $^{61}$Cu, $^{62}$Cu, $^{64}$Cu, $^{67}$Cu, $^{68}$Ga, $^{124}$I, $^{125}$I, $^{131}$I, $^{99}$Tc, $^{75}$Br, $^{153}$Gd and $^{32}$P; wherein the configuration of the chiral centers may be R or S or mixtures thereof.

In yet another embodiment, $R_1$ is a side chain of a natural amino acid; $R_7$ is absent;

X is

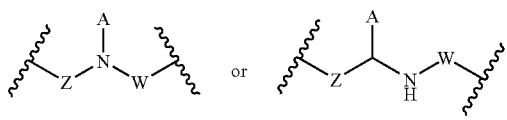

Y is 1,2,3-triazolyl; and $R_2$ and $R_3$ are each independently selected from the group consisting of —H, $C_1$-$C_6$ alkyl, $C_2$-$C_6$ alkenyl, and $C_2$-$C_6$ alkynyl, wherein the alkyl, alkenyl, and alkynyl groups are each optionally substituted, wherein $R_2$ and $R_3$ are not both H; and either $R_2$ or $R_3$, or both $R_2$ and $R_3$ comprise a radionuclide selected from the group consisting of $^{11}$C, $^{13}$N, $^{15}$O, $^{18}$F, $^{75}$Br, $^{124}$I, $^{125}$I and $^{131}$I. In one variation, Z is

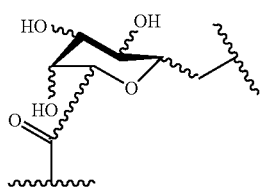

and A is

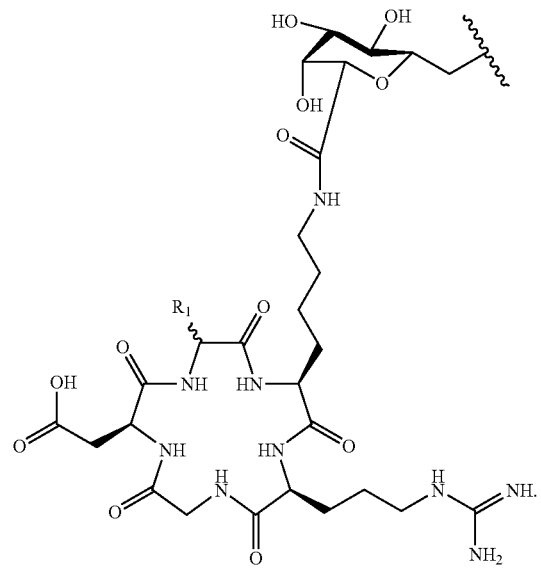

In another variation, Z is

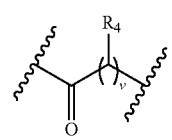

and A is

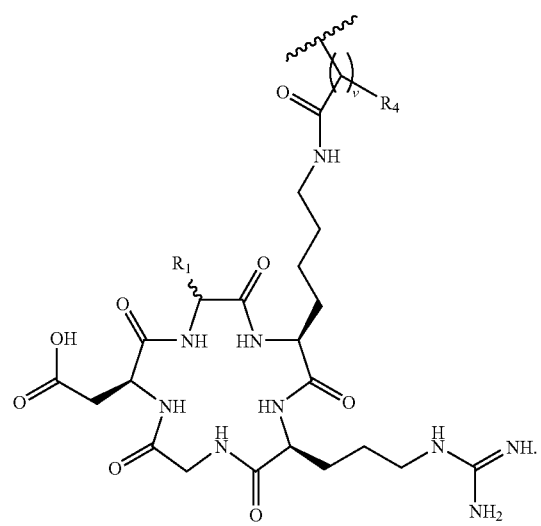

In yet another variation, Z is

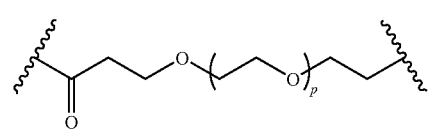

and A is

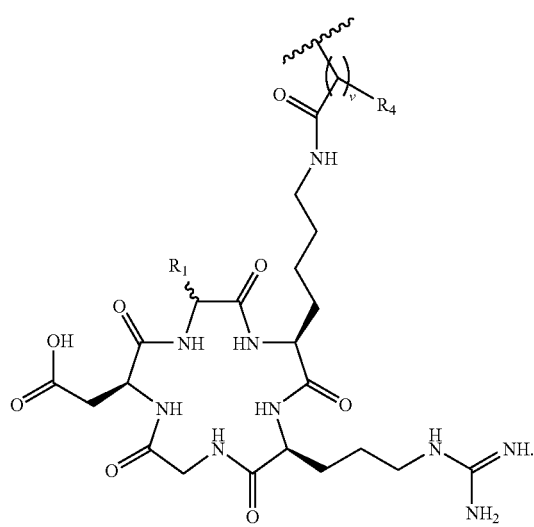

One aspect of the present application is a cyclopeptide of formula II:

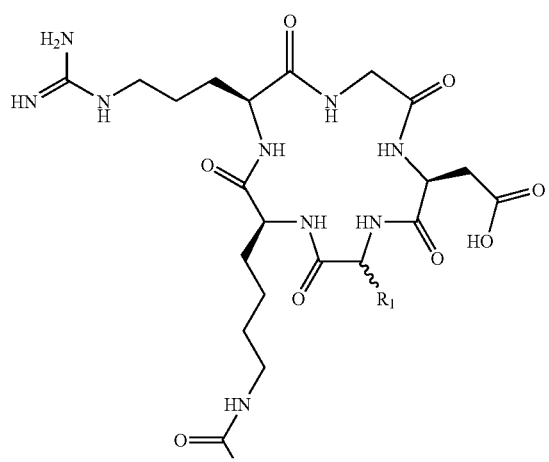

II

-continued

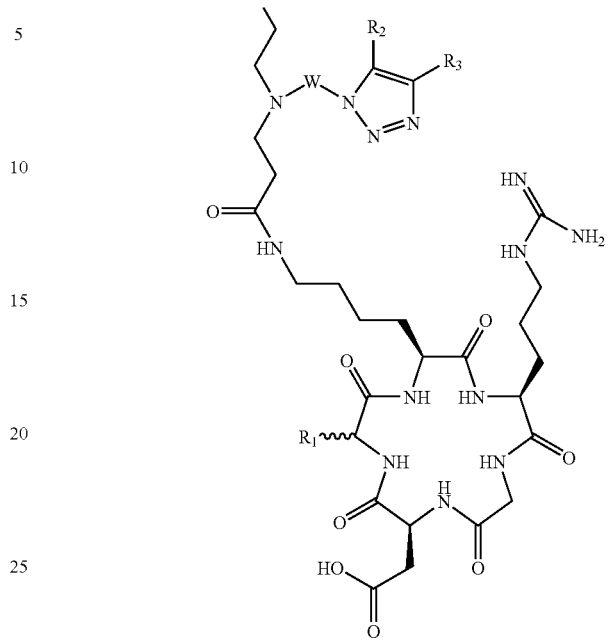

wherein each $R_1$ is independently selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of —H, $C_1$-$C_6$ alkyl, $C_2$-$C_6$ alkenyl, and $C_2$-$C_6$ alkynyl, wherein the alkyl, alkenyl, and alkynyl groups are each optionally substituted, wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{75}Br$, $^{124}I$, $^{125}I$ and $^{131}I$;

W is

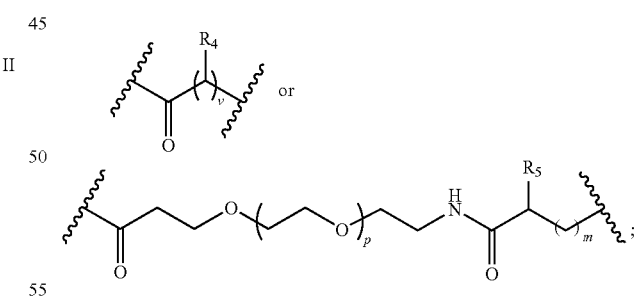

where p is an integer between 0 and 15; v is 0, 1, 2, or 3; m is 0, 1 or 2; each $R_4$ is independently selected from the group consisting of —H, $C_1$-$C_6$ alkyl, $C_2$-$C_6$ alkenyl, and $C_2$-$C_6$ alkynyl, wherein the alkyl, alkenyl, and alkynyl groups are each optionally substituted; and $R_5$ is selected from the group consisting of —H, $C_1$-$C_6$ alkyl, $C_2$-$C_6$ alkenyl, and $C_2$-$C_6$ alkynyl, wherein the alkyl, alkenyl and alkynyl groups are each optionally substituted and wherein the configuration of the chiral center that carries the $R_5$ substituent may be R or S or mixtures thereof.

In yet another embodiment, W is

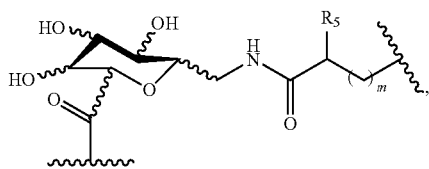

In one embodiment of the any of the disclosed aspects, each $R_1$ is benzyl; $R_2$ is H; $R_3$ is an optionally substituted $C_1$-$C_6$ alkyl comprising a radionuclide selected from the group consisting of $^{11}C$, $^{13}N$, $^{15}O$, $^{18}F$, $^{75}Br$, $^{124}I$, $^{125}I$ and $^{131}I$; and W is

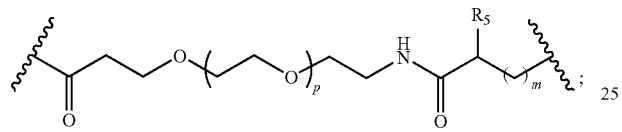

where p is 0, 1, 2, 3, 4 or 5.

Another aspect of the present application is a cyclopeptide of formula III:

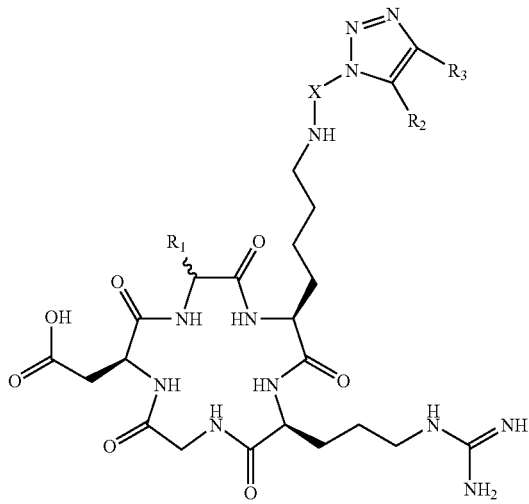

III wherein $R_1$ is selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are optionally substituted;

wherein $R_2$ and $R_3$ are not both H; and either $R_2$ or $R_3$, or both $R_2$ and $R_3$ comprise a radionuclide selected from the group consisting of positron or gamma emitters; and X is a linker comprising a hydrophilic moiety selected from the group consisting of hydroxyl, carbonyl, sulfonamide, sulfonate, phosphate, polar amino acid moiety, PEG moiety, sugar mimetic and sugar moiety.

In one embodiment of any of the aspects disclosed herein, $R_1$ is a side chain of a natural amino acid; $R_2$ is hydrogen; and $R_3$ comprises a radionuclide selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99m}Tc$, $^{75}Br$, $^{153}Gd$ and $^{32}P$. In another embodiment, $R_1$ is benzyl; and $R_3$ comprises a radionuclide selected from the group consisting of $^{11}C$, $^{13}N$, $^{15}O$, $^{18}F$, $^{124}I$, $^{125}I$, $^{131}I$, and $^{75}Br$. In yet another embodiment, $R_1$ is a side chain of a natural amino acid; X is selected from the group consisting of:

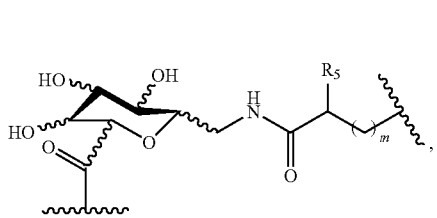

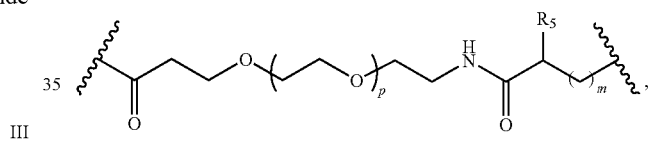

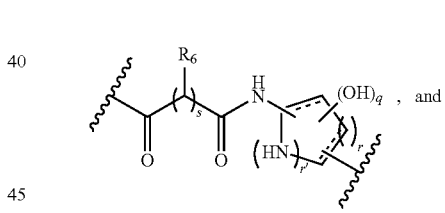

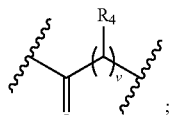

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$- alkoxy-$C_1$-$C_6$-alkyl, wherein the alkyl, alkenyl, alkynyl, alkyloxy, aryl, carbocycle and heterocycle groups are each optionally substituted;

each $R_6$ is independently selected from the group consisting of —H, —OH, $C_1$-$C_6$ alkyl, $C_2$-$C_6$ alkenyl, $C_2$-$C_6$ alkynyl, $C_1$-$C_6$ alkyloxy, aryl-($C_1$-$C_6$ alkylene)-, hydroxy-$C_1$-$C_6$-alkyl, and $C_1$-$C_6$-alkoxy-$C_1$-$C_6$-alkyl, wherein the alkyl, alkenyl, alkynyl, alkyloxy, and aryl-alkylene groups are each optionally substituted;

v is 0, 1, 2, 3, or 4; m is 0, 1, 2, 3 or 4; p is an integer between 1 and 110; q is 1, 2, 3 or 4; r is 1, 2 or 3; r' is 0 or 1; s is 1, 2, 3 or 4; and the radionuclide is selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$; where the configuration of the chiral centers may be R or S or mixtures thereof.

In another embodiment, $R_2$ and $R_3$ are each independently selected from the group consisting of —H, $C_1$-$C_6$ alkyl, $C_2$-$C_6$ alkenyl, and $C_2$-$C_6$ alkynyl, wherein the alkyl, alkenyl, and alkynyl groups are each optionally substituted, wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{75}Br$, $^{124}I$, $^{125}I$, and $^{131}I$; X is

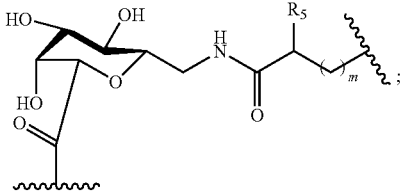

where $R_5$ is selected from the group consisting of —H, $C_1$-$C_6$ alkyl, $C_2$-$C_6$ alkenyl, and $C_2$-$C_6$ alkynyl, wherein the alkyl, alkenyl and alkynyl groups are each optionally substituted and wherein the configuration of the chiral center that carries the $R_5$ substituent may be R or S or mixtures thereof; and m is 0, 1 or 2.

In yet another embodiment, $R_2$ is hydrogen; $R_3$ is selected from the group consisting of $C_1$-$C_4$ alkyl, $C_2$-$C_4$ alkenyl, and $C_2$-$C_4$ alkynyl, wherein the alkyl, alkenyl and alkynyl groups are each optionally substituted, wherein $R_3$ comprises a radionuclide selected from the group consisting of $^{11}C$, $^{13}N$, $^{15}O$, and $^{18}F$; $R_5$ is hydrogen; and m is 0.

In a further embodiment, $R_2$ and $R_3$ are each independently selected from the group consisting of —H, $C_1$-$C_6$ alkyl, $C_2$-$C_6$ alkenyl, $C_2$-$C_6$ alkynyl, wherein the alkyl, alkenyl and alkynyl groups are each optionally substituted; wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{75}Br$, $^{124}I$, $^{125}I$, and 131I; X is

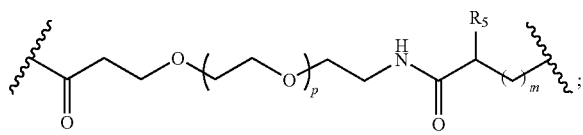

where $R_5$ is selected from the group consisting of —H, $C_1$-$C_6$ alkyl, $C_2$-$C_6$ alkenyl, and $C_2$-$C_6$ alkynyl, wherein the alkyl, alkenyl and alkynyl groups are each optionally substituted and wherein the configuration of the chiral center that carries the $R_5$ substituent may be R or S or mixtures thereof; m is 0, 1, or 2; and p is an integer between 1 and 90.

In still another embodiment, $R_2$ is hydrogen; $R_3$ is selected from the group consisting of $C_1$-$C_4$ alkyl, $C_2$-$C_4$ alkenyl, and $C_2$-$C_4$ alkynyl, wherein the alkyl, alkenyl and alkynyl groups are each optionally substituted, and $R_3$ comprises a radionuclide selected from the group consisting of $^{11}C$, $^{13}N$, $^{15}O$, and $^{18}F$; $R_5$ is hydrogen; m is 0; and p is an integer between 1 and 15.

In another embodiment of any of the aspects disclosed herein, X is

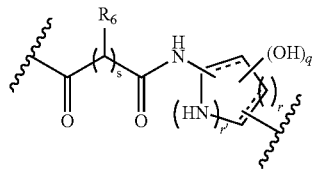

where each $R_6$ is independently selected from the group consisting of —H, —OH, $C_1$-$C_6$ alkyl, $C_2$-$C_6$ alkenyl, $C_1$-$C_6$ alkyloxy, hydroxy-$C_1$-$C_6$-alkyl, and $C_1$-$C_6$-alkoxy-$C_1$-$C_6$-alkyl, wherein the alkyl, alkenyl, and alkyloxy groups are each optionally substituted; q is 2, 3 or 4; r is 2 or 3; r' is 0; and s is 1 or 2.

In yet another embodiment of the present application, X is

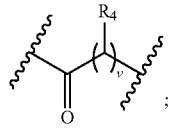

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted; and v is 1, 2, 3, or 4. In one variation, each $R_4$ is independently selected from the group consisting of —H, $C_1$-$C_6$ alkyl, $C_2$-$C_6$ alkenyl, $C_2$-$C_6$ alkynyl, and a PEG moiety, wherein the alkyl, alkenyl, and alkynyl groups are each optionally substituted.

One aspect of the present application is a radiolabeled cyclopeptide of formula IV:

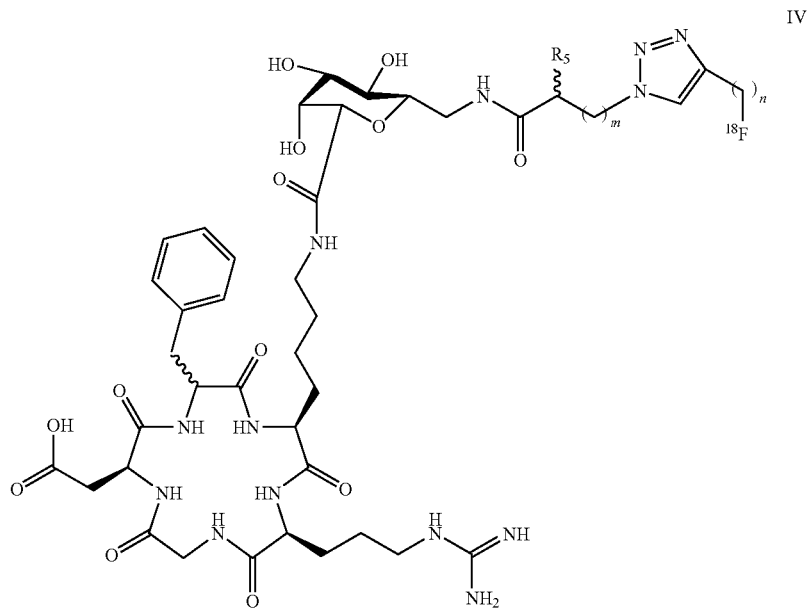

IV wherein: $R_5$ is selected from the group consisting of H, $C_1$-$C_6$ alkyl, $C_2$-$C_6$ alkenyl, $C_2$-$C_6$ alkynyl, $C_1$-$C_6$ alkyloxy, aryl, —($C_1$-$C_6$ alkylene)-aryl, 3- to 7-membered carbocycle, 3- to 7-membered heterocycle, hydroxy-$C_1$-$C_6$-alkyl, and $C_1$-$C_6$-alkoxy-$C_1$-$C_6$-alkyl; wherein the alkyl, alkenyl, alkynyl, alkyloxy, aryl, carbocycle and heterocycle groups are each optionally substituted; wherein the chiral centers attached to ⁓bonds are R or S or mixtures thereof; m is 0, 1, 2, 3 or 4; and n is 1, 2, 3, 4 or 5.

In one embodiment, $R_5$ is selected from the group consisting of H, $C_1$-$C_4$ alkyl, $C_2$-$C_4$ alkenyl, and $C_2$-$C_4$ alkynyl, wherein the alkyl, alkenyl and alkynyl groups are each optionally substituted; wherein the chiral center in the cyclic peptide is R configured and the chiral center bearing the $R_5$ residue is R or S or mixtures thereof; m is 0, 1 or 2; and n is 1, 2, 3 or 4. In another embodiment, $R_5$ is selected from the group consisting of —H, and an optionally substituted $C_1$-$C_4$ alkyl; m is 0 or 1; and n is 2, 3 or 4.

Another aspect of the present application is a radiolabeled cyclopeptide selected from the group consisting of:

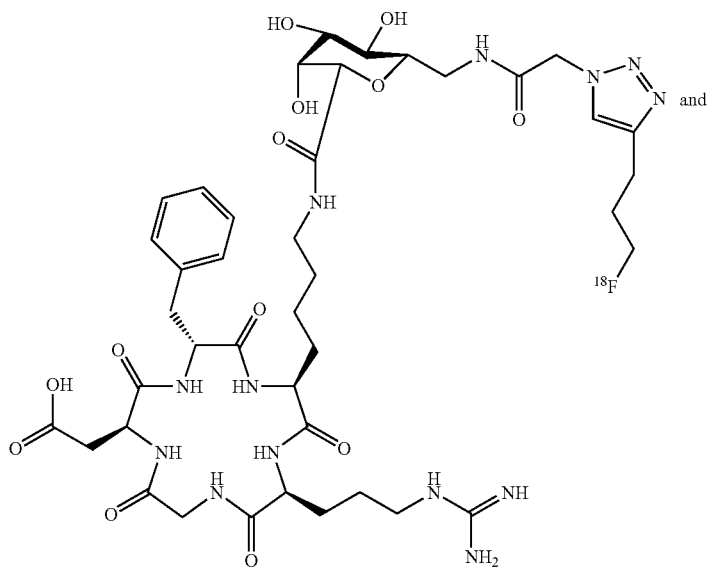

and

-continued

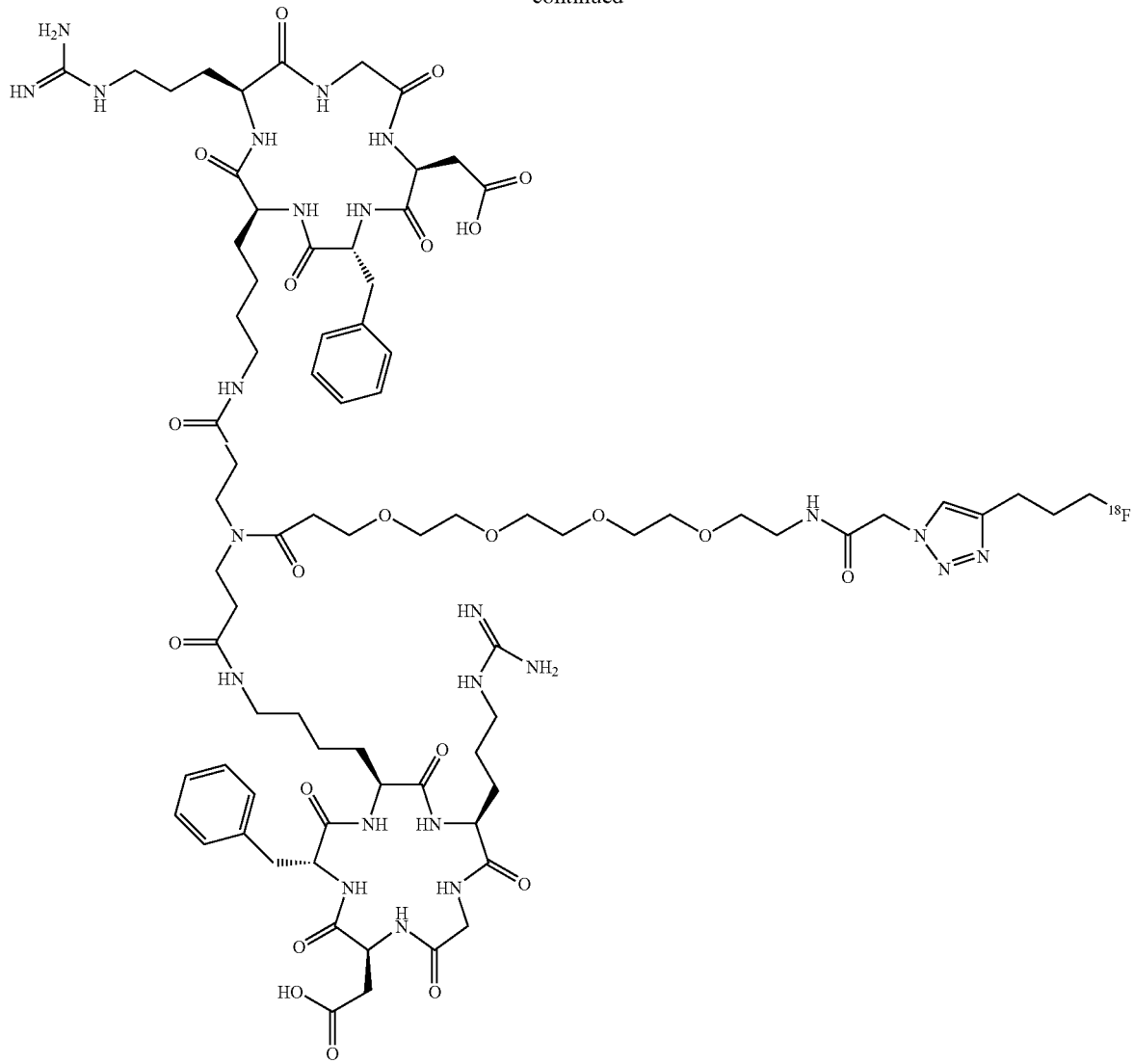

Yet another aspect of the present application is a pharmaceutical composition comprising a radiolabeled cyclopeptide of formula I:

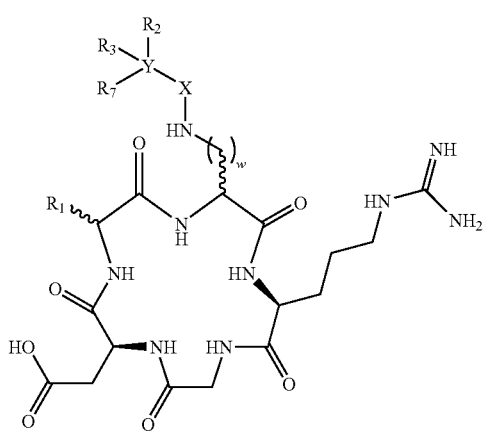

I wherein:

$R_1$ is selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted;

$R_7$ is absent or is selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted; wherein $R_2$, $R_3$ and $R_7$ are not all H;

X is a 5 or 6-membered heterocycle or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

Y is a 5 or 6-membered heterocycle, or a linker comprising a hydrophilic moiety selected from the group consisting of hydroxyl, carbonyl, sulfonamide, sulfonate, phosphate, polar amino acid moiety, PEG moiety, sugar mimetic, and sugar moiety; where at least one of X and Y, but not both X and Y is a 5 or 6-membered heterocycle; and w is 1, 2, 3, 4, or 5; wherein any one of X, Y, $R_2$, $R_3$, and $R_7$ comprises a radionuclide selected from the group consisting of positron or gamma emitters; and a pharmaceutically acceptable carrier.

Yet another aspect of the present application is a pharmaceutical composition comprising a radiolabeled cyclopeptide of formula II or formula III:

II

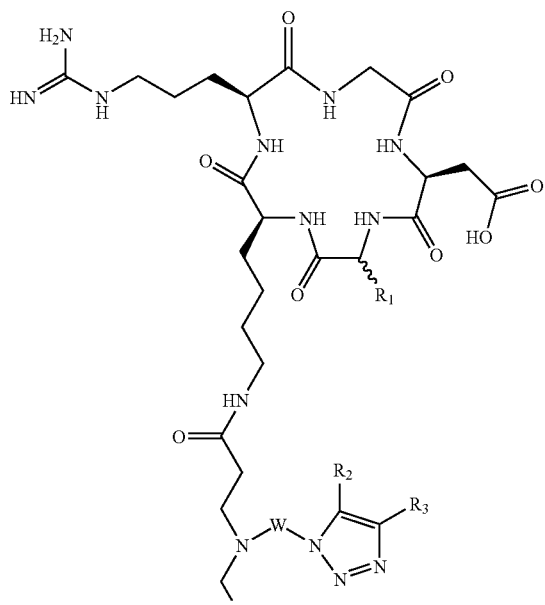

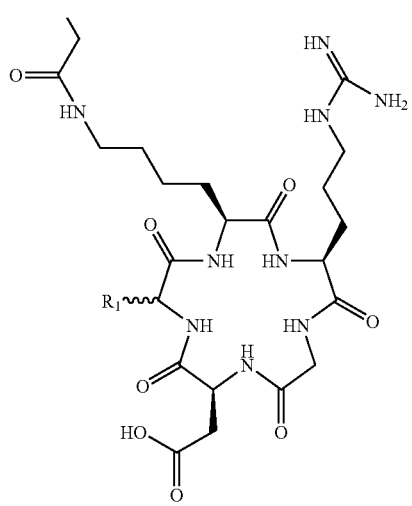

III

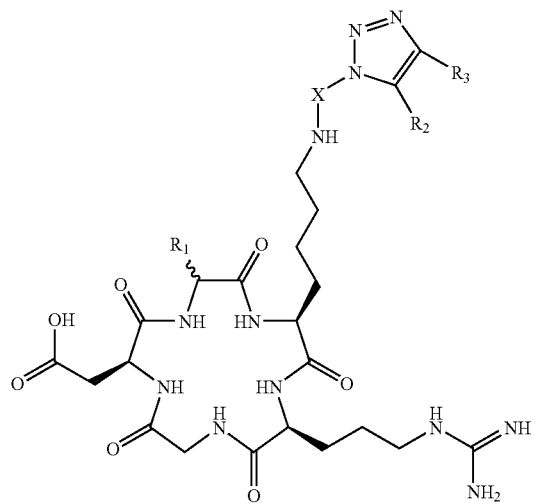

wherein each $R_1$ is independently selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of —H, $C_1$-$C_6$ alkyl, $C_2$-$C_6$ alkenyl, and $C_2$-$C_6$ alkynyl, wherein the alkyl, alkenyl, and alkynyl groups are optionally substituted, wherein $R_2$ and $R_3$ are not both H; and either $R_2$ or $R_3$, or both $R_2$ and $R_3$ comprise a radionuclide selected from the group consisting of $^{11}$C, $^{13}$N, $^{15}$O, $^{18}$F, $^{61}$C, $^{62}$Cu, $^{64}$Cu, $^{67}$Cu, $^{68}$Ga, 124I, $^{125}$I, $^{131}$I, $^{99}$Tc, $^{75}$Br, $^{153}$Gd and $^{32}$P;

each of X and W is selected from the group consisting of:

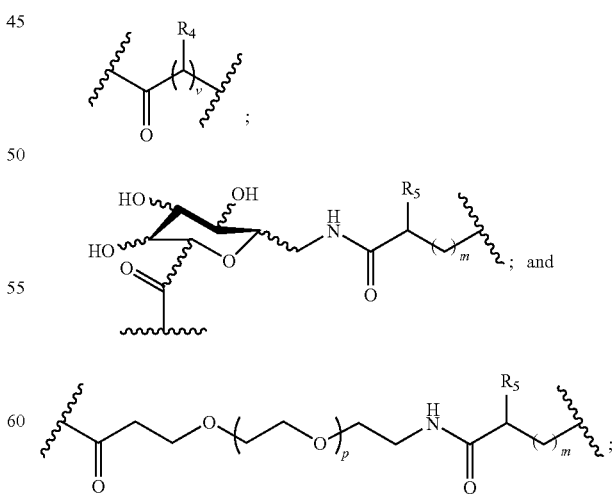

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted; wherein the configuration of the chiral centers may be R or S or mixtures thereof; v is 0, 1, 2, 3, or 4; m is 0, 1, 2, 3 or 4; and p is an integer between 1 and 25; and a pharmaceutically acceptable carrier.

Still another aspect of the present application is a pharmaceutical composition comprising a radiolabeled cyclopeptide selected from the group consisting of:

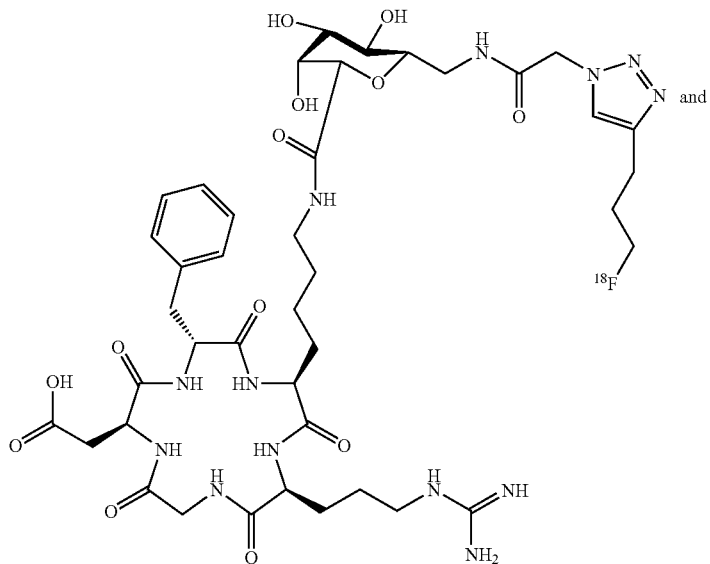

and

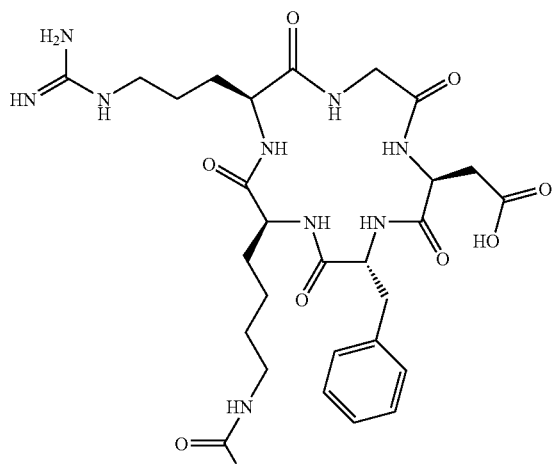

-continued

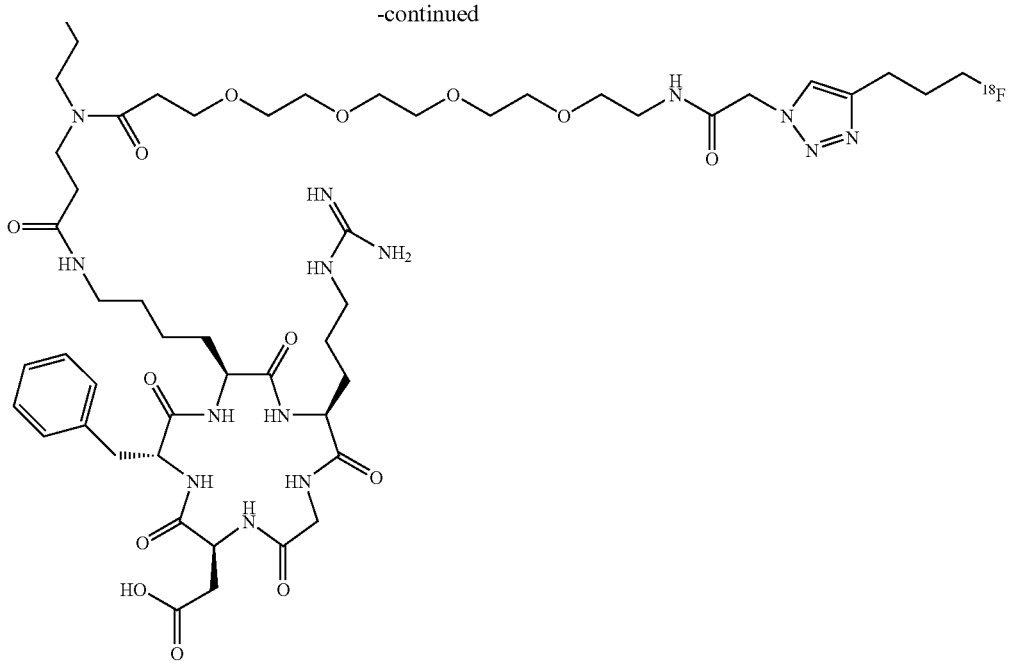

and a pharmaceutically acceptable carrier.

One aspect of the present application is a method of monitoring the level of integrin $\alpha_v\beta_3$ or visualizing integrin $\alpha_v\beta_3$ expression within a body of a patient, the method comprising: (a) administering to the patient a radiolabeled cyclopeptide; and (b) employing a nuclear imaging technique selected from the group consisting of positron emission tomography (PET) and single photon emission computed tomography (SPECT) for monitoring or visualizing a distribution of the radiolabeled cyclopeptide within the body or within a portion thereof; wherein the radiolabeled cyclopeptide is of formula I:

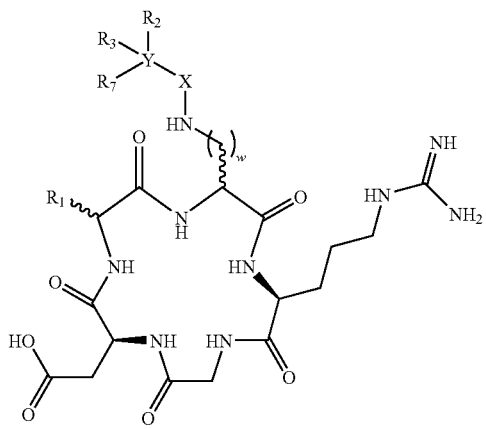

wherein $R_1$ is selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted;

$R_7$ is absent or is selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted; wherein $R_2$, $R_3$ and $R_7$ are not all H;

X is a 5 or 6-membered heterocycle or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

Y is a 5 or 6-membered heterocycle, or a linker comprising a hydrophilic moiety selected from the group consisting of hydroxyl, carbonyl, sulfonamide, sulfonate, phosphate, polar amino acid moiety, PEG moiety, sugar mimetic, and sugar moiety; where at least one of X and Y, but not both X and Y is a 5 or 6-membered heterocycle; and w is 1, 2, 3, 4, or 5; wherein any one of X, Y, $R_2$, $R_3$, and $R_7$ comprises a radionuclide selected from the group consisting of positron or gamma emitters.

Another aspect of the present application is a method of monitoring the level of integrin $\alpha_v\beta_3$ or visualizing integrin $\alpha_v\beta_3$ expression within a body of a patient, the method comprising: (a) administering to the patient a radiolabeled cyclopeptide; and (b) employing a nuclear imaging technique selected from the group consisting of positron emission tomography (PET) and single photon emission computed tomography (SPECT) for monitoring or visualizing a distribution of the radiolabeled cyclopeptide within the body or within a portion thereof; wherein the radiolabeled cyclopeptide is of formula II or formula III:

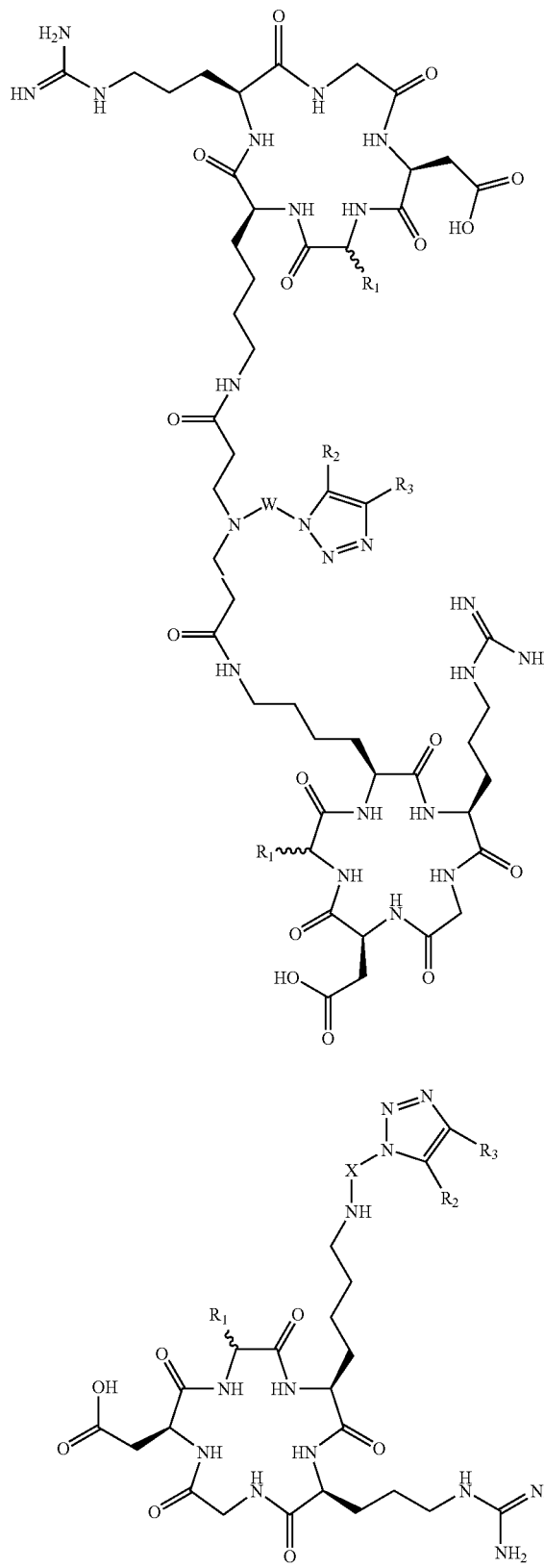

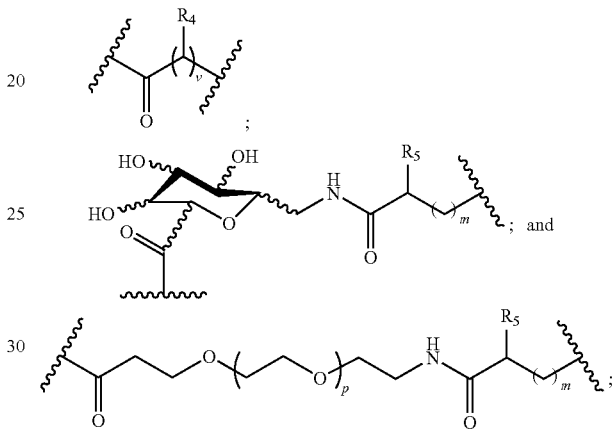

wherein each $R_1$ is independently selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of —H, $C_1$-$C_6$ alkyl, $C_2$-$C_6$ alkenyl, and $C_2$-$C_6$ alkynyl, wherein the alkyl, alkenyl, and alkynyl groups are optionally substituted, wherein $R_2$ and $R_3$ are not both H; and either $R_2$ or $R_3$, or both $R_2$ and $R_3$ comprise a radionuclide selected from the group consisting of $^{11}$C, $^{13}$N, $^{15}$O, $^{18}$F, $^{61}$Cu, $^{62}$Cu, $^{64}$Cu, $^{67}$Cu, $^{68}$Ga, $^{124}$I, $^{125}$I, $^{131}$I, $^{99}$Tc, $^{75}$Br, $^{153}$Gd and $^{32}$P;

each of X and W is selected from the group consisting of:

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted;

wherein the configuration of the chiral centers may be R or S or mixtures thereof; v is 0, 1, 2, 3, or 4; m is 0, 1, 2, 3 or 4; and p is an integer between 1 and 25.

Yet another aspect of the present application is a method of monitoring the level of integrin $\alpha_v\beta_3$ or visualizing integrin $\alpha_v\beta_3$ expression within a body of a patient, the method comprising: (a) administering to the patient a radiolabeled cyclopeptide; and (b) employing a nuclear imaging technique selected from the group consisting of positron emission tomography (PET) and single photon emission computed tomography (SPECT) for monitoring or visualizing a distribution of the radiolabeled cyclopeptide within the body or within a portion thereof; wherein the radiolabeled cyclopeptide is selected from the group consisting of:

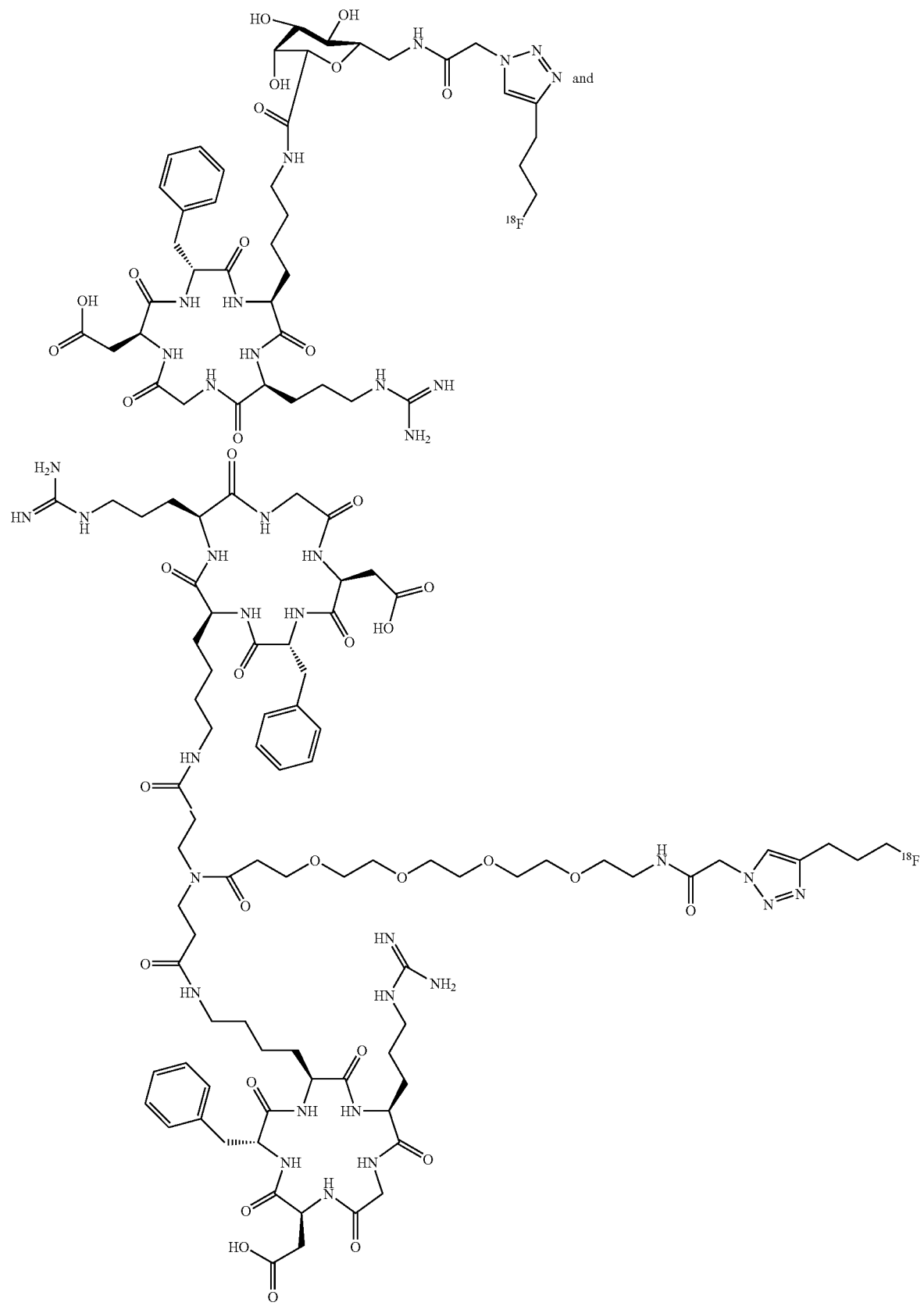

A still further aspect of the present application is a method for imaging of blood vessel growth in solid tumors based on expression of integrin $\alpha_v\beta_3$ within the body of a patient, the method comprising: (a) administering to the patient a radiolabeled cyclopeptide; (b) employing a nuclear imaging technique selected from the group consisting of positron emission tomography (PET) and single photon emission computed tomography (SPECT) for imaging a distribution of the radiolabeled cyclopeptide within the body or within a portion thereof; and c) correlating the distribution of the radiolabeled cyclopeptide to the growth of blood vessels in solid tumors, wherein the radiolabeled cyclopeptide is of formula I:

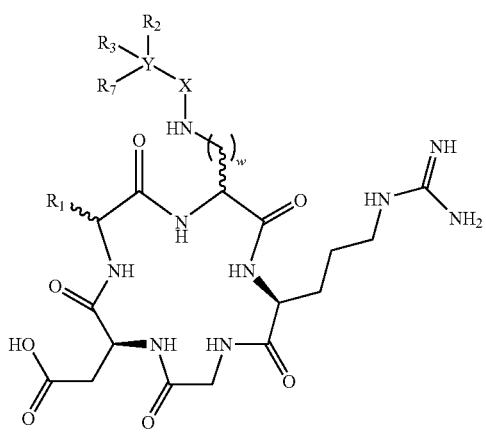

I wherein:

$R_1$ is selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted;

$R_7$ is absent or is selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted; wherein $R_2$, $R_3$ and $R_7$ are not all H;

X is a 5 or 6-membered heterocycle or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

Y is a 5 or 6-membered heterocycle, or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

where at least one of X and Y, but not both X and Y is a 5 or 6-membered heterocycle; and w is 1, 2, 3, 4, or 5; wherein any one of X, Y, $R_2$, $R_3$, and $R_7$ comprises a radionuclide selected from the group consisting of positron or gamma emitters.

Yet another aspect of the present application is a method for imaging of blood vessel growth in solid tumors based on expression of integrin $\alpha_v\beta_3$ within the body of a patient, the method comprising: (a) administering to the patient a radiolabeled cyclopeptide; (b) employing a nuclear imaging technique selected from the group consisting of positron emission tomography (PET) and single photon emission computed tomography (SPECT) for imaging a distribution of the radiolabeled cyclopeptide within the body or within a portion thereof; and c) correlating the distribution of the radiolabeled cyclopeptide to the growth of blood vessels in solid tumors, wherein the radiolabeled cyclopeptide is of formula II or formula III:

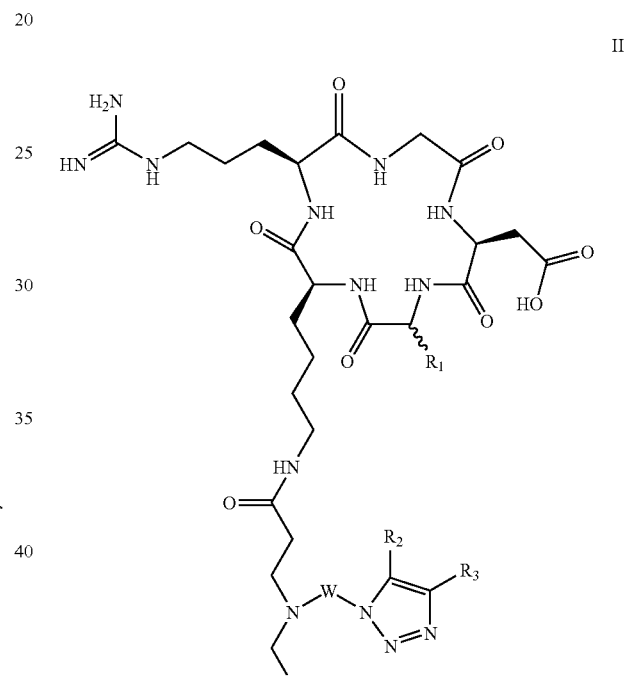

II

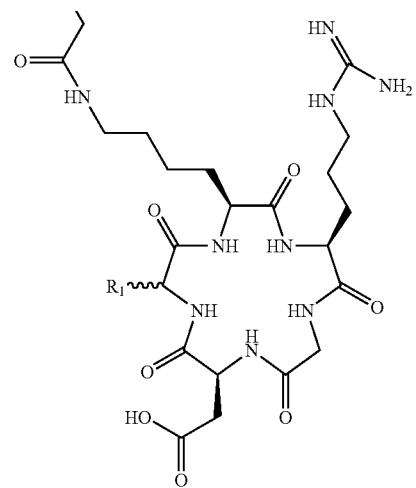

-continued

III

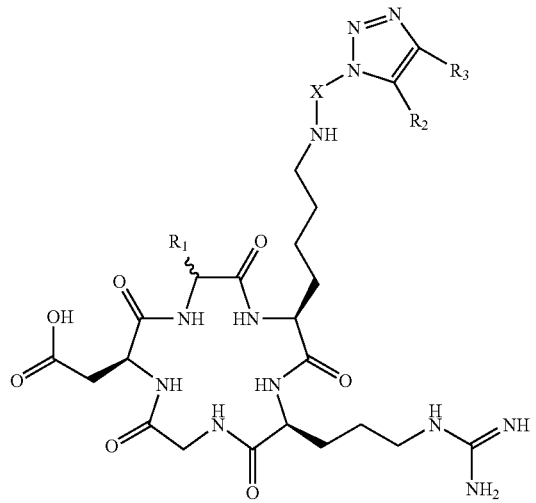

wherein each $R_1$ is independently selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of —H, $C_1$-$C_6$ alkyl, $C_2$-$C_6$ alkenyl, and $C_2$-$C_6$ alkynyl, wherein the alkyl, alkenyl, and alkynyl groups are optionally substituted, wherein $R_2$ and $R_3$ are not both H; and either $R_2$ or $R_3$, or both $R_2$ and $R_3$ comprise a radionuclide selected from the group consisting of $^{11}$C, $^{13}$N, $^{15}$O, $^{18}$F, $^{61}$Cu, $^{62}$Cu, $^{64}$Cu, $^{67}$Cu, $^{68}$Ga, $^{124}$I, $^{125}$I, $^{131}$I, $^{99}$Tc, $^{75}$Br, $^{153}$Gd and $^{32}$P;

each of X and W is selected from the group consisting of:

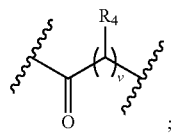

-continued

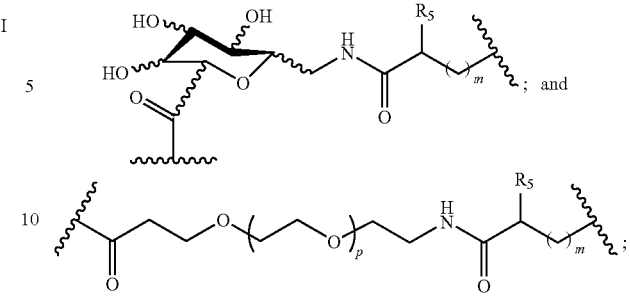

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted;

wherein the configuration of the chiral centers may be R or S or mixtures thereof; v is 0, 1, 2, 3, or 4; m is 0, 1, 2, 3 or 4; and p is an integer between 1 and 25.

Yet another aspect of the present application is a method for imaging of blood vessel growth in solid tumors based on expression of integrin $\alpha_v\beta_3$ within the body of a patient, the method comprising: (a) administering to the patient a radiolabeled cyclopeptide; (b) employing a nuclear imaging technique selected from the group consisting of positron emission tomography (PET) and single photon emission computed tomography (SPECT) for imaging a distribution of the radiolabeled cyclopeptide within the body or within a portion thereof; and c) correlating the distribution of the radiolabeled cyclopeptide to the growth of blood vessels in solid tumors, wherein the radiolabeled cyclopeptide is selected from the group consisting of:

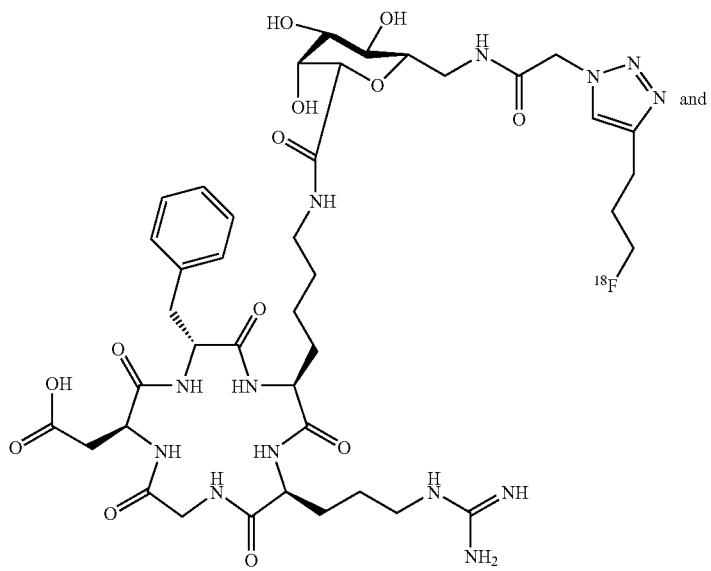

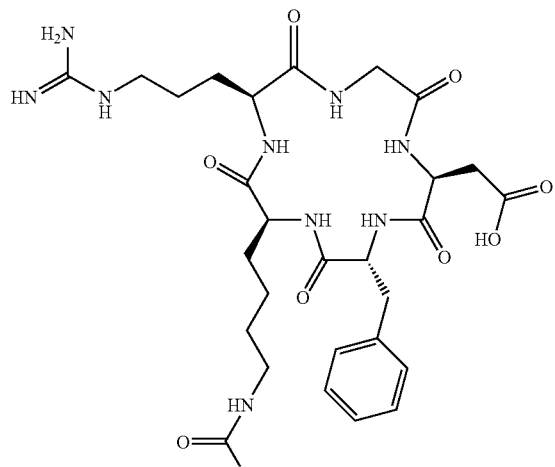
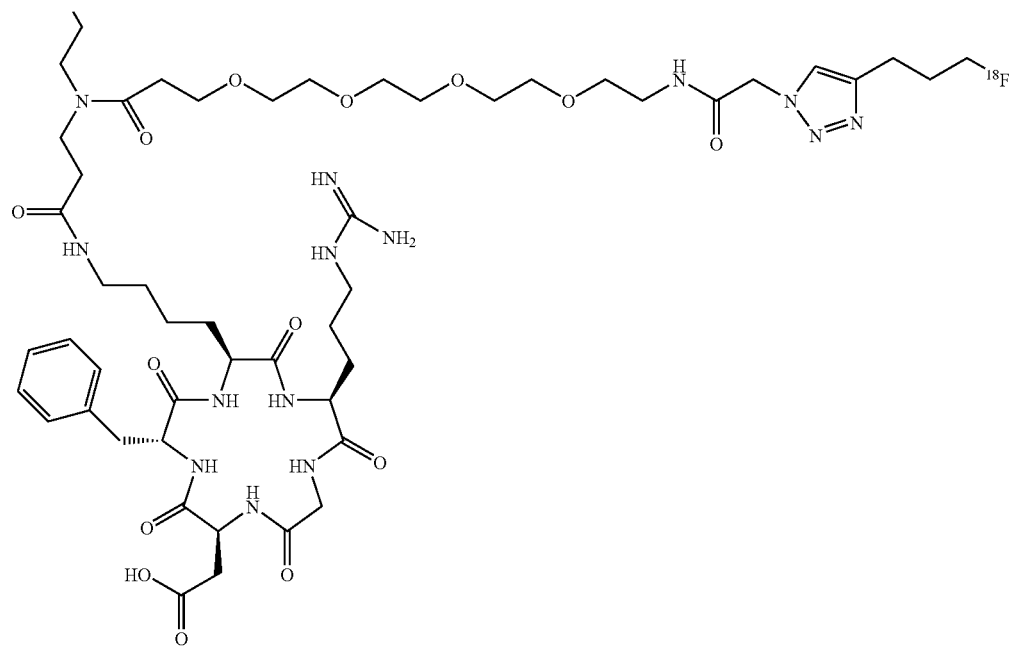

One aspect of the present invention is a compound of formula V:

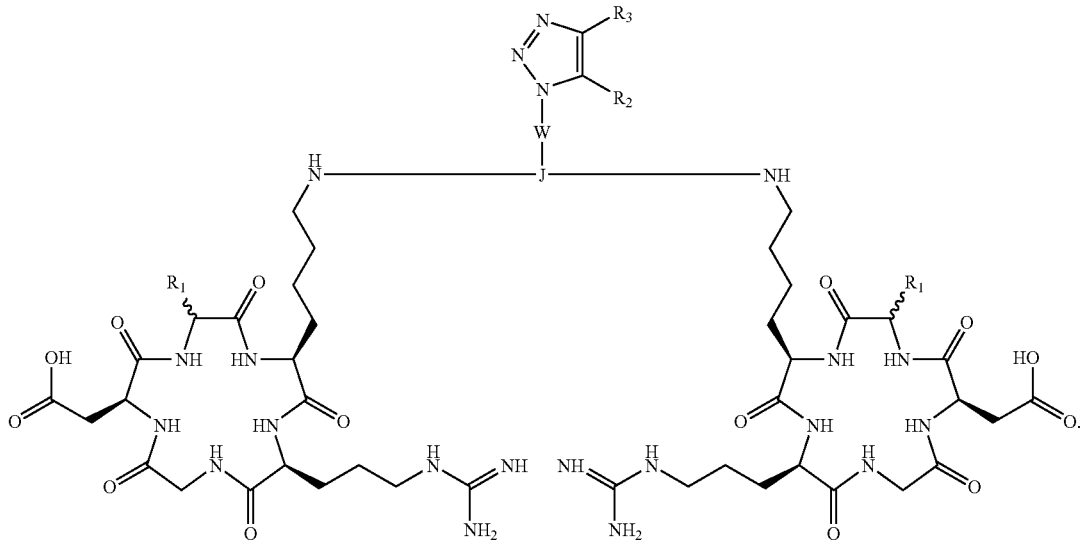

wherein each $R_1$ is independently selected from the group consisting of a side chain of a natural amino acid and a side chain of an unnatural amino acid, wherein the natural amino acid and the unnatural amino acid is either in the D or L form; $R_2$ and $R_3$ are each independently selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl, carbocycle and heterocycle groups are each optionally substituted; wherein $R_2$ and $R_3$ are not both H; and either $R_2$ or $R_3$, or both $R_2$ and $R_3$ comprise a radionuclide selected from the group consisting of positron or gamma emitters; W is a linker comprising zero, one or more moieties selected from the group consisting of hydroxyl, carbonyl, sulfonamide, sulfonate, phosphate, polar amino acid moiety, PEG moiety, sugar mimetic, and a sugar moiety; J is a linker comprising a moiety selected from the group consisting of $C_1$-$C_6$ alkyl, —$C_1$-$C_6$ alkenyl, —$C_1$-$C_6$ alkynyl, aryl, aryl-($C_1$-$C_6$ alkylene)-, 3- to 7-membered carbocycle, 3- to 7-membered heterocycle, and natural amino acids wherein the alkyl, alkenyl, alkynyl, aryl, carbocycle, heterocycle groups are each optionally substituted. In one aspect, the radionuclide is selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$, and $^{32}P$; W is selected from the group consisting of

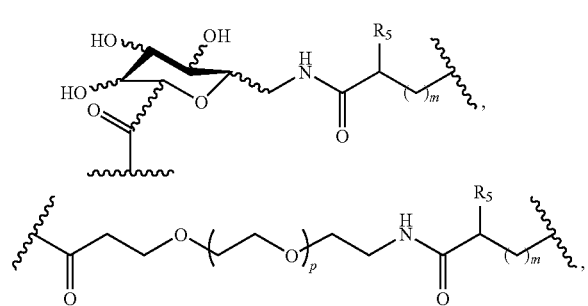

-continued

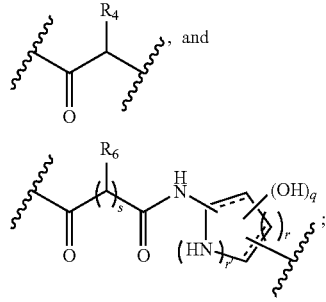

where $R_4$ is independently —H, —C, —$C_6$ alkyl, C, —$C_6$ alkenyl, $C_1$-$C_6$ alkynyl, $C_1$-$C_6$ alkyloxy, aryl, aryl-($C_1$-$C_6$ alkylene)-, $C_3$-$C_7$ carbocycle, 3- to 7-membered heterocycle, hydroxy-$C_1$-$C_6$-alkyl, $C_1$-$C_6$-alkoxy-$C_1$-$C_6$-alkyl, and a PEG moiety, $R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle and heterocycle groups are each optionally substituted; each $R_6$ is independently selected from the group consisting of —H, —OH, $C_1$-$C_6$ alkyl, $C_2$-$C_6$ alkenyl, $C_2$-$C_6$ alkynyl, $C_1$-$C_6$ alkyloxy, aryl-($C_1$-$C_6$ alkylene)-, hydroxy-$C_1$-$C_6$-alkyl, and $C_1$-$C_6$-alkoxy-$C_1$-$C_6$-alkyl, wherein the alkyl, alkenyl, alkynyl, alkyloxy, and aryl-alkylene groups are each optionally substituted; p is an integer between 0 and 15; q is 1, 2, 3 or 4; r is 1, 2 or 3; r' is 0 or 1; s is 1, 2, 3 or 4; and m is 0, 1, 2, 3, 4 or 5; wherein the configuration of any of the chiral centers may optionally be R or S. In another embodiment, J is

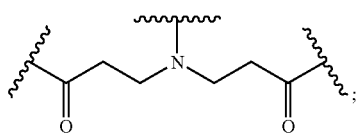
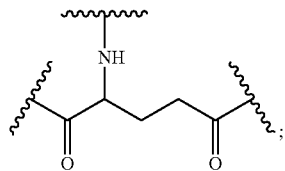
and the radionuclide is selected from the group consisting of $^{11}C$, $^{13}N$, $^{15}O$, $^{18}F$, $^{124}I$, $^{125}I$, $^{131}I$, and $^{75}Br$. In yet another embodiment, J is
and the radionuclide is selected from the group consisting of $^{11}C$, $^{13}N$, $^{15}O$, $^{18}F$, $^{124}I$, $^{125}I$, $^{131}I$, and $^{75}Br$.
One aspect of the present invention is a compound of formula VI
VI
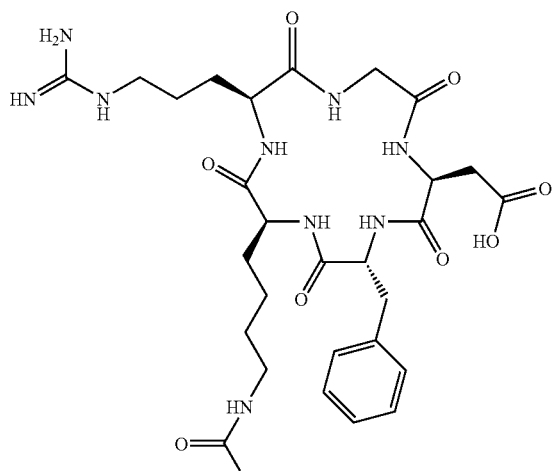
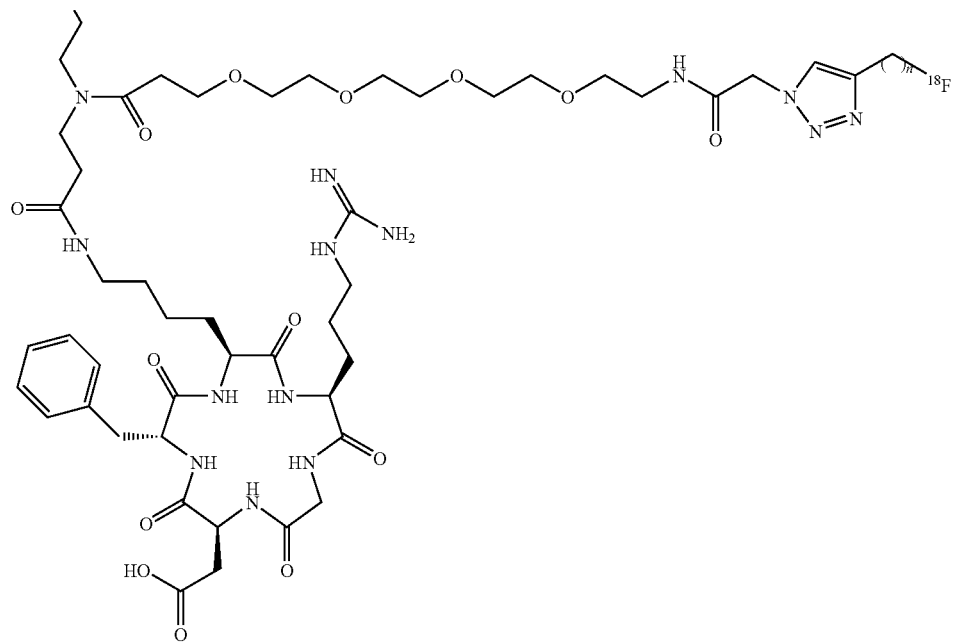

wherein m is 0 to 4, and n is 1-5. In one aspect, m is 0 and n is 3.

One aspect of the present application is a pharmaceutical composition comprising any of the above disclosed compounds and a pharmaceutically acceptable carrier. In one aspect of the present application the compounds disclosed herein can be used as tracers in Positron Emission Tomography (PET) or Single Photon Emission Computed Tomography (SPECT).

One aspect of the present application is a method of monitoring the level of integrin receptor within a body of a patient, the method comprising: (a) administering to the patient any of the above cited radiolabeled cyclopeptides, and (b) employing a nuclear imaging technique selected from the group consisting of positron emission tomography (PET) and single photon emission computed tomography (SPECT) for monitoring a distribution of the cyclic polypeptide within the body or within a portion thereof. In one embodiment, the integrin receptor is $\alpha_v\beta_3$.

Another aspect of the present application is a method of visualizing integrin expression within a body of a patient, the method comprising: (a) administering to the patient any of the above cited radiolabeled cyclopeptides; and (b) employing a nuclear imaging technique selected from the group consisting of positron emission tomography (PET) and single photon emission computed tomography (SPECT) for visualizing a distribution of the radiolabeled cyclopeptide within the body or within a portion thereof. In one embodiment, the integrin receptor is $\alpha_v\beta_3$.

Another aspect of the present application is a method for imaging of blood vessel growth in solid tumors based on expression of integrin $\alpha_v\beta_3$ within the body of a patient, the method comprising: (a) administering to the patient any of the above cited the radiolabeled cyclopeptides; (b) employing a nuclear imaging technique selected from the group consisting of positron emission tomography (PET) and single photon emission computed tomography (SPECT) for imaging a distribution of the radiolabeled cyclopeptide within the body or within a portion thereof; and c) correlating the distribution of the radiolabeled cyclopeptide to the growth of blood vessels in solid tumors. In one embodiment, the integrin receptor is $\alpha_v\beta_3$.

The integrin $\alpha_v\beta_3$ plays an important role in regulating tumor growth and angiogenesis. The non-invasive visualization and quantification of $\alpha_v\beta_3$ integrin levels in patients enables a variety of applications. One such application is determination of $\alpha_v\beta_3$ levels before therapy with $\alpha_v\beta_3$ antagonists. Patients with low or no $\alpha_v\beta_3$ expression might not benefit from $\alpha_v\beta_3$ antagonist therapy and could then receive alternate treatment. Patients with $\alpha_v\beta_3$ positive lesions could have their treatment optimized, based on the use of the compounds of the present application to evaluate inhibition of the $\alpha_v\beta_3$ integrin.

Pharmaceutical compositions of the compounds of this application, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, 5% dextrose in water or buffered sodium or ammonium acetate solution. Such formulations are especially suitable for parenteral administration but may also be used for oral administration. Excipients, such as polyvinylpyrrolidinone, gelatin, hydroxycellulose, acacia, polyethylene glycol, mannitol, sodium chloride, or sodium citrate, may also be added. Alternatively, these compounds may be encapsulated, tableted, or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols, or water. Solid carriers include starch, lactose, calcium sulfate, dihydrate, terra alba, magnesium stearate or stearic acid, talc, pectin, acacia, agar, or gelatin. The carrier may also include a sustained release material such as glyceryl monostearate or glyceryl distearate, alone or with a wax. The pharmaceutical preparations are made following the conventional techniques of pharmacy involving milling, mixing, granulation, and compressing, when necessary, for tablet forms; or milling, mixing, and filling for hard gelatin capsule forms. When a liquid carrier is used, the preparation may be in the form of a syrup, elixir, emulsion, or an aqueous or non-aqueous suspension. Such a liquid formulation may be administered directly p.o. or filled into a soft gelatin capsule. Suitable formulations for each of these methods of administration may be found in, for example, REMINGTON: THE SCIENCE AND PRACTICE OF PHARMACY, A. Gennaro, ed., 20th edition, Lippincott, Williams & Wilkins, Philadelphia, Pa.

The pharmaceutical compositions of the application may be in the form of a sterile injectable preparation. Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents.

EXAMPLES

The novel cyclopeptide analogs presented in this application are prepared using click chemistry [10-18]. Click chemistry, as used in this application, describes the rapid, selective and specific formation of 1,4- or 1,5-disubstituted 1,2,3-triazoles starting from alkyl azides and terminal alkynes. One or more triazole moieties are attached to the cyclic peptide, the hydrophilic linker, or the radiolabel tag. Click chemistry is a high-yielding and modular approach and as such, the pharmacokinetic properties of these cyclopeptide analogs are easily modified.

Scheme I demonstrates an exemplary reaction scheme for the synthesis of a cyclohexane based galactose mimic. 1,4-Cyclohexadiene is mono-epoxidized using one equivalent of m-chloroperoxybenzoic acid. Sodium azide, in a buffered ammonium chloride solution, is used to open the mono-epoxide. The remaining alkene is epoxidized using t-butyl hydroperoxide, along with a catalytic amount of vanadyl acetylacetonate, to form the epoxide. Ring opening of the second epoxide with ammonia results in an azido, amino, dihydroxyl substituted cyclohexane ring. Alternatively, the epoxide can be opened with a variety of nucleophiles in order to install the desired functionality. This method can be adapted to the labeling of any cyclic RGD peptide that contains one lysine.

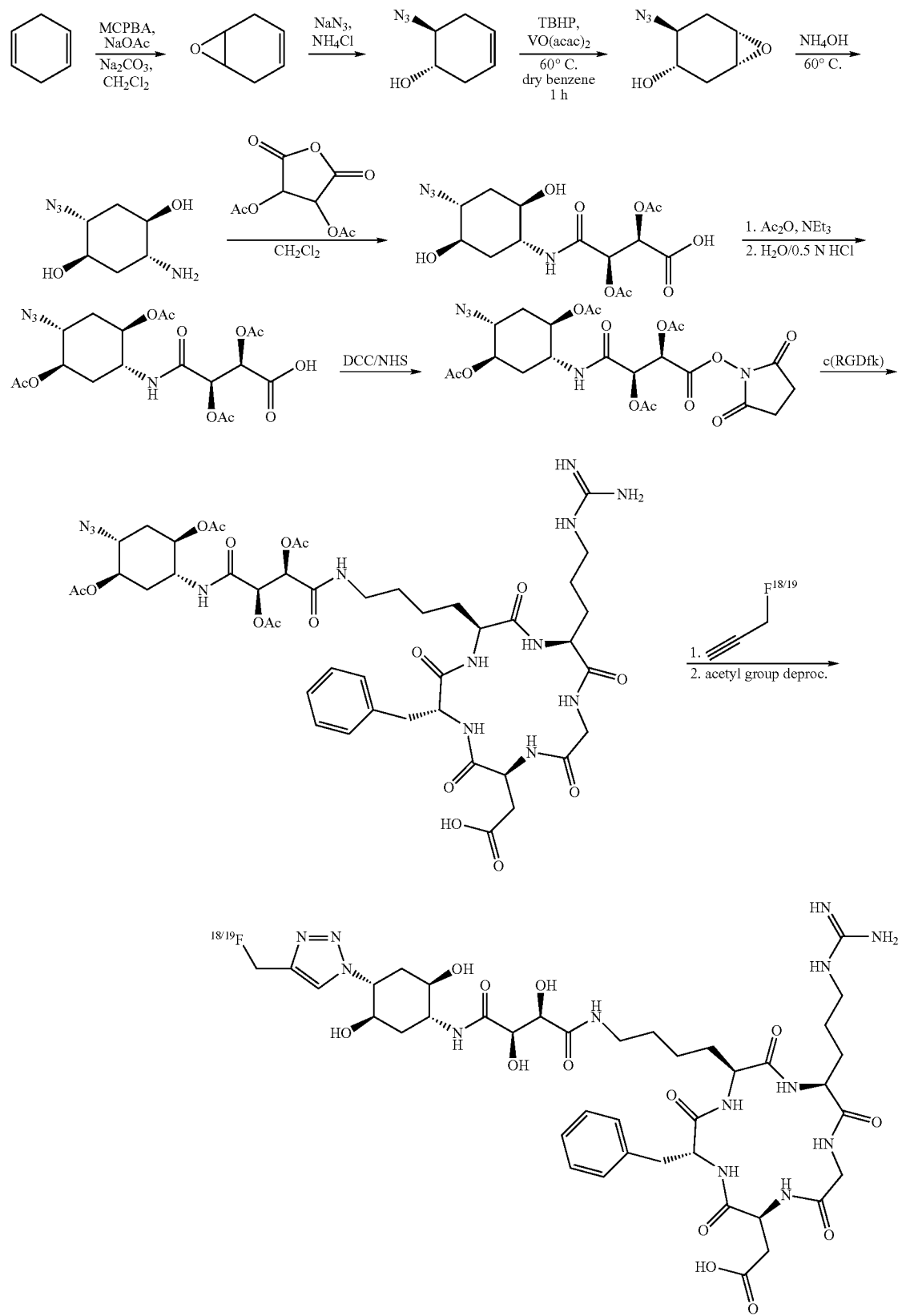

Scheme II shows an exemplary reaction scheme for the synthesis of a compound incorporating a ring-opened sugar moiety as tether for the radionuclide to the triazole ring. A Wittig type reaction on 5-O-trityl-D-ribofuranose affords the expected olefin. The reaction of the olefin with an excess of n-butyllithium provides the corresponding acetylene compound, which is then protected with acetyl groups. Removal of the trityl group, followed by tosylation of the resulting hydroxyl group, affords the [$^{18}$F]-labeling precursor. Fluorination of the tosylated precursor is followed by click reaction with cyclic RGD-containing peptide, which has been conjugated with acetyl-protected serine azide, to afford the final product.

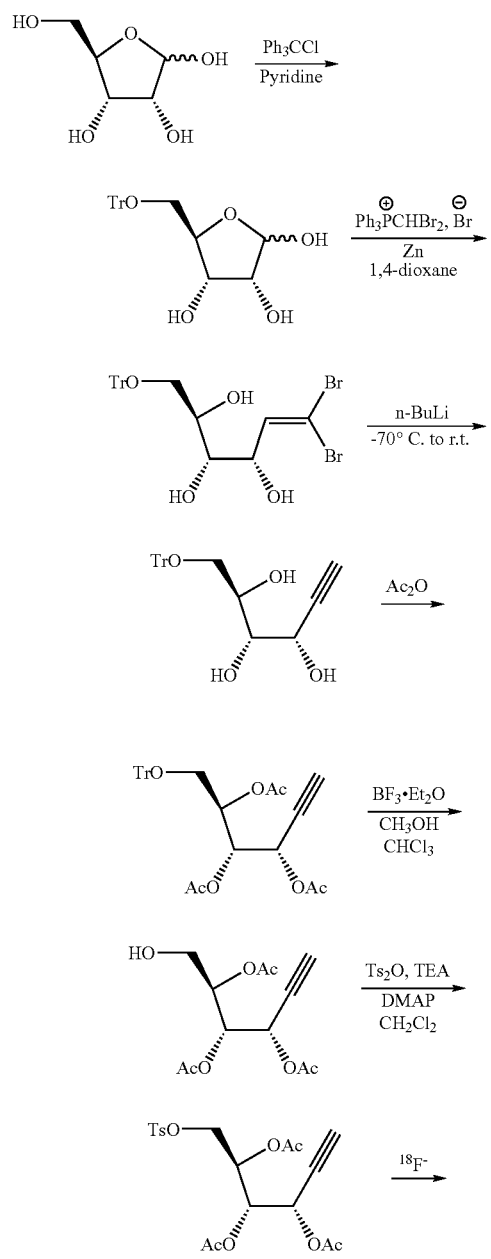

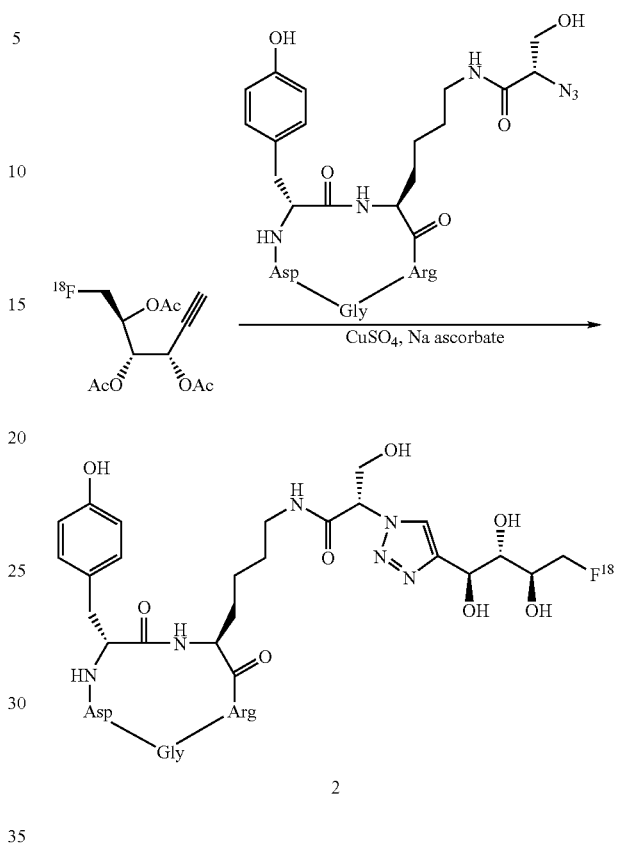

An exemplary preparation of one of the cyclic RGD peptide derivatives of the present application, Compound 7, is shown in Scheme III.

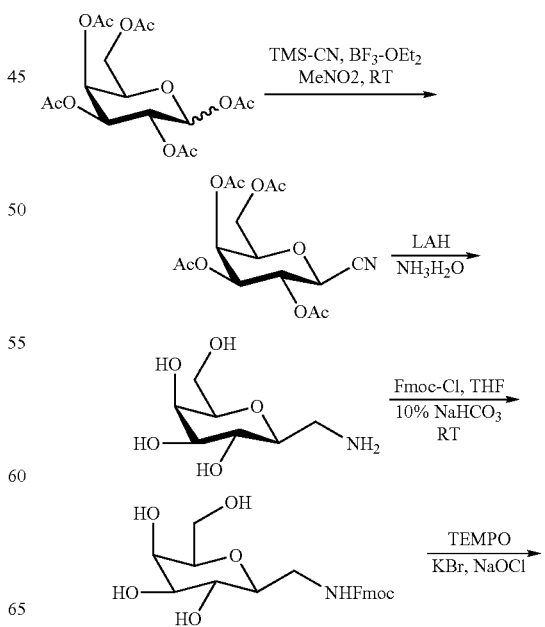

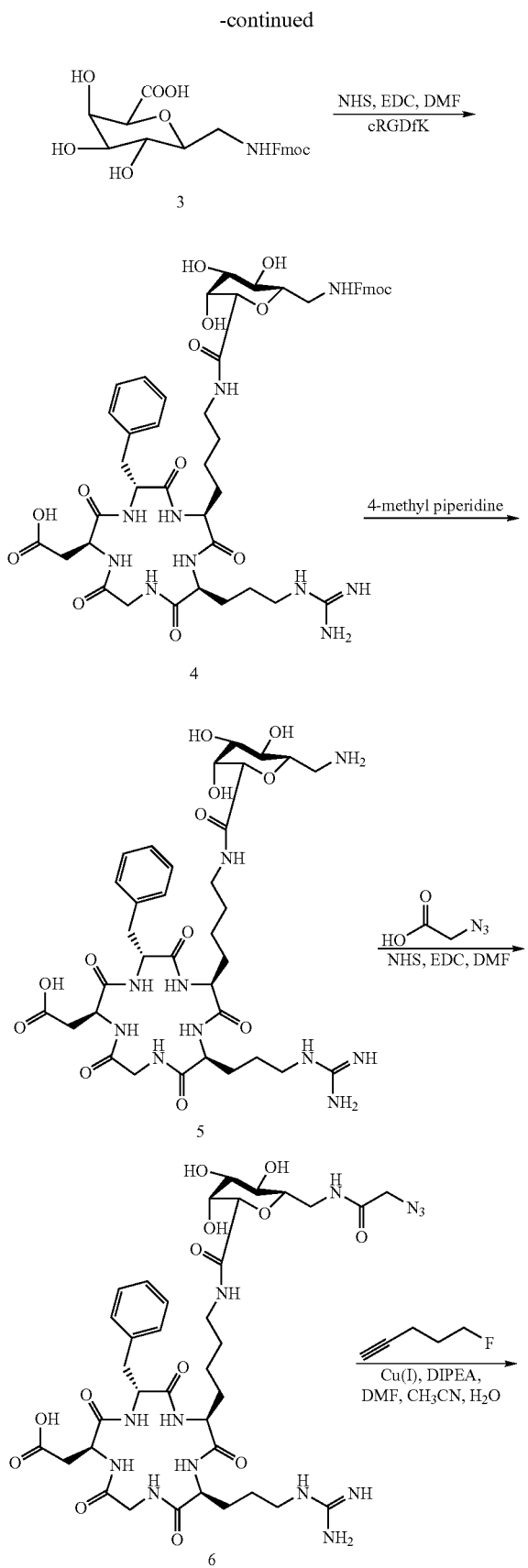

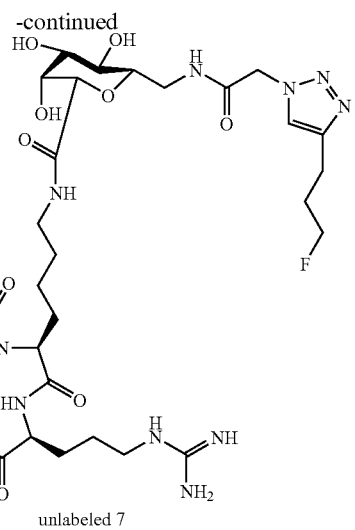

unlabeled 7

Synthesis of Compound 7:

Synthesis of Compound 4: 6-((((9H-Fluoren-9-yl)methoxy)carbonylamino)-methyl)-3,4,5-trihydroxytetrahydro-2H-pyran-2-carboxylic acid (3) [Ref. 6] (44.46 mg, 0.104 mmol) was dissolved in N,N'-dimethylformamide (DMF) (2 mL) and treated with N-hydroxysuccinimide (NHS) (12 mg, 0.104 mmol) and N-(3-dimethylaminopropyl)-N'-ethylcarbodiimide hydrochloride (EDC) (19.9 mg, 0.104 mmol) at room temperature. After stirring for 1 hr, a solution of c(RGDfK) (50 mg, 0.083 mmol) in DMF (1 mL) and N,N'-di-isopropylethylamine (DIPEA) (20 μL, 0.115 mmol) were added to the reaction mixture and stirred for 6 hr. LCMS showed all the starting material was consumed. Solvent was removed under high vacuum and the residue was dissolved in water (10 mL) and methanol (2 mL). After filtration, the desired product was isolated by semi-preparative HPLC. The collected fractions were combined and lyophilized to afford compound 4 (36 mg, 43%) as a white fluffy powder. MS (m/z) (ESI): 1015.4 $[M+H]^+$.

Synthesis of Compound 5: Compound 4 (36 mg, 0.035 mmol) was treated with 20% piperidine in DMF (5 ml) for 2 hr at room temperature. After removing the solvent under high vacuum, the residue was dissolved in water (5 mL). After filtration, the desired product was isolated by semi-preparative HPLC. The collected fractions were combined and lyophilized to afford compound 5 (25 mg, 90%) as a white fluffy powder. MS (m/z) (ESI): 793.3 $[M+H]^+$, 815.3 $[M+Na]^+$.

Synthesis of compound 6: 2-Azidoacetic acid (80 mg, 0.039 mmol, 5% w/w in dichloromethane) was dissolved in DMF (1 mL) and treated with NHS (4.49 mg, 0.039 mmol) and EDC (7.48 mg, 0.039 mmol) at room temperature. After stirring for 1 hr, a solution of compound 5 (25 mg, 0.032 mmol) in DMF (1 mL) and DIPEA (10 μL, 0.058 mmol) were added to the reaction mixture and stirred for 3 hr. LCMS shows all the starting material was consumed. Solvent was removed under high vacuum, and residue was dissolved in water (3 mL). After filtration, the desired product was isolated by semi-preparative HPLC. The collected fractions were combined and lyophilized to afford compound 6 (13 mg, 46%) as a white fluffy powder. MS (m/z) (ESI): 876.1 $[M+H]^+$, 898.1 $[M+Na]^+$.

Synthesis of Compound 7: To a small vial containing compound 6 (1.5 mg, 1.71 μmol), 5-fluoropent-1-yne (25 μL), $CH_3OH$ (400 μL), and sodium ascorbate solution (25 μL, 0.5

M) were added to a copper sulfate solution (25 μL, 0.1 M). The reaction was stirred at room temperature for 2 hr. The reaction mixture was then concentrated to dryness and redissolved in water (3 mL). After filtration, the desired product was isolated by semi-preparative HPLC. The collected fractions were combined and lyophilized to afford compound 7 (1.2 mg, 73%) as a white fluffy powder. MS (m/z) (ESI): 962.2 [M+H]⁺, 984.1 [M+Na]⁺.

Conjugation of [$^{18}$F]fluoroalkyne, prepared using the corresponding tosylated alkyne as a precursor, to cyclopeptides derivatized with azido group via Cu(I) mediated 1,3-dipolar cycloaddition yields the desired $^{18}$F-labeled products with good yields and excellent radiochemical purity. See Scheme IV.

Scheme IV

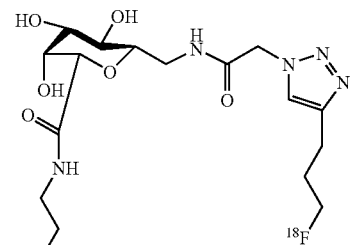

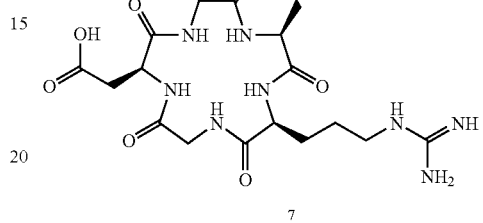

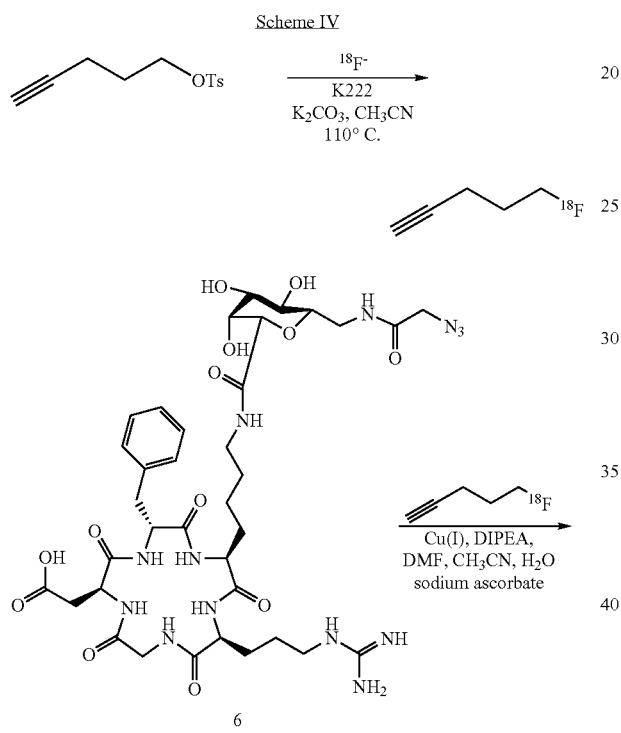

-continued

Typically, 1-pentynyl tosylate (15 mg) is $^{18}$F-labeled in CH₃CN at 110° C. in the presence of K222 and K₂CO₃ for 5 min while simultaneously distilling the material into a cooled solution containing 2.3 mg of Compound 6, 6 mg of CuI, 200 μL of DMF, 250 μL of CH₃CN, 25 μL di-isopropylethyl amine, 250 μL of water and 25 mg of sodium ascorbate. The reaction is stirred for 15-60 min at room temperature. The reaction mixture is then loaded onto an HPLC C18 column for purification. After collecting the product, the material is reconstituted via C18 loading and unloading with EtOH and diluting with water to make a 10% EtOH:Water solution. The yields vary from ~35 mCi to ~1 mCi.

Another exemplary preparation of one of the cyclic RGD peptide derivatives of the present application, Compound 10, is shown in Scheme V.

Scheme V

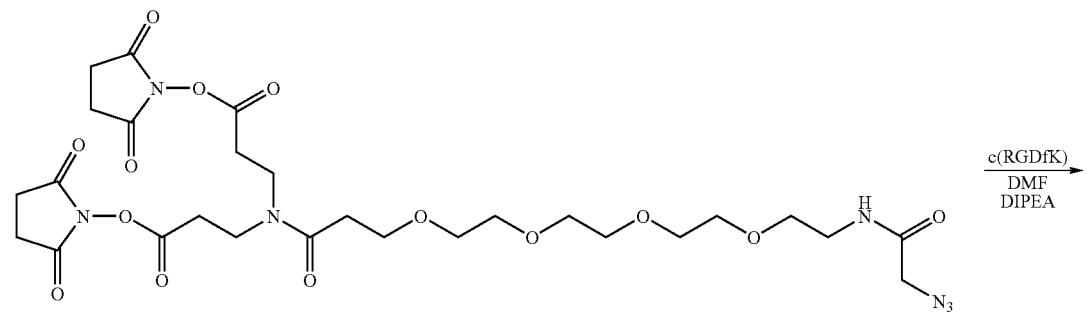

8

-continued
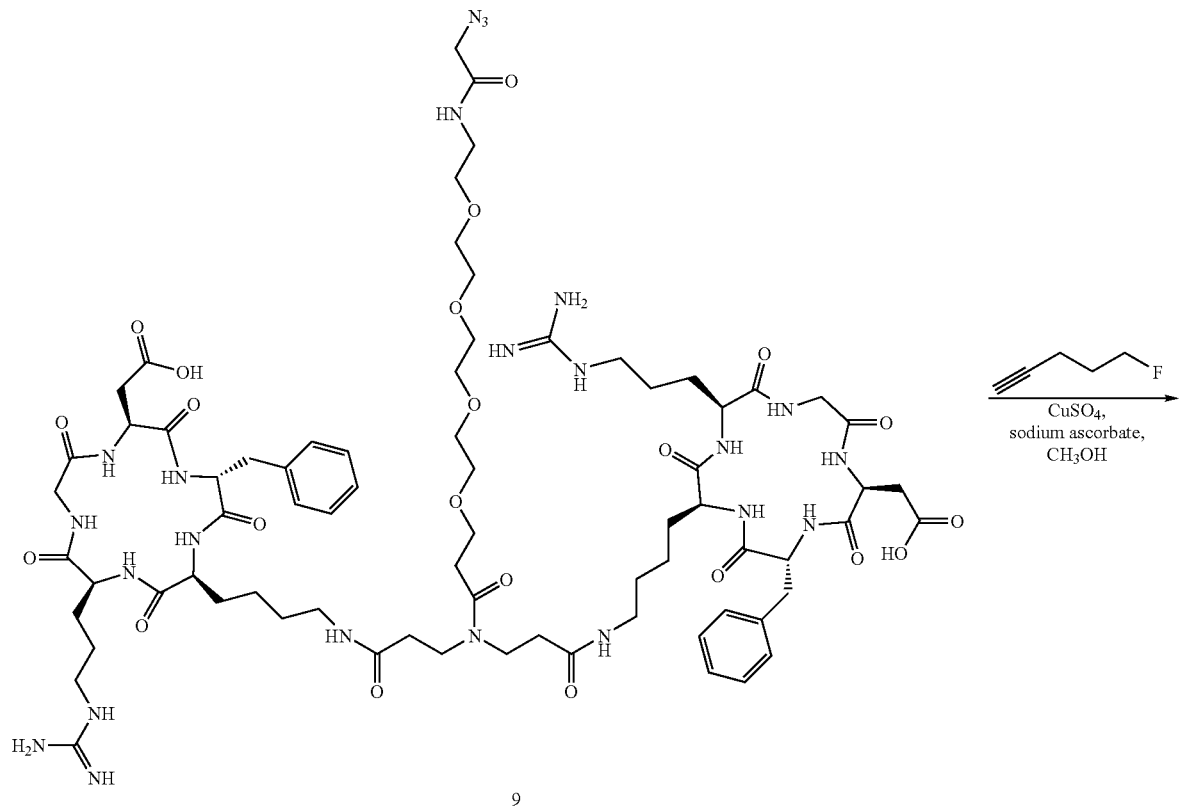
9
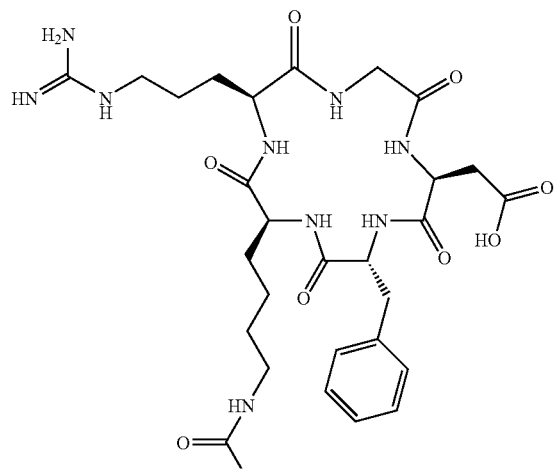

-continued

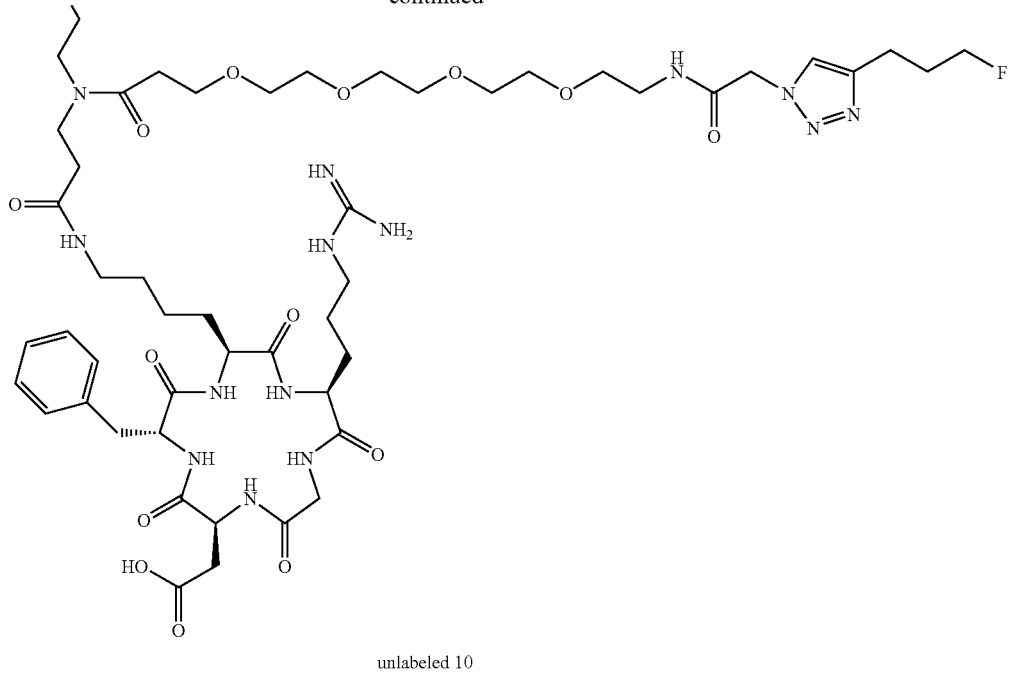

unlabeled 10

Synthesis of Compound 10:

Synthesis of Compound 9: To a solution of compound 8 (23 mg, 0.034 mmol) in DMF (2 mL), c(RGDfK) (50 mg, 0.083 mmol) was added, followed by DIPEA (17 µL, 0.102 mmol). The reaction mixture was stirred for 12 hr at room temperature. LC/MS shows the starting material was consumed. After solvent was removed under high vacuum, the residue was dissolved in water (5 mL) and acetonitrile (5 mL). After filtration, the desired product was isolated by semi-preparative HPLC. The collected fractions were combined and lyophilized to afford compound 9 (18 mg, 32%) as a white fluffy powder. MS (m/z) (ESI): 1663.4 [M+H]$^+$.

Synthesis of Compound 10: To a small vial containing compound 9 (3 mg, 1.8 µmol), 5-fluoropent-1-yne (25 µL), CH$_3$OH (400 µL), and sodium ascorbate solution (25 µL, 0.5 M) was added copper sulfate solution (25 µL, 0.1 M). The reaction was stirred at room temperature for 2 hr. The reaction mixture was then concentrated to dryness and redissolved in water (3 mL). After filtration, the desired product was isolated by semi-preparative HPLC. The collected fractions were combined and lyophilized to afford unlabeled Compound 10 (2 mg, 63%) as a white fluffy powder. MS (m/z) (ESI): 1749.3 [M+H]$^+$.

Consistent with Scheme IV, radiolabeled Compound 10 was prepared via reaction of [$^{18}$F]-5-fluoropent-1-yne and Compound 9. The product was isolated from the reaction mixture using a HPLC C18 purification column. The material was reconstituted via C18 loading and unloading with EtOH and dilution with water to make a 10% EtOH:H$_2$O solution. Yields varied from ~35 mCi to ~1 mCi.

PET Studies of Compound 7: In vivo microPET imaging of anesthetized mice bearing tumor xenograft of either U87MG human glioblastoma or A427 human lung carcinoma were performed after administration of Compound 7. In vivo microPET imaging shows that Compound 7 is a very good tracer with good tumor uptake and retention and a fast washout rate from muscle and other healthy tissues. See e.g. FIGS. 1-4.

Comparison of in vivo microPET imaging of [$^{18}$F]galacto-RGD (a known tracer for integrin imaging) demonstrates that Compound 7 has both faster kinetics and less liver and gastrointestinal uptake in a U87MG xenograft mouse model. See e.g. FIG. 2.

PET Studies of Compound 10: In vivo microPET imaging of anesthetized mice bearing tumor xenograft of either U87MG human glioblastoma or A427 lung carcinoma were performed after administration of Compound 10. In vivo microPET imaging shows that Compound 10 is a very good tracer with good tumor uptake and retention and a fast washout rate from muscle and other healthy tissues. See e.g. FIGS. 5-8.

Figure 9:
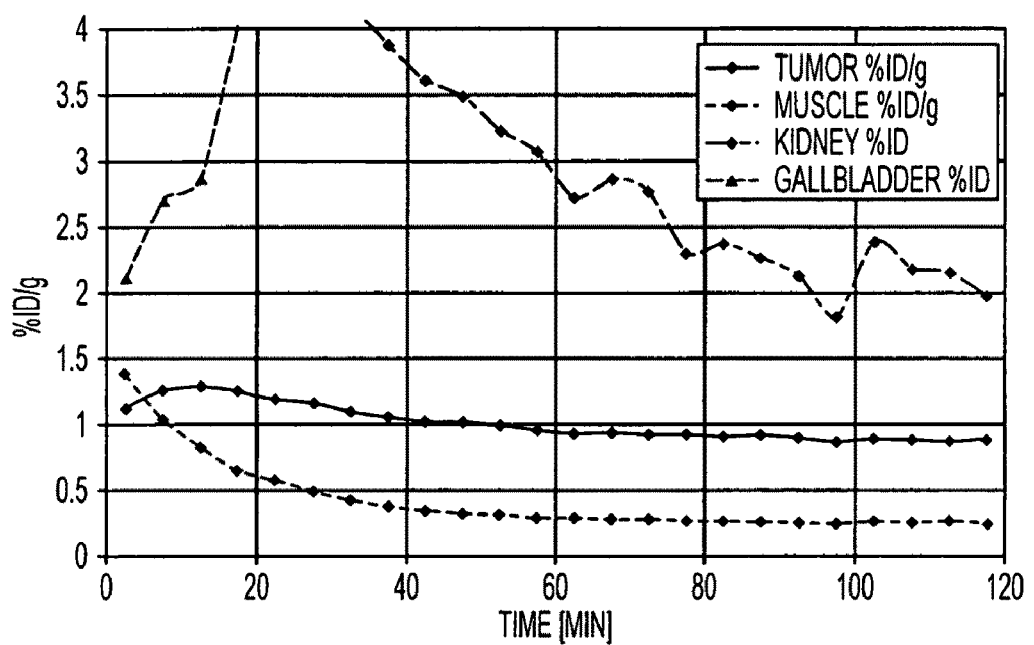
FIG. 9 is a graph of tumor accumulation (% Injected Dose/g) vs. time for Compound 7 in a A427 Xenograft Mouse Model.
Figure 10:
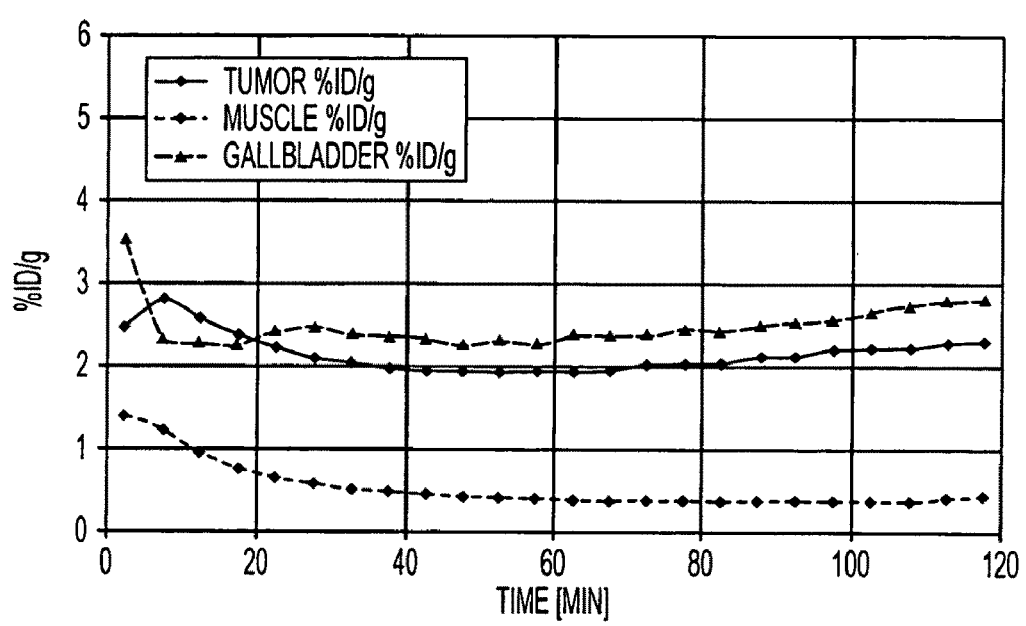
FIG. 10 is a graph of tumor accumulation (% Injected Dose/g) vs. time for Compound 7 in a U87MG Xenograft Mouse Model.
Figure 11:
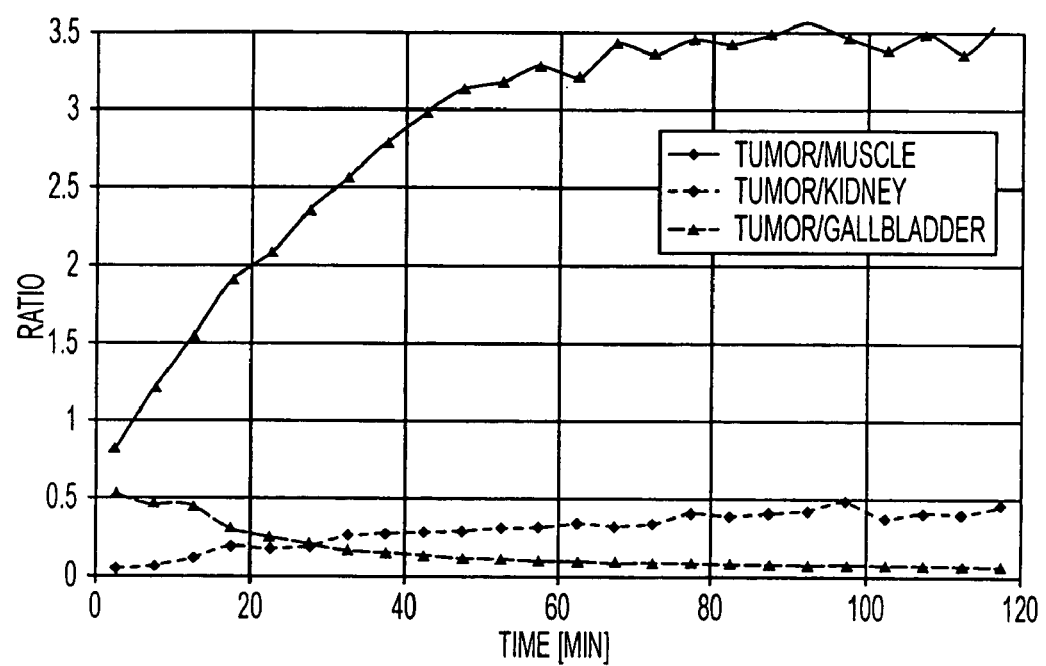
FIG. 11 is a graph of ratio of tumor to tissue (muscle, kidney or gall bladder) uptake over time of Compound 7 in a A427 Xenograft Mouse Model.
Figure 12:
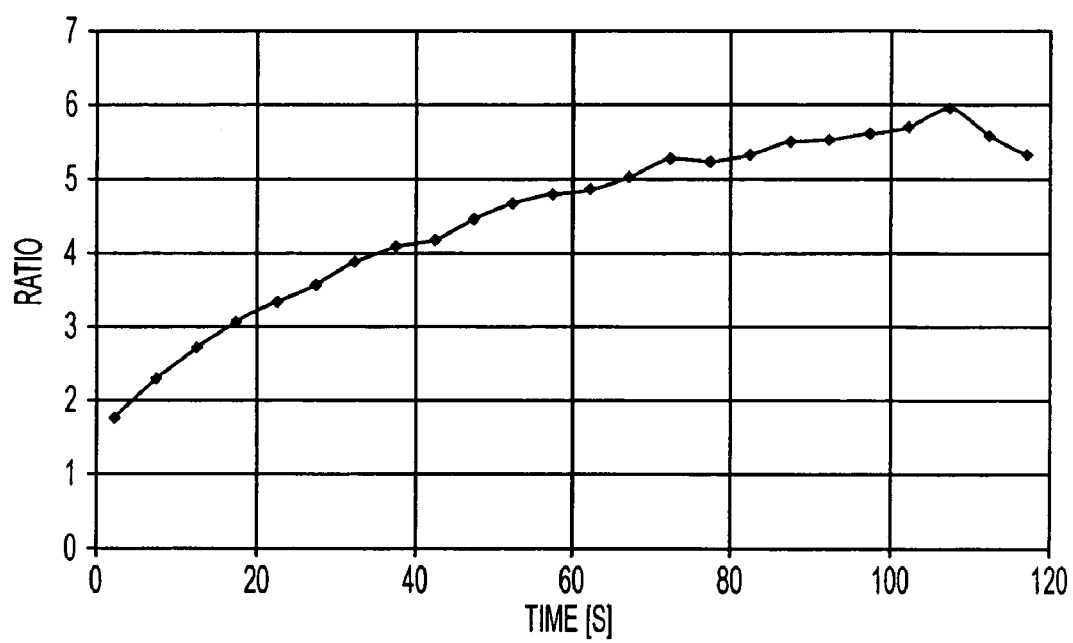
FIG. 12 is a graph of ratio of tumor to muscle uptake over time of Compound 7 in a U87MG Xenograft Mouse Model.

Biodistribution Studies of Compound 7: Nude mice bearing tumor xenograft of either U87MG human glioblastoma or A427 human lung carcinoma were i.v. injected with Compound 7. The animals were sacrificed and dissected at fixed times after injection. At least blood, muscle, gall bladder, liver, and tumor were removed and weighed. The radioactivity in the tissue was measured using a gamma counter. Results are expressed as % ID/g (% Injected Dose/gram). See FIGS. 9 and 10. FIGS. 11 and 12, graphs of the tumor to tissue uptake over time indicates that in particular, Compound 7 demonstrates a tumor/muscle ratio of >3:1 after 2 hr in the A427 xenograft mouse model and a tumor/muscle ratio of >5:1 after 2 hr in the U87MG xenograft mouse model, indicating excellent tumor uptake.

Figure 13:
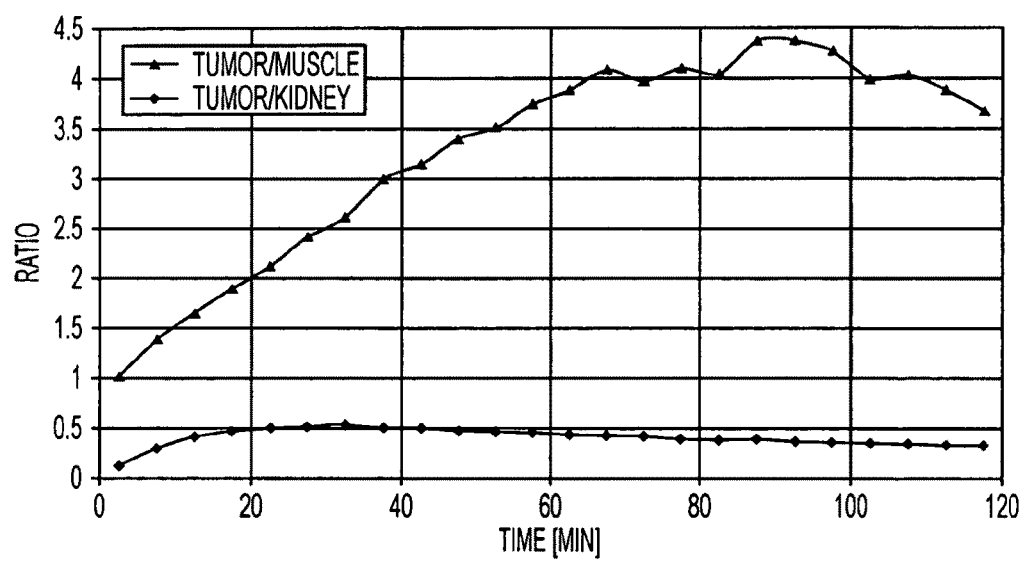
FIG. 13 is a graph of ratio of tumor to tissue uptake over time of Compound 10 in a A427 Xenograft Mouse Model.
Figure 14:
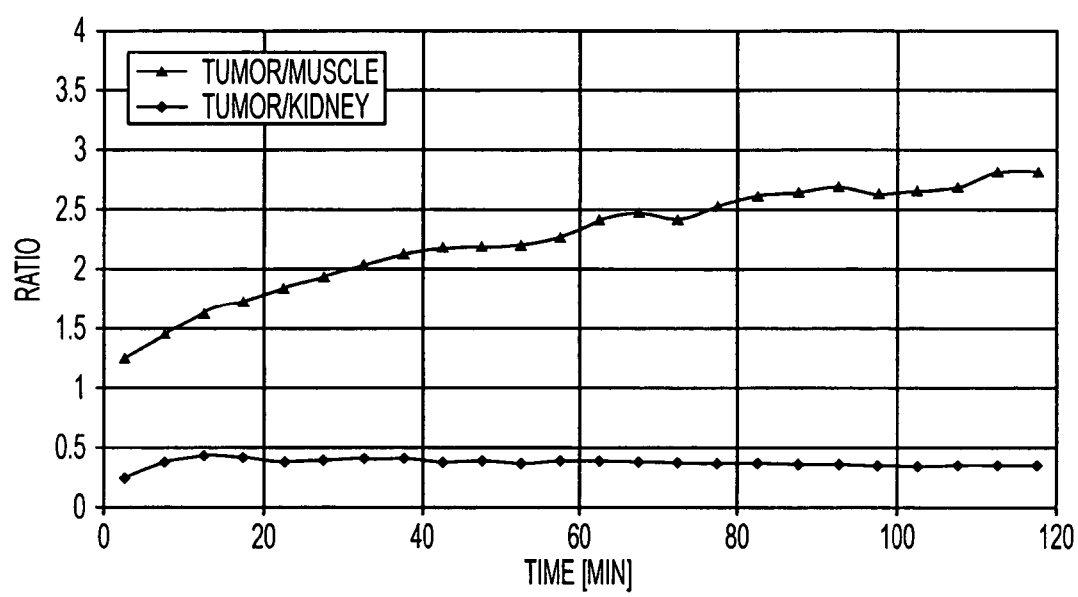
FIG. 14 is a graph of ratio of tumor to muscle uptake over time of Compound 10 in a U87MG Xenograft Mouse Model.

Biodistribution Studies of Compound 10: Nude mice bearing tumor xenograft of either U87MG human glioblastoma or A427 human lung carcinoma were i.v. injected with Compound 10. The animals were sacrificed and dissected at fixed times after injection. At least blood, kidneys, liver, and urine were collected and weighed. The radioactivity in the tissue was measured using a gamma counter. Results are expressed as Entire Organ Counts per Minute/Injected Dose Counts per Minute times 100%. See FIG. 17. FIGS. 13 and 14, graphs of the tumor to tissue uptake over time indicates that Compound 10 demonstrates a tumor/muscle ratio of greater than 3.5:1 after 2 hr in the A427 xenograft model and greater than 2.5:1 after 2 hour in the U87MG xenograft model.

Metabolic Stability Studies for Compound 7 and Compound 10: For each tracer (radiolabeled compound) of interest the following protocol was followed: Two mice were anesthetized with Florane. For each mouse, 300 µCi of tracer, in 200 µL saline was injected into the tail vein. Pressure was applied to the injection site for one minute to stop bleeding. The mice were then placed in a clean cage (one mouse/cage) without any bedding and observed until they awakened.

In order to confirm the elution time of the radiolabeled compounds 7 and 10, the tracer (2 µL) and the corresponding unlabeled compound ('the cold standard') (dissolved in 200 µL water) were co-injected into radio-HPLC. In each case, the retention time of the tracer as determined by the radiodetector was identical to the retention time of the cold standard compound as determined by the UV detector.

At 30 or 60 minutes post injection, 300-500 µL of blood was drawn via cardiac puncture into a syringe containing anti-coagulant. The blood was then centrifuged for 3 minutes to separate the plasma. The mice were then killed and the liver, the gall bladder and the kidneys were harvested and placed into separate tubes containing 2 mL lysis buffer. The organs were homogenized mechanically. 400 µL of each homogenate was then transferred to a tube, extracted with 200 µL chloroform/methanol (50/50) mixture, and vortexed.

All urine was collected from each cage at 30 or 60 minutes and 10 mL of water was added to wash the dried urine in the cages. A 1 mL aliquot of solution was taken out and transferred into a tube. The radioactivity of the solution was then measured using a gamma counter.

Lysis buffer and chloroform/methanol mixture were also added to plasma and urine samples after they were weighted (sample weight in gram). All tubes were vortexed and frozen in dry ice. After the tubes were centrifuged for 3 minutes, the supernatant was transferred into new tubes. The radioactivity of the supernatant and the precipitation were counted at the same time to calculate total injected dose. The sample CPM (counts per minute) is the sum of CPM in the supernatant and in the precipitation. Thus, the percentage of injected dose per tissue weight (gram) can be calculated according to the following function:

% injected dose/g tissue=sample CPM/sample weigh (g)/(2 µl CPM×100)

While there are metabolites of the tracer found in the mouse body, the percentage of the original tracer and that of the metabolites can be calculated from the radio-HPLC data.

Figure 15A:
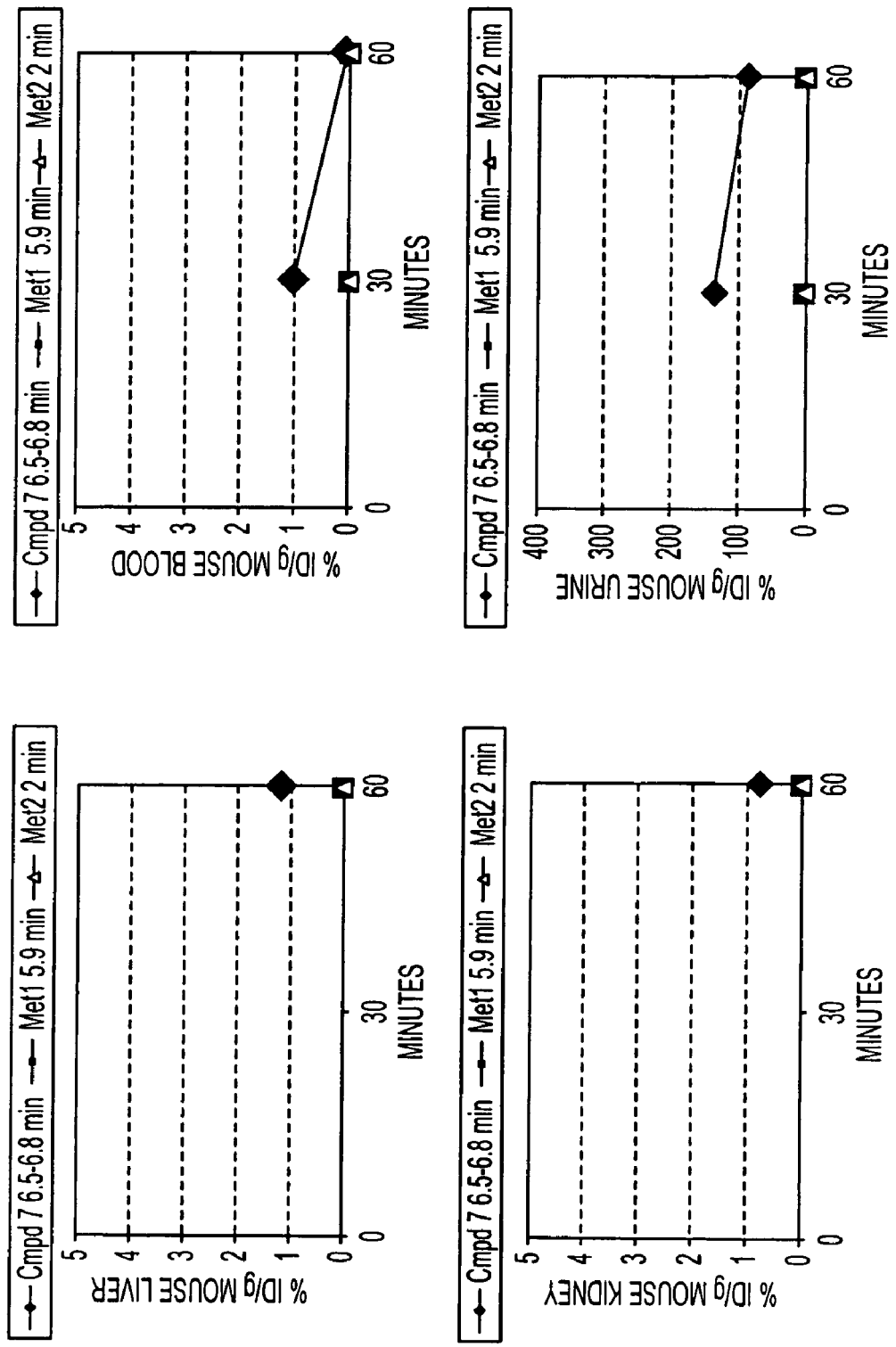
FIG. 15A are graphs from a metabolic stability study of Compound 7 in mice by radio-HPLC.
Figure 15B:
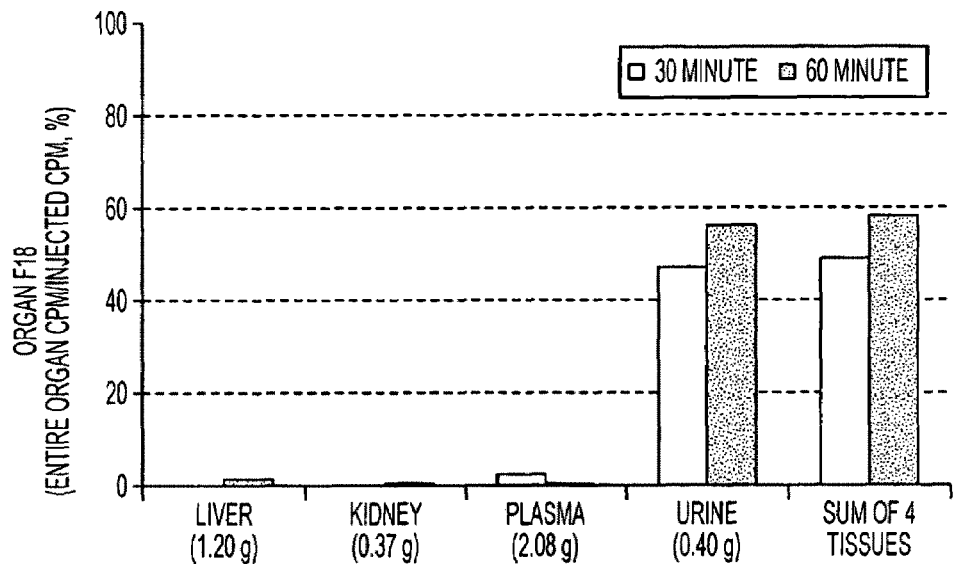
FIG. 15B is a graph from biodistribution studies of Compound 7 in mice.
Figure 16A:
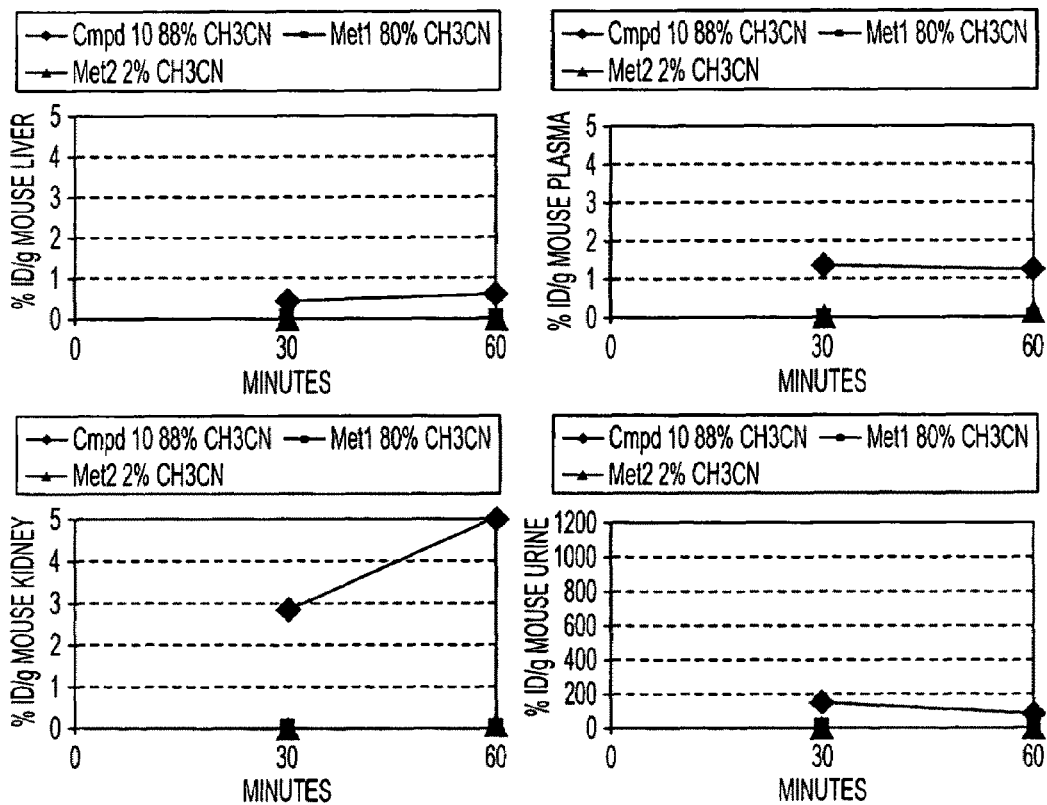
FIG. 16A are graphs from a metabolic stability study of Compound 10 in mice by radio-HPLC.
Figure 16B:
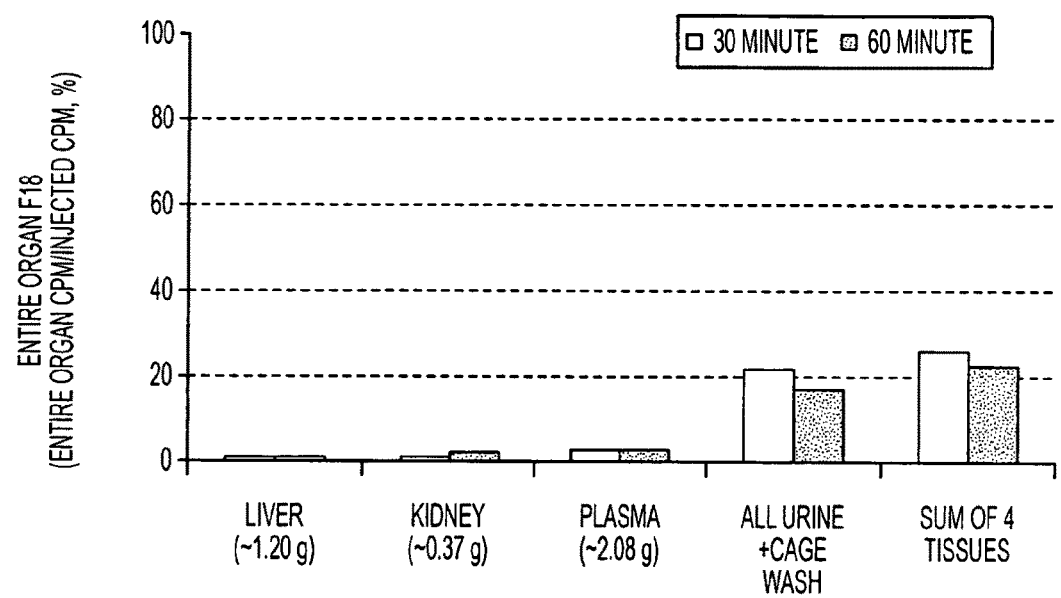
FIG. 16B is a graph from biodistribution studies of Compound 10 in mice.

The data show that in each example only minor amounts radioactive metabolites were found in the murine tissue and fluid samples. Thus, Compound 7 and Compound 10 are each very stable in a mouse body. See e.g. FIGS. 15 and 16.

All references cited herein are incorporated by reference as if each had been individually incorporated by reference in its entirety. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

REFERENCES

1. Aumailley, M.; Gurrath, M.; Muller, G.; Calvete, J.; Timpl, R.; Kessler, H., *FEBS Lett.* 1991, 291, 50-54.

2. Haubner, R.; Wester, H. J.; Reuning, U.; Senekowisch-Schmidtke, R.; Diefenbach, B.; Kesser, H.; Stocklin, G.; Schwaiger, M., *J. Nucl. Med.,* 1999, 40, 1061-1071.

3. Haubner, R.; Wester, H. J.; Burkhart, F.; Senekowisch-Schmidtke, R.; Weber, W.; Goodman, S. L.; Kessler, H.; Schwaiger, M., *J. Nucl. Med.,* 2001, 42, 326-336.

4. Haubner, R.; Weber, W. A.; Beer, A. J.; Vabuliene, E.; Reim, D.; Sarbia, M.; Becker, K. F.; Goebel, M., et al. *PLoS Med.,* 2005, 2, e70.

5. Haubner, R.; Wester, H. J.; Weber, W. A.; Mang, C.; Ziegler, S. I.; Goodman, S. L.; Senekowisch-Schmidtke, R.; Kessler, H.; Schwaiger, M., *Cancer Res.,* 2001, 61, 1781-1785.

6. Haubner, R.; Kuhnast B,; Mang, C.; Weber W. A.; Kessler, H.; Wester, H. J.; Schwaiger, M., *Bioconjug. Chem.,* 2004, 15, 61-69.

7. Chen, X.; Park, R.; Shahinian, A. H.; Bading, J. R.; Conti, P. S., *Nucl. Med. Biol.,* 2004, 31, 11-19.

8. Chen, X.; Park, R.; Hou, Y.; Khankaldyyan, V.; Gonzales-Gomez, I.; Tohme, M.; et al., *Eur. J. Nul. Med. Mol. Imaging,* 2004, 31, 1081-1089.

9. Chen, X.; Hou, Y.; Tohme, M.; Park, R.; Khankaldyyan, V.; Gonzales-Gomez, I.; et al., *J. Nul. Med.,* 2004, 45, 1776-1783.

10. Kolb, H. C.; Finn, M. G.; Sharpless, K. B. *Angewandte Chemie, International Edition* 2001, 40, 2004-2021.

11. Kolb, H. C.; Sharpless, K. B., *Drug Discovery Today* 2003, 8, 1128-1137.

12. Rostovtsev, V. V.; Green, L. G.; Fokin, V. V.; Sharpless, K. B. *Angewandte Chemie, International Edition* 2002, 41, 2596-2599.

13. Tornøe, C. W.; Christensen, C.; Meldal, M., *Journal of Organic Chemistry* 2002, 67, 3057-3064.

14. Wang, Q.; Chan, T. R.; Hilgraf, R.; Fokin, V. V.; Sharpless, K. B.; Finn, M. G., *Journal of the American Chemical Society* 2003, 125, 3192-3193.

15. Lee, L. V.; Mitchell, M. L.; Huang, S.-J.; Fokin, V. V.; Sharpless, K. B.; Wong, C.-H., *Journal of the American Chemical Society* 2003, 125, 9588-9589.

16. Lewis, W. G.; Green, L. G.; Grynszpan, F.; Radic, Z.; Carlier, P. R.; Taylor, P.; Finn, M. G.; Barry, K., *Angew. Chem., Int. Ed.* 2002, 41, 1053-1057.

17. Manetsch, R.; Krasinski, A.; Radic, Z.; Raushel, J.; Taylor, P.; Sharpless, K. B.; Kolb, H. C., *Journal of the American Chemical Society* 2004, 126, 12809-12818.

18. Mocharla, V. P.; Colasson, B.; Lee, L. V.; Roeper, S.; Sharpless, K. B.; Wong, C.-H.; Kolb, H. C., *Angew. Chem. Int. Ed.* 2005, 44, 116-120.

19. Beer, A. J., et al., *J. Nucl. Med.* 2006 47:763-769.

What is claimed:
1. A cyclopeptide of formula I:

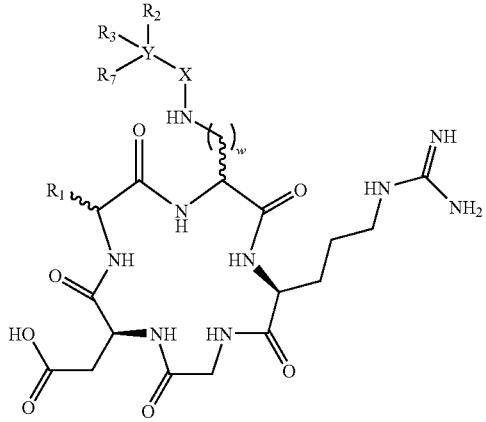

wherein:
R$_1$ is selected from the group consisting of a side chain of a natural amino acid and a side chain of an unnatural amino acid, wherein the natural amino acid and the unnatural amino acid is either in the D or L form;
R$_2$ and R$_3$ are each independently selected from the group consisting of H, C$_1$-C$_6$ alkyl, C$_2$-C$_6$ alkenyl, C$_2$-C$_6$ alkynyl, aryl, aryl-(C$_1$-C$_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted;
R$_7$ is absent or is selected from the group consisting of H, C$_1$-C$_6$ alkyl, C$_2$-C$_6$ alkenyl, C$_2$-C$_6$ alkynyl, aryl, aryl-(C$_1$-C$_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted; wherein R$_2$, R$_3$ and R$_7$ are not all H;
X is a 5 or 6-membered heterocycle or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;
Y is a 5 or 6-membered heterocycle, or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;
where at least one of X and Y, but not both X and Y is a 5 or 6-membered heterocycle; and
w is 1, 2, 3, 4, or 5;
wherein any one of X, Y, R$_2$, R$_3$, and R$_7$ comprises a radionuclide selected from the group consisting of positron or gamma emitters.

2. The cyclopeptide of claim 1 wherein Y is a 5 or 6-membered heterocycle; and X is a linker either comprising a sugar mimetic selected from the group consisting of a 4 to 6-membered carbocycle substituted with at least one hydroxyl group and a 5- to 6-membered heterocycle substituted with at least one hydroxyl group or comprising a sugar moiety selected from the group consisting of glucose and galactose.

3. The cyclopeptide of claim 1 wherein:
Y is a 5 or 6-membered heterocycle;
X is selected from the group consisting of:

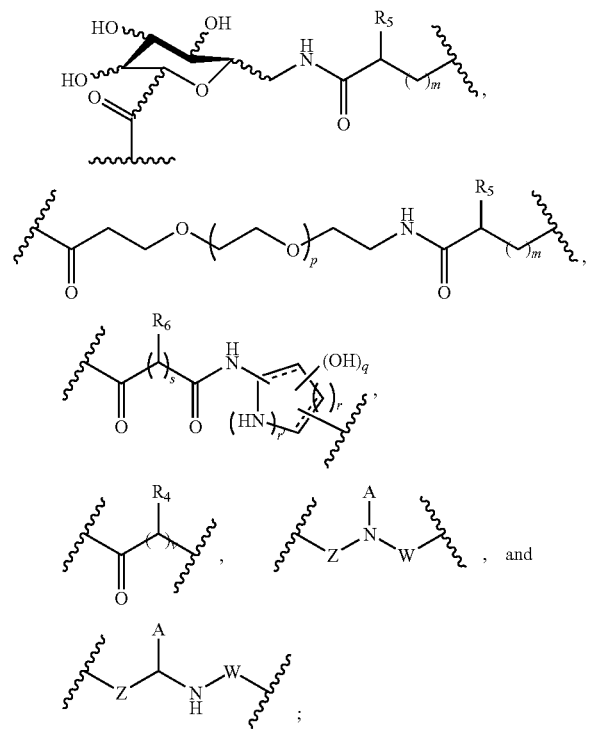

wherein Z is selected from the group consisting of:

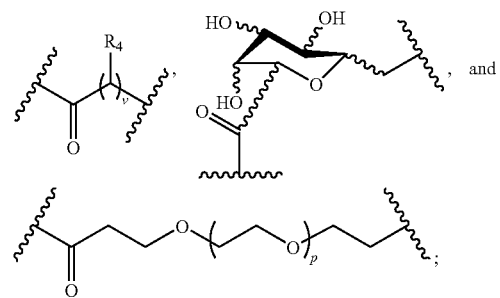

W is selected from the group consisting of:

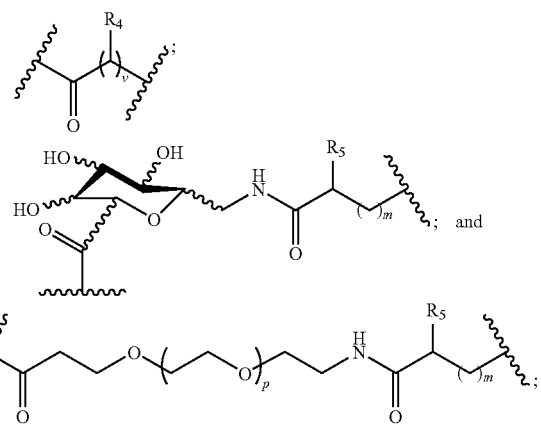

A is selected from the group consisting of:

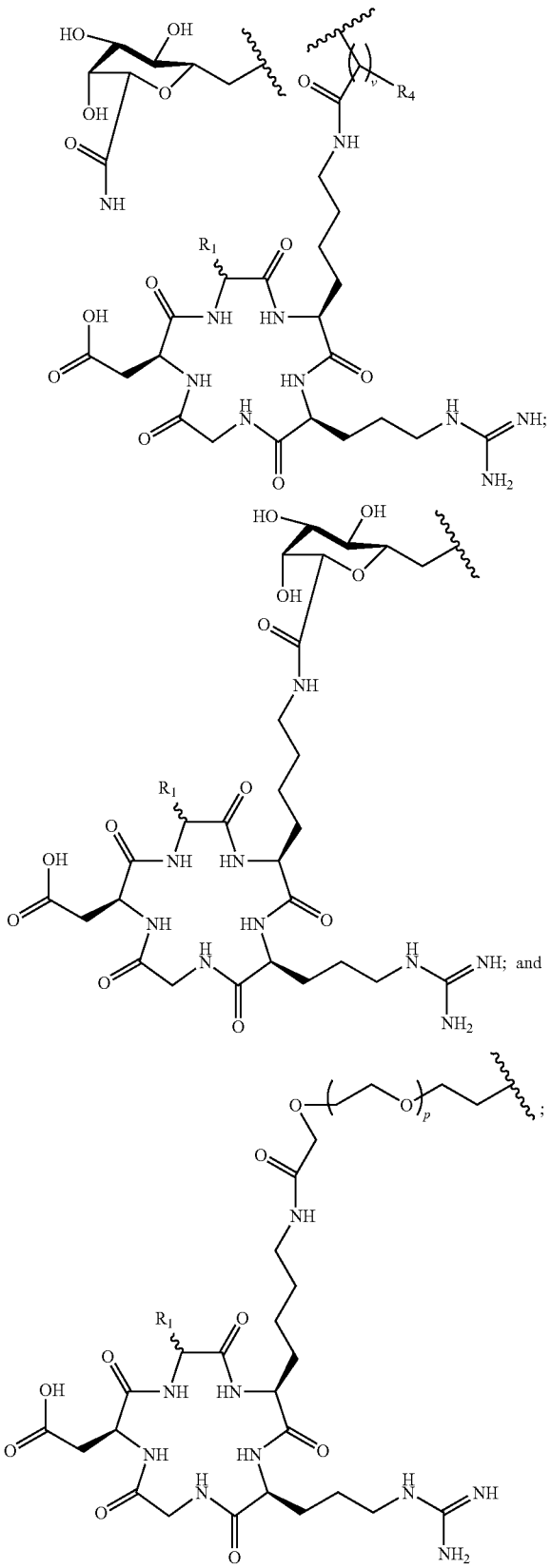

each $R_1$ is independently selected from the group consisting of a side chain of a natural amino acid and a side chain of an unnatural amino acid, wherein the natural amino acid and the unnatural amino acid is either in the D or L form;

each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted;

each $R_6$ is independently selected from the group consisting of —H, —OH, $C_1$-$C_6$ alkyl, $C_2$-$C_6$ alkenyl, $C_2$-$C_6$ alkynyl, $C_1$-$C_6$ alkyloxy, aryl-($C_1$-$C_6$ alkylene)-, hydroxy-$C_1$-$C_6$-alkyl, and $C_1$-$C_6$-alkoxy-$C_1$-$C_6$-alkyl, wherein the alkyl, alkenyl, alkynyl, alkyloxy, and arylalkylene groups are each optionally substituted;

each v is 0, 1, 2, 3, or 4;

m is 0, 1, 2, 3 or 4;

p is an integer between 1 and 110;

q is 1, 2, 3 or 4;

r is 1, 2 or 3;

r' is 0 or 1;

s is 1, 2, 3 or 4; and the radionuclide is selected from the group consisting of $^{11}$C, $^{13}$N, $^{15}$O, $^{18}$F, $^{61}$Cu, $^{62}$Cu, $^{64}$Cu, $^{67}$Cu, $^{68}$Ga, $^{124}$I, $^{125}$I, $^{131}$I, $^{99}$Tc, $^{75}$Br, $^{153}$Gd, $^{132}$P;

wherein the configuration of the chiral centers may be R or S or mixtures thereof.

4. The cyclopeptide of claim 3 wherein:

$R_1$ is a side chain of a natural amino acid;

$R_7$ is absent;

X is

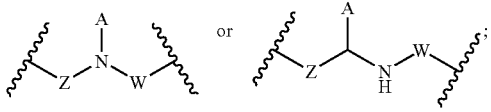

Y is 1,2,3-triazolyl; and $R_2$ and $R_3$ are each independently selected from the group consisting of —H, $C_1$-$C_6$ alkyl, $C_2$-$C_6$ alkenyl, and $C_2$-$C_6$ alkynyl, wherein the alkyl, alkenyl, and alkynyl groups are each optionally substituted, wherein $R_2$ and $R_3$ are not both H; and either $R_2$ or $R_3$, or both $R_2$ and $R_3$ comprise a radionuclide selected from the group consisting of $^{11}$C, $^{13}$N, $^{15}$O, $^{18}$F, $^{75}$Br, $^{124}$I, $^{125}$I and $^{131}$I.

5. A cyclopeptide of formula II:

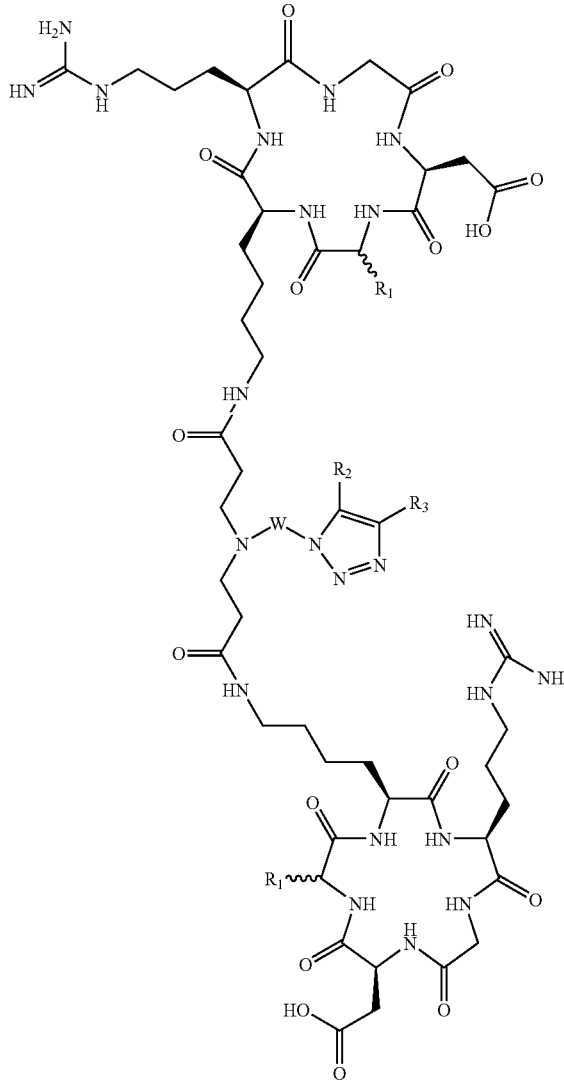

II wherein
- each $R_1$ is independently selected from the group consisting of a side chain of a natural amino acid and a side chain of an unnatural amino acid, wherein the natural amino acid and the unnatural amino acid is either in the D or L form;
- $R_2$ and $R_3$ are each independently selected from the group consisting of —H, $C_1$-$C_6$ alkyl, $C_2$-$C_6$ alkenyl, and $C_2$-$C_6$ alkynyl, wherein the alkyl, alkenyl, and alkynyl groups are each optionally substituted, wherein $R_2$ and $R_3$ are not both H; and either $R_2$ or $R_3$, or both $R_2$ and $R_3$ comprise a radionuclide selected from the group consisting of $^{11}$C, $^{13}$N, $^{15}$O, $^{18}$F, $^{75}$Br, $^{124}$I, $^{125}$I and $^{131}$I; and
- W is

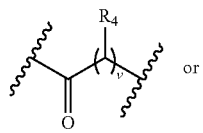 or

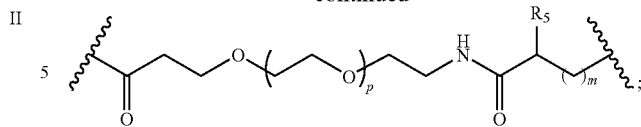

where p is an integer between 0 and 15;
v is 0, 1, 2, or 3;
m is 0, 1 or 2;
each $R_4$ is independently selected from the group consisting of —H, $C_1$-$C_6$ alkyl, $C_2$-$C_6$ alkenyl, and $C_2$-$C_6$ alkynyl, wherein the alkyl, alkenyl, and alkynyl groups are each optionally substituted; and
$R_5$ is selected from the group consisting of —H, $C_1$-$C_6$ alkyl, $C_2$-$C_6$ alkenyl, and $C_2$-$C_6$ alkynyl, wherein the alkyl, alkenyl and alkynyl groups are each optionally substituted and wherein the configuration of the chiral center that carries the $R_5$ substituent may be R or S or mixtures thereof.

6. The cyclopeptide of claim 5 wherein
each $R_1$ is benzyl;
$R_2$ is H;
$R_3$ is an optionally substituted $C_1$-$C_6$ alkyl comprising a radionuclide selected from the group consisting of $^{11}$C, $^{13}$N, $^{15}$O, $^{18}$F, $^{75}$Br, $^{124}$I, $^{125}$I and $^{131}$I; and
W is

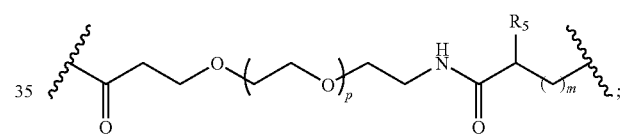

where p is 0, 1, 2, 3, 4, or 5.

7. A cyclopeptide of formula III:

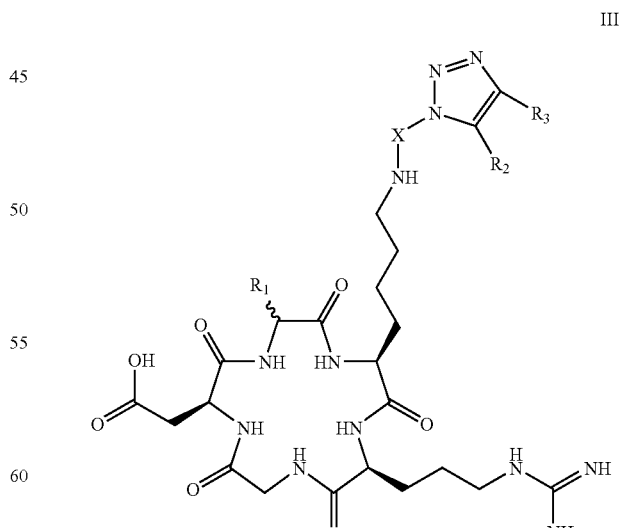

III wherein:
$R_1$ is selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are optionally substituted;

wherein $R_2$ and $R_3$ are not both H; and either $R_2$ or $R_3$, or both $R_2$ and $R_3$ comprise a radionuclide selected from the group consisting of positron or gamma emitters; and X is a linker comprising a hydrophilic moiety selected from the group consisting of hydroxyl, carbonyl, sulfonamide, sulfonate, phosphate, polar amino acid moiety, PEG moiety, sugar mimetic and sugar moiety.

8. The cyclopeptide of claim 7 wherein $R_1$ is a side chain of a natural amino acid; $R_2$ is hydrogen; and $R_3$ comprises a radionuclide selected from the group consisting of $^{11}$C, $^{13}$N, $^{15}$O, $^{18}$F, $^{61}$Cu, $^{62}$Cu, $^{64}$Cu, $^{67}$Cu, $^{68}$Ga, 124I, $^{125}$I, $^{131}$I, $^{99}$Tc, $^{75}$Br, $^{153}$Gd and $^{32}$P.

9. The cyclopeptide of claim 8 wherein $R_1$ is benzyl; and $R_3$ comprises a radionuclide selected from the group consisting of $^{11}$C, $^{13}$N, $^{15}$O, $^{18}$F, $^{124}$I, $^{125}$I, $^{131}$I, and $^{75}$Br.

10. The cyclopeptide of claim 7 wherein:

$R_1$ is a side chain of a natural amino acid; and

X is selected from the group consisting of:

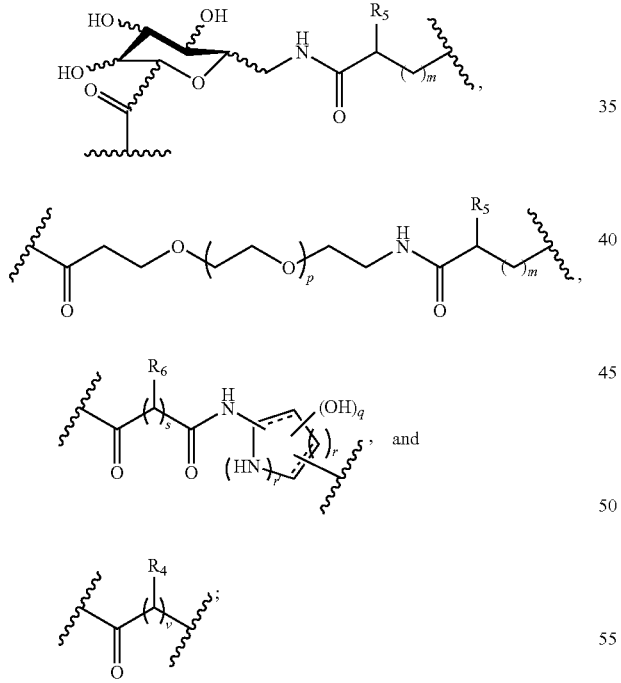

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle and heterocycle groups are each optionally substituted;

each $R_6$ is independently selected from the group consisting of —H, —OH, $C_1$-$C_6$ alkyl, $C_2$-$C_6$ alkenyl, $C_2$-$C_6$ alkynyl, $C_1$-$C_6$ alkyloxy, aryl-($C_1$-$C_6$ alkylene)-, hydroxy-$C_1$-$C_6$-alkyl, and $C_1$-$C_6$-alkoxy-$C_1$-$C_6$-alkyl, wherein the alkyl, alkenyl, alkynyl, alkyloxy, and arylalkylene groups are each optionally substituted;

v is 0, 1, 2, 3, or 4;

m is 0, 1, 2, 3 or 4;

p is an integer between 1 and 110;

q is 1, 2, 3 or 4;

r is 1, 2 or 3;

r' is 0 or 1 s is 1, 2, 3 or 4; and the radionuclide is selected from the group consisting of $^{11}$C, $^{13}$N, $^{15}$O, $^{18}$F, $^{61}$Cu, $^{62}$Cu, $^{64}$Cu, $^{67}$Cu, $^{68}$Ga, $^{124}$I, $^{125}$I, $^{131}$I, $^{99}$Tc, $^{75}$Br, $^{153}$Gd and $^{32}$P;

where the configuration of the chiral centers may be R or S or mixtures thereof.

11. The cyclopeptide of claim 10 wherein:

X is

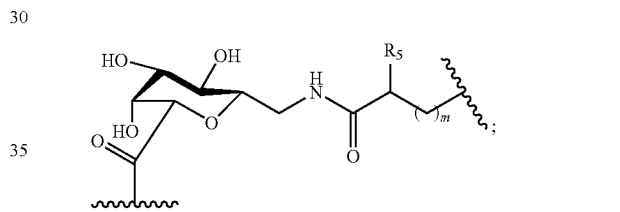

$R_2$ and $R_3$ are each independently selected from the group consisting of —H, $C_1$-$C_6$ alkyl, $C_2$-$C_6$ alkenyl, and $C_2$-$C_6$ alkynyl, wherein the alkyl, alkenyl, and alkynyl groups are each optionally substituted, wherein $R_2$ and $R_3$ are not both H; and either $R_2$ or $R_3$, or both $R_2$ and $R_3$ comprise a radionuclide selected from the group consisting of $^{11}$C, $^{13}$N, $^{15}$O, $^{18}$F, $^{75}$Br, $^{124}$I, $^{125}$I and $^{131}$I;

$R_5$ is selected from the group consisting of —H, $C_1$-$C_6$ alkyl, $C_2$-$C_6$ alkenyl, and $C_2$-$C_6$ alkynyl, wherein the alkyl, alkenyl and alkynyl groups are each optionally substituted and wherein the configuration of the chiral center that carries the $R_5$ substituent may be R or S or mixtures thereof; and m is 0, 1 or 2.

12. The cyclopeptide of claim 11, wherein:

$R_2$ is hydrogen;

$R_3$ is selected from the group consisting of $C_1$-$C_4$ alkyl, $C_2$-$C_4$ alkenyl, and $C_2$-$C_4$ alkynyl, wherein the alkyl, alkenyl and alkynyl groups are each optionally substituted, wherein $R_3$ comprises a radionuclide selected from the group consisting of $^{11}$C, $^{13}$N, $^{15}$O, and $^{18}$F;

$R_5$ is hydrogen; and m is 0.

13. The cyclopeptide of claim 10, wherein:

$R_2$ and $R_3$ are each independently selected from the group consisting of —H, $C_1$-$C_6$ alkyl, $C_2$-$C_6$ alkenyl, $C_2$-$C_6$ alkynyl, wherein the alkyl, alkenyl and alkynyl groups are each optionally substituted; wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{75}Br$, $^{124}I$, $^{125}I$ and $^{131}I$;

X is where $R_5$ is selected from the group consisting of —H, $C_1$-$C_6$ alkyl, $C_2$-$C_6$ alkenyl, and $C_2$-$C_6$ alkynyl, wherein the alkyl, alkenyl and alkynyl groups are each optionally substituted and wherein the configuration of the chiral center that carries the $R_5$ substituent may be R or S or mixtures thereof;

m is 0, 1, or 2; and p is an integer between 1 and 90.

14. The cyclopeptide of claim 13, wherein:

$R_2$ is hydrogen;

$R_3$ is selected from the group consisting of $C_1$-$C_4$ alkyl, $C_2$-$C_4$ alkenyl, and $C_2$-$C_4$ alkynyl, wherein the alkyl, alkenyl and alkynyl groups are each optionally substituted, and $R_3$ comprises a radionuclide selected from the group consisting of $^{11}C$, $^{13}N$, $^{15}O$, and $^{18}F$;

$R_5$ is hydrogen;

m is 0; and p is an integer between 1 and 15.

15. The cyclopeptide of claim 10 wherein:

X is where each $R_6$ is independently selected from the group consisting of —H, —OH, $C_1$-$C_6$ alkyl, $C_2$-$C_6$ alkenyl, $C_1$-$C_6$ alkyloxy, hydroxy-$C_1$-$C_6$-alkyl, and $C_1$-$C_6$-alkoxy-$C_1$-$C_6$-alkyl, wherein the alkyl, alkenyl, and alkyloxy groups are each optionally substituted;

q is 2, 3 or 4;

r is 2 or 3;

r' is 0; and s is 1 or 2.

16. The cyclopeptide of claim 10 wherein:

X is where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted; and v is 1, 2, 3, or 4.

17. A radiolabeled cyclopeptide of formula IV:

IV wherein:

$R_5$ is selected from the group consisting of H, $C_1$-$C_6$ alkyl, $C_2$-$C_6$ alkenyl, $C_2$-$C_6$ alkynyl, $C_1$-$C_6$ alkyloxy, aryl, —($C_1$-$C_6$ alkylene)-aryl, 3- to 7-membered carbocycle, 3- to 7-membered heterocycle, hydroxy-$C_1$-$C_6$-alkyl, and $C_1$-$C_6$-alkoxy-$C_1$-$C_6$-alkyl; wherein the alkyl, alkenyl, alkynyl, alkyloxy, aryl, carbocycle and heterocycle groups are each optionally substituted;

wherein the chiral centers attached to 〰bonds are R or S or mixtures thereof;

m is 0, 1, 2, 3 or 4; and n is 1, 2, 3, 4 or 5.

18. The cyclopeptide of claim 17, wherein:

$R_5$ is selected from the group consisting of H, $C_1$-$C_4$ alkyl, $C_2$-$C_4$ alkenyl, and $C_2$-$C_4$ alkynyl, wherein the alkyl, alkenyl and alkynyl groups are each optionally substituted;

wherein the chiral center in the cyclic peptide is R configured and the chiral center bearing the $R_5$ residue is R or S or mixtures thereof;

m is 0, 1 or 2; and n is 1, 2, 3 or 4.

19. The cyclopeptide of claim 18, wherein:

$R_5$ is selected from the group consisting of —H, and an optionally substituted $C_1$-$C_4$ alkyl;

m is 0 or 1; and n is 2, 3 or 4.

20. A radiolabeled cyclopeptide selected from the group consisting of:

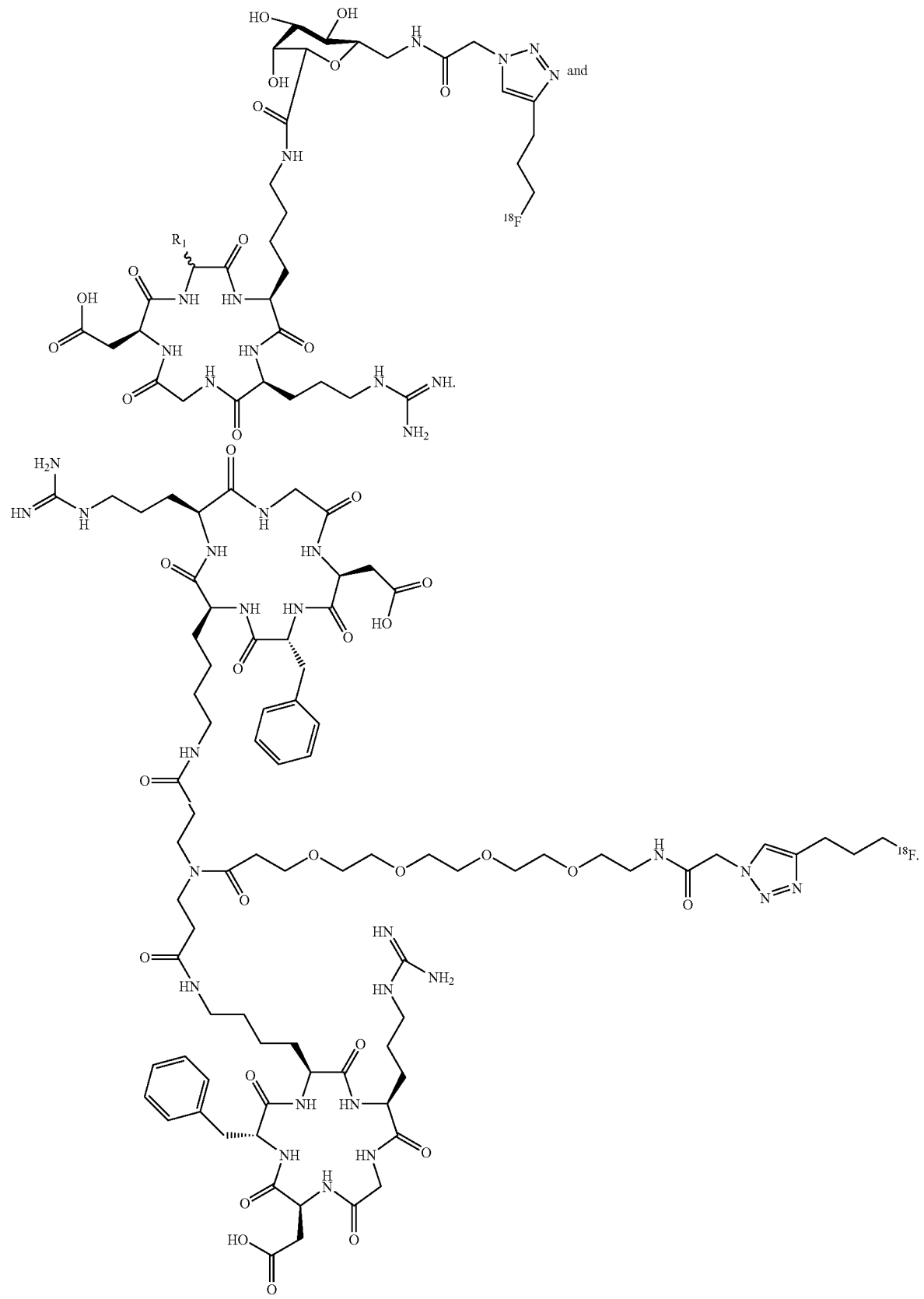

21. A pharmaceutical composition comprising a radiolabeled cyclopeptide of formula I:

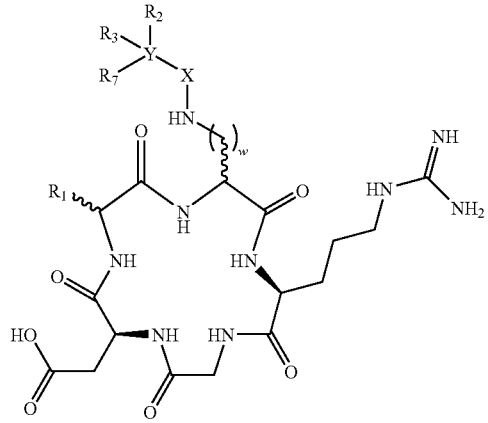

wherein:
R₁ is selected from the group consisting of a side chain of a natural amino acid and a side chain of an unnatural amino acid, wherein the natural amino acid and the unnatural amino acid is either in the D or L form;

R₂ and R₃ are each independently selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted;

R₇ is absent or is selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted; wherein R₂, R₃ and R₇ are not all H;

X is a 5 or 6-membered heterocycle or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

Y is a 5 or 6-membered heterocycle, or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

where at least one of X and Y, but not both X and Y is a 5 or 6-membered heterocycle; and w is 1, 2, 3, 4, or 5;

wherein any one of X, Y, R₂, R₃, and R₇ comprises a radionuclide selected from the group consisting of positron or gamma emitters; and a pharmaceutically acceptable carrier.

22. A pharmaceutical composition comprising a radiolabeled cyclopeptide of formula II or formula III:

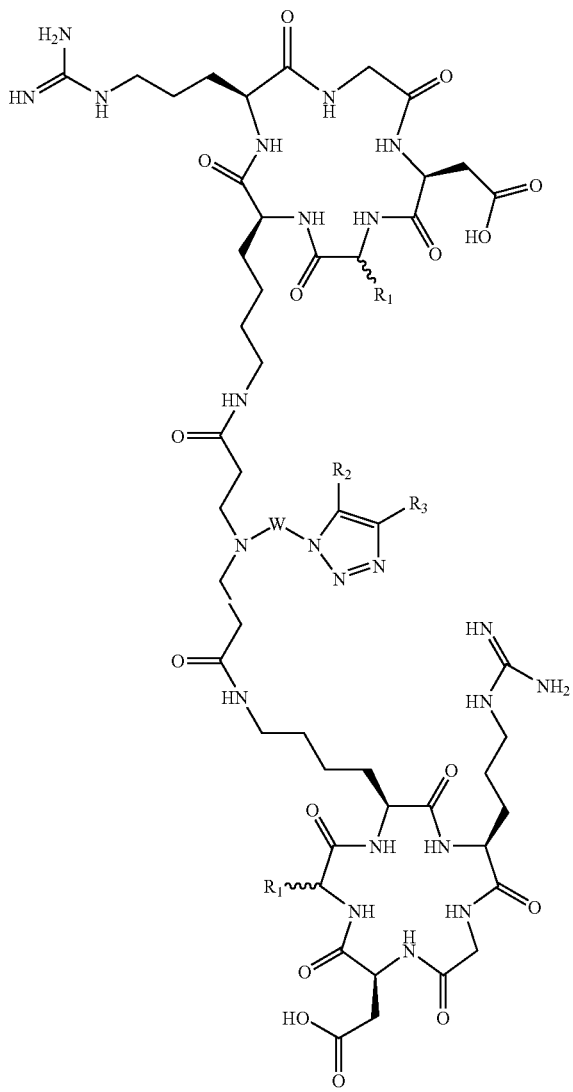

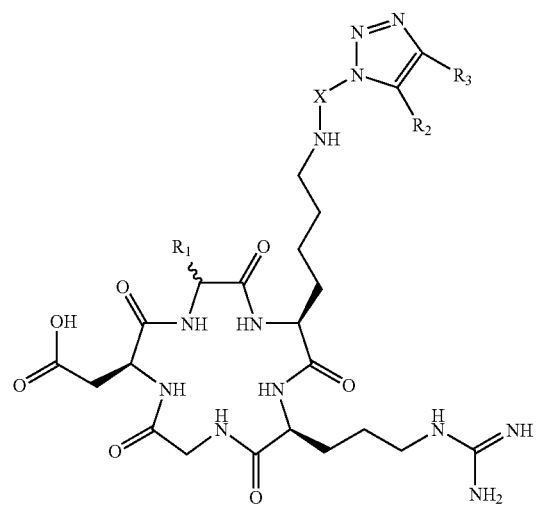

wherein:
  each $R_1$ is independently selected from the group consisting of a side chain of a natural amino acid and a side chain of an unnatural amino acid, wherein the natural amino acid and the unnatural amino acid is either in the D or L form;
  $R_2$ and $R_3$ are each independently selected from the group consisting of —H, $C_1$-$C_6$ alkyl, $C_2$-$C_6$ alkenyl, and $C_2$-$C_6$ alkynyl, wherein the alkyl, alkenyl, and alkynyl groups are optionally substituted, wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$;
  each of X and W is selected from the group consisting of:

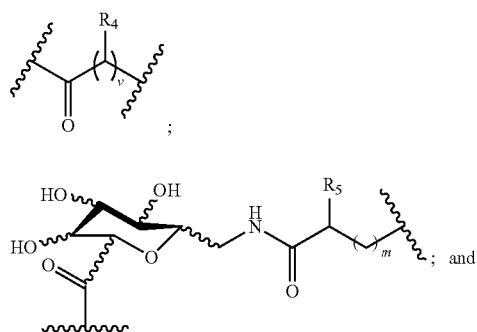

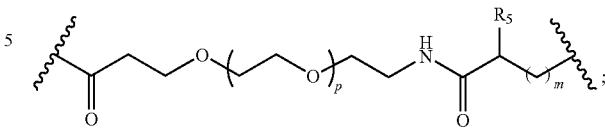

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted;

v is 0, 1, 2, 3, or 4;
m is 0, 1, 2, 3 or 4; and
p is an integer between 1 and 25;
wherein the configuration of the chiral centers may be R or S or mixtures thereof; and a pharmaceutically acceptable carrier.

23. A pharmaceutical composition comprising a radiolabeled cyclopeptide selected from the group consisting of:

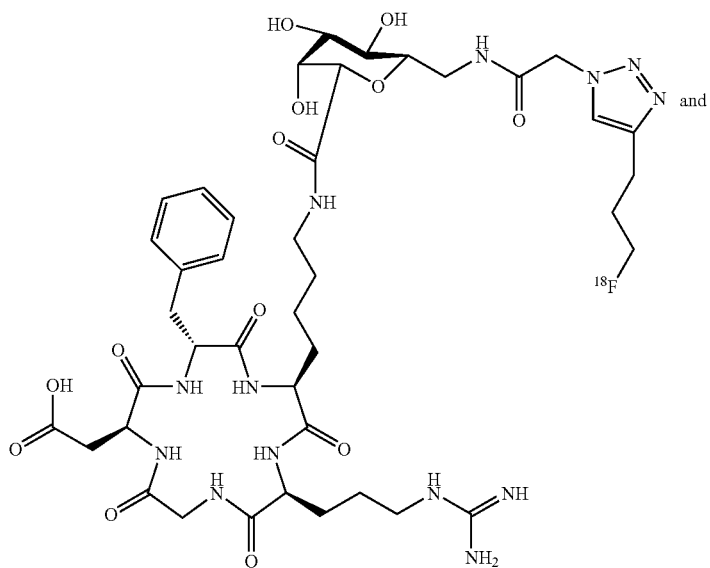

-continued

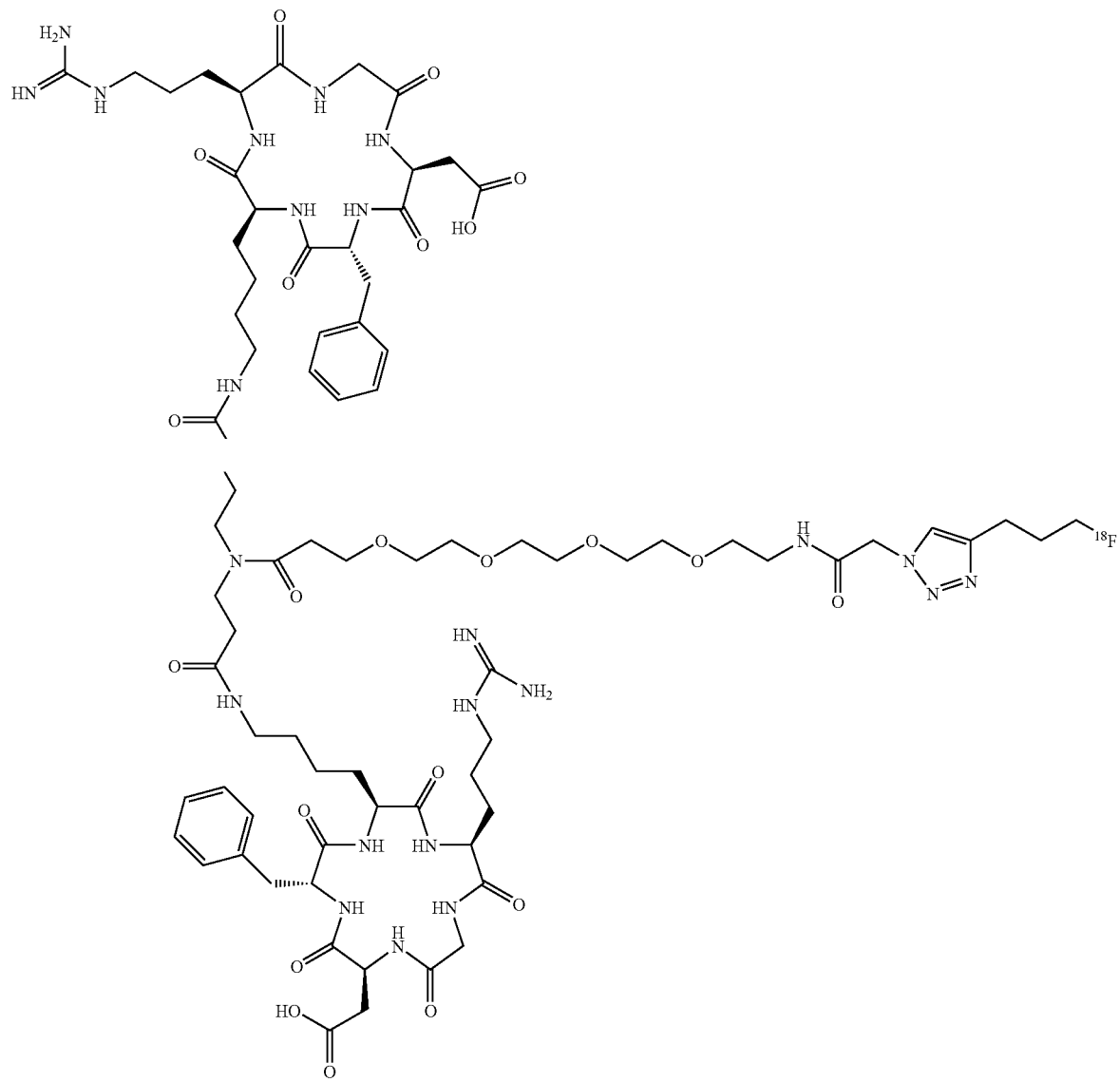

and a pharmaceutically acceptable carrier.

24. A method of monitoring the level of integrin $\alpha_v\beta_3$ or visualizing integrin $\alpha_v\beta_3$ expression within a body of a patient, the method comprising: (a) administering to the patient a radiolabeled cyclopeptide; and (b) employing a nuclear imaging technique selected from the group consisting of positron emission tomography (PET) and single photon emission computed tomography (SPECT) for monitoring or visualizing a distribution of the radiolabeled cyclopeptide within the body or within a portion thereof; wherein the radiolabeled cyclopeptide is of formula I:

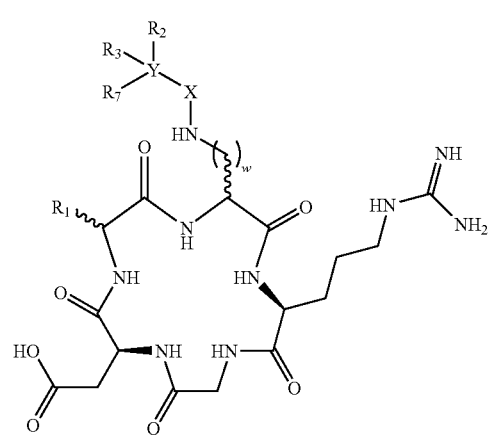

wherein

R₁ is selected from the group consisting of a side chain of a natural amino acid and a side chain of an unnatural amino acid, wherein the natural amino acid and the unnatural amino acid is either in the D or L form;

R₂ and R₃ are each independently selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted;

R₇ is absent or is selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted; wherein R₂, R₃ and R₇ are not all H;

X is a 5 or 6-membered heterocycle or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

Y is a 5 or 6-membered heterocycle, or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

where at least one of X and Y, but not both X and Y is a 5 or 6-membered heterocycle; and w is 1, 2, 3, 4, or 5;

wherein any one of X, Y, R₂, R₃, and R₇ comprises a radionuclide selected from the group consisting of positron or gamma emitters.

25. A method of monitoring the level of integrin $\alpha_v\beta_3$ or visualizing integrin $\alpha_v\beta_3$ expression within a body of a patient, the method comprising: (a) administering to the patient a radiolabeled cyclopeptide; and (b) employing a nuclear imaging technique selected from the group consisting of positron emission tomography (PET) and single photon emission computed tomography (SPECT) for monitoring or visualizing a distribution of the radiolabeled cyclopeptide within the body or within a portion thereof; wherein the radiolabeled cyclopeptide is of formula II or formula III:

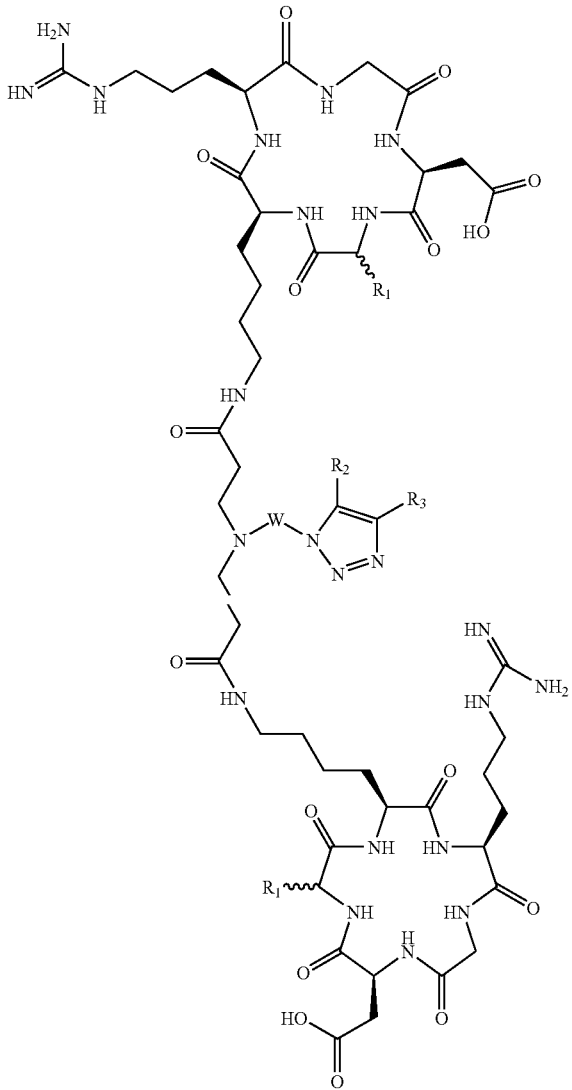

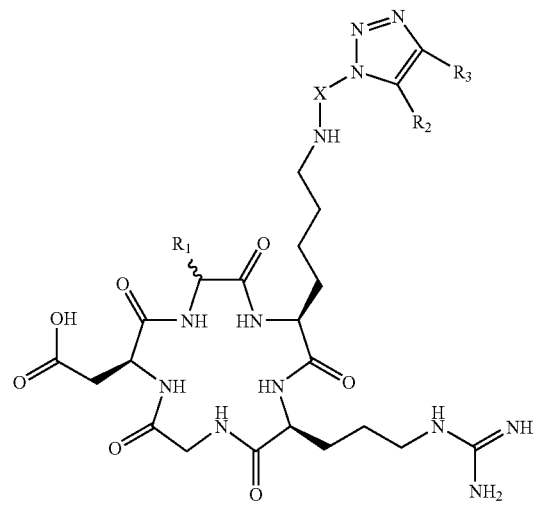

wherein
  each $R_1$ is independently selected from the group consisting of a side chain of a natural amino acid and a side chain of an unnatural amino acid, wherein the natural amino acid and the unnatural amino acid is either in the D or L form;
  $R_2$ and $R_3$ are each independently selected from the group consisting of —H, $C_1$-$C_6$ alkyl, $C_2$-$C_6$ alkenyl, and $C_2$-$C_6$ alkynyl, wherein the alkyl, alkenyl, and alkynyl groups are optionally substituted, wherein $R_2$ and $R_3$ are not both H; and either $R_2$ or $R_3$, or both $R_2$ and $R_3$ comprise a radionuclide selected from the group consisting of $^{11}$C, $^{13}$N, $^{15}$O, $^{18}$F, $^{61}$Cu, $^{62}$Cu, $^{67}$Cu, $^{68}$Ga, $^{124}$I, $^{125}$I, $^{131}$I, $^{99}$Tc, $^{75}$Br, $^{153}$Gd and $^{32}$P;
  each of X and W is selected from the group consisting of:

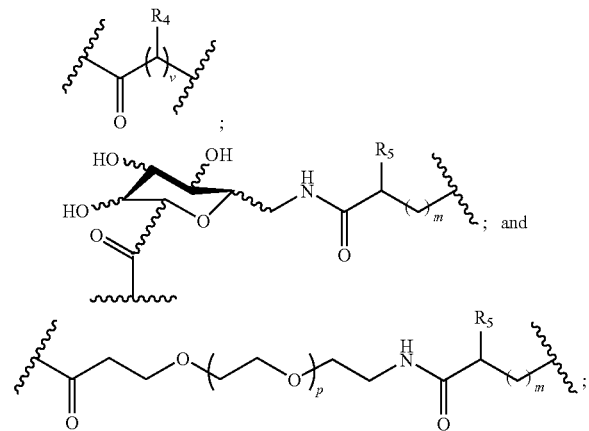

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;
  $R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted;
  wherein the configuration of the chiral centers may be R or S or mixtures thereof;
  v is 0, 1, 2, 3, or 4;
  m is 0, 1, 2, 3 or 4; and
  p is an integer between 1 and 25.

26. A method of monitoring the level of integrin $\alpha_v\beta_3$ or visualizing integrin $\alpha_v\beta_3$ expression within a body of a patient, the method comprising: (a) administering to the patient a radiolabeled cyclopeptide; and (b) employing a nuclear imaging technique selected from the group consisting of positron emission tomography (PET) and single photon emission computed tomography (SPECT) for monitoring or visualizing a distribution of the radiolabeled cyclopeptide within the body or within a portion thereof; wherein the radiolabeled cyclopeptide is selected from the group consisting of:

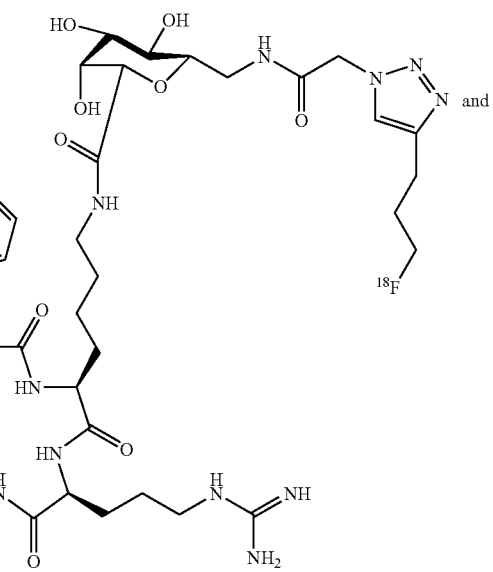

-continued

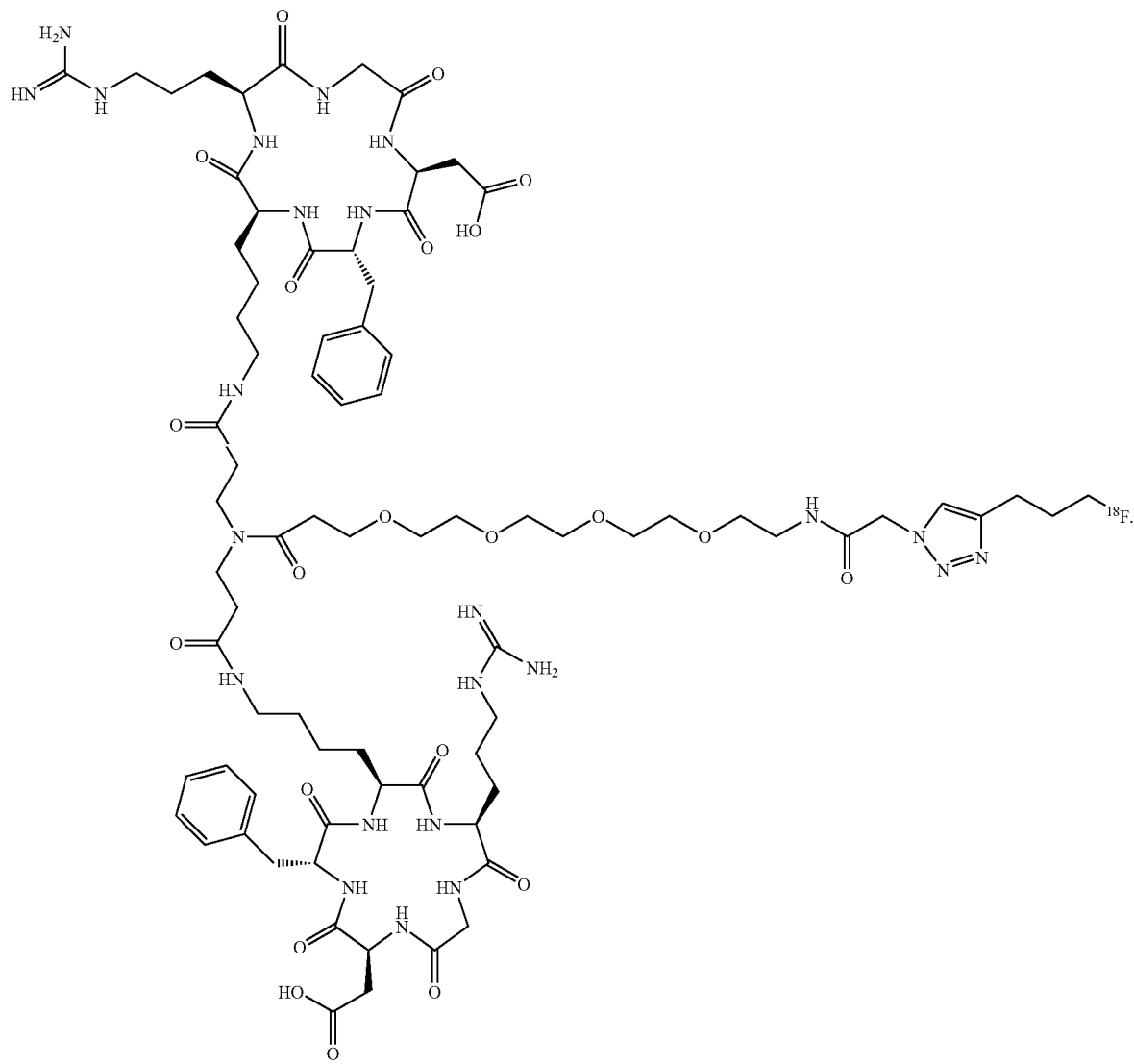

27. A method for imaging of blood vessel growth in solid tumors based on expression of integrin $\alpha_v\beta_3$ within the body of a patient, the method comprising: (a) administering to the patient a radiolabeled cyclopeptide; (b) employing a nuclear imaging technique selected from the group consisting of positron emission tomography (PET) and single photon emission computed tomography (SPECT) for imaging a distribution of the radiolabeled cyclopeptide within the body or within a portion thereof; and c) correlating the distribution of the radiolabeled cyclopeptide to the growth of blood vessels in solid tumors, wherein the radiolabeled cyclopeptide is of formula I:

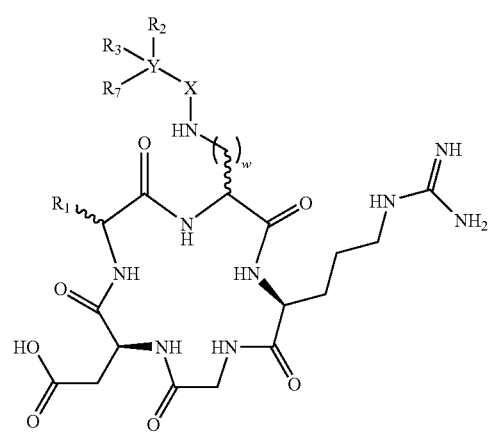

wherein

R₁ is selected from the group consisting of a side chain of a natural amino acid and a side chain of an unnatural amino acid, wherein the natural amino acid and the unnatural amino acid is either in the D or L form;

R₂ and R₃ are each independently selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted;

R₇ is absent or is selected from the group consisting of H, $C_1$-$C_6$ alkyl, $C_2$-$C_6$ alkenyl, $C_2$-$C_6$ alkynyl, aryl, aryl-($C_1$-$C_6$ alkylene)-, a 3- to 7-membered carbocycle, and a 3- to 7-membered heterocycle, wherein the alkyl, alkenyl, alkynyl, aryl-alkylene, carbocycle and heterocycle groups are each optionally substituted; wherein R₂, R₃ and R₇ are not all H;

X is a 5 or 6-membered heterocycle or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

Y is a 5 or 6-membered heterocycle, or a linker comprising a hydrophilic moiety selected from the group consisting of hydroxyl, carbonyl, sulfonamide, sulfonate, phosphate, polar amino acid moiety, PEG moiety, sugar mimetic, and sugar moiety;

where at least one of X and Y, but not both X and Y is a 5 or 6-membered heterocycle; and w is 1, 2, 3, 4, or 5;
wherein any one of X, Y, R₂, R₃, and R₇ comprises a radionuclide selected from the group consisting of positron or gamma emitters.

28. A method for imaging of blood vessel growth in solid tumors based on expression of integrin $\alpha_v\beta_3$ within the body of a patient, the method comprising: (a) administering to the patient a radiolabeled cyclopeptide; (b) employing a nuclear imaging technique selected from the group consisting of positron emission tomography (PET) and single photon emission computed tomography (SPECT) for imaging a distribution of the radiolabeled cyclopeptide within the body or within a portion thereof; and c) correlating the distribution of the radiolabeled cyclopeptide to the growth of blood vessels in solid tumors, wherein the radiolabeled cyclopeptide is of formula II or formula III:

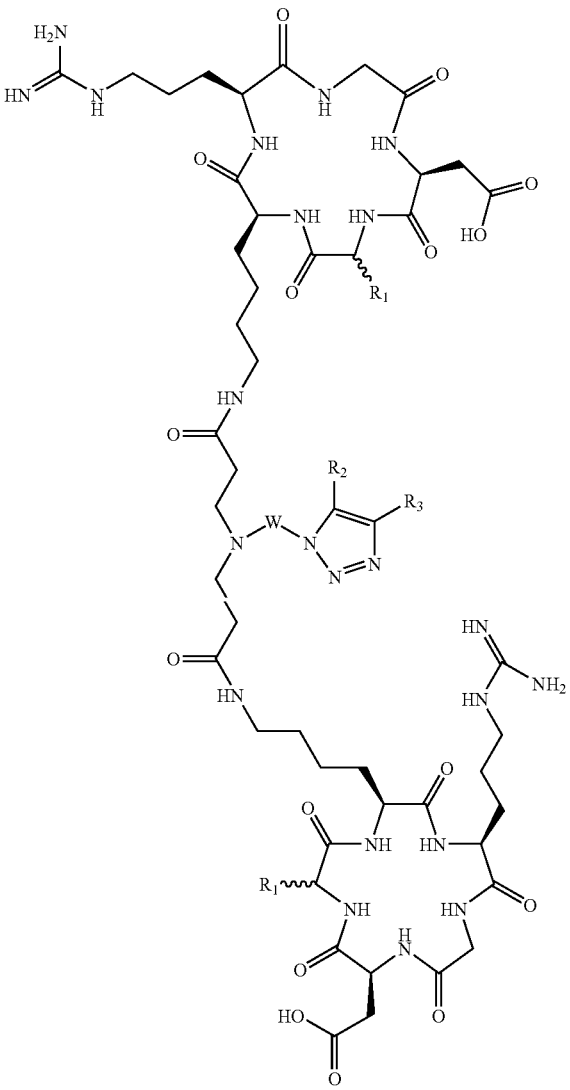

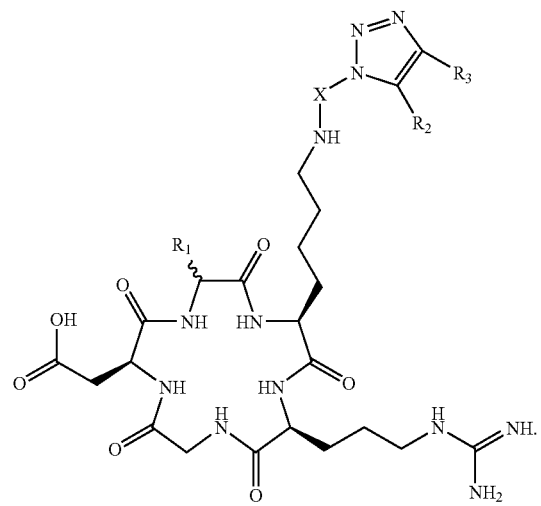

wherein:
each $R_1$ is independently selected from the group consisting of a side chain of a natural amino acid and a side chain of an unnatural amino acid, wherein the natural amino acid and the unnatural amino acid is either in the D or L form;

$R_2$ and $R_3$ are each independently selected from the group consisting of —H, $C_1$-$C_6$ alkyl, $C_2$-$C_6$ alkenyl, and $C_2$-$C_6$ alkynyl, wherein the alkyl, alkenyl, and alkynyl groups are optionally substituted, wherein $R_2$ and $R_3$ are not both H; and either $R_2$ or $R_3$, or both $R_2$ and $R_3$ comprise a radionuclide selected from the group consisting of $^{11}C$, $^{13}N$, $^{15}O$, $^{18}F$, $^{61}Cu$, $^{62}Cu$, $^{64}Cu$, 67Cu, $^{68}Ga$, $^{124}I$, $^{125}I$, $^{131}I$, $^{99}Tc$, $^{75}Br$, $^{153}Gd$ and $^{32}P$;

each of X and W is selected from the group consisting of:

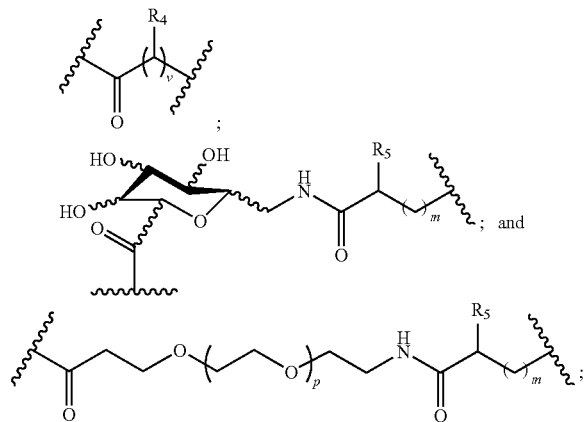

where each $R_4$ is independently selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, $C_1$-$C_6$-alkoxy-$C_1$-$C_6$-alkyl, and a PEG moiety, wherein the alkyl, alkenyl, alkynyl, alkoxy, aryl, carbocycle, and heterocycle groups are each optionally substituted;

$R_5$ is selected from the group consisting of —H, $C_1$-$C_6$ alkyl, $C_2$-$C_6$ alkenyl, $C_2$-$C_6$ alkynyl, $C_1$-$C_6$ alkyloxy, aryl, aryl-($C_1$-$C_6$ alkylene)-, 3- to 7-membered carbocycle, 3- to 7-membered heterocycle, hydroxy-$C_1$-$C_6$-alkyl, and $C_1$-$C_6$-alkoxy-$C_1$-$C_6$-alkyl, wherein the alkyl, alkenyl, alkynyl, alkyloxy, aryl, carbocycle, and heterocycle, groups are each optionally substituted;

wherein the configuration of the chiral centers may be R or S or mixtures thereof;

v is 0, 1, 2, 3, or 4;

m is 0, 1, 2, 3 or 4; and p is an integer between 1 and 25.

29. A method for imaging of blood vessel growth in solid tumors based on expression of integrin $\alpha_v\beta_3$ within the body of a patient, the method comprising: (a) administering to the patient a radiolabeled cyclopeptide; (b) employing a nuclear imaging technique selected from the group consisting of positron emission tomography (PET) and single photon emission computed tomography (SPECT) for imaging a distribution of the radiolabeled cyclopeptide within the body or within a portion thereof; and c) correlating the distribution of the radiolabeled cyclopeptide to the growth of blood vessels in solid tumors, wherein the radiolabeled cyclopeptide is selected from the group consisting of:

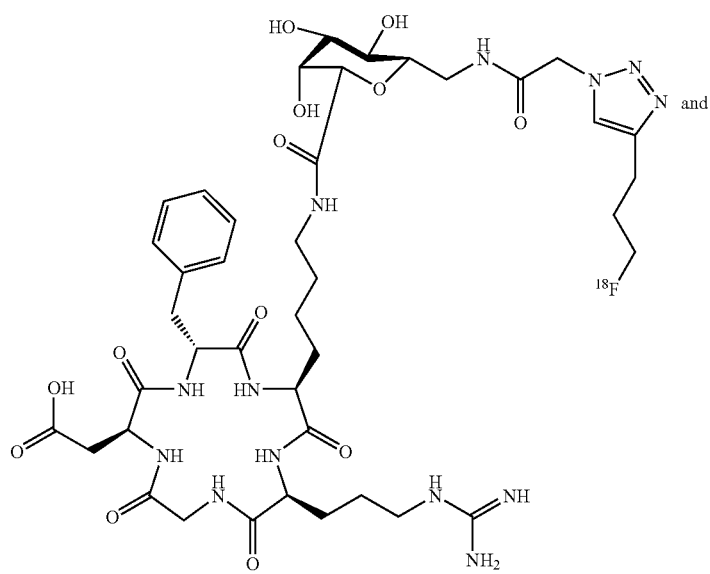

-continued
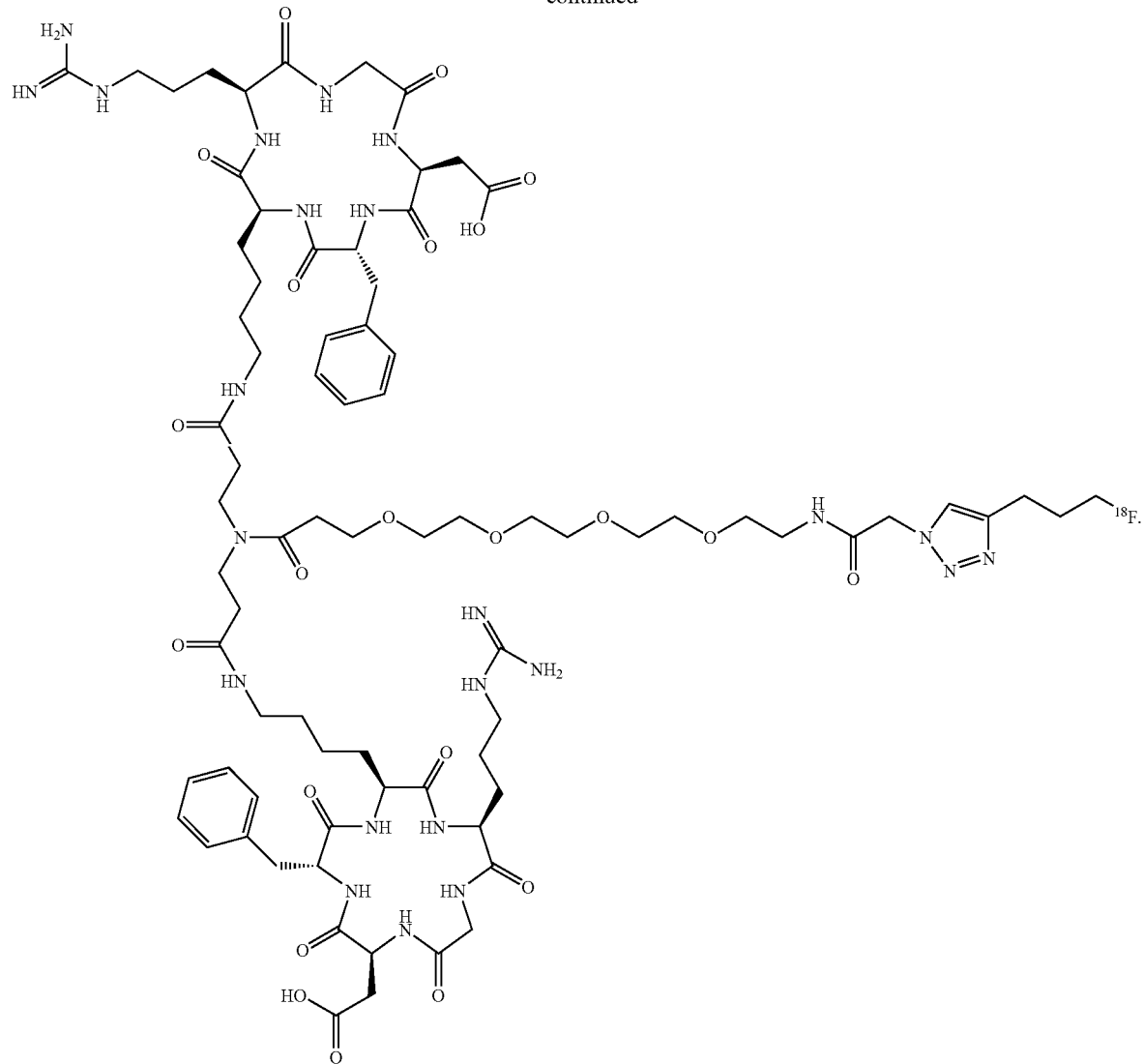
* * * * *